(12) United States Patent
Ichige et al.

(10) Patent No.: US 7,531,330 B2
(45) Date of Patent: May 12, 2009

(54) MODIFIED S-HYDROXYNITRILE LYASE

(75) Inventors: Eita Ichige, Chiba (JP); Hisashi Semba, Ibaraki (JP); Toshiaki Shijuku, Chiba (JP); Shigeaki Harayama, Chiba (JP)

(73) Assignee: Nippon Shokubai Co., Ltd., Osaka ( * ) Notice: Subject to any disclaimer, the term of this patent is extended or adjusted under 35 U.S.C. 154(b) by 60 days.

(21) Appl. No.: 10/594,732

(22) PCT Filed: Mar. 30, 2005

(86) PCT No.: PCT/JP2005/006730

§ 371 (c)(1),
(2), (4) Date: Sep. 29, 2006

(87) PCT Pub. No.: WO2005/095602

PCT Pub. Date: Oct. 13, 2005

(65) Prior Publication Data

US 2008/0124784 A1 May 29, 2008

(30) Foreign Application Priority Data

Mar. 31, 2004 (JP) ............................. 2004-105642

(51) Int. Cl.
C12P 13/00 (2006.01)
C12N 9/88 (2006.01)
C12P 21/06 (2006.01)
C12N 15/74 (2006.01)
C07H 21/04 (2006.01)

(52) U.S. Cl. ...................................... 435/128; 435/232
(58) Field of Classification Search ....................... None
See application file for complete search history.

(56) References Cited

U.S. PATENT DOCUMENTS 6,046,042 A    4/2000    Hasslacher et al.

FOREIGN PATENT DOCUMENTS

| EP | 1 433 853 A2 | 6/2004 |
| EP | 1 433 853 A3 | 6/2004 |
| JP | 2000-125886 | 5/2000 |
| WO | WO 97/03204 A2 | 1/1997 |
| WO | WO 97/03204 A3 | 1/1997 |

OTHER PUBLICATIONS

UniProt Accession No. P52705, created Oct. 1, 1996.*

Hasslacher et al., "Hydroxynitrile lyase from *Hevea brasiliensis*: Molecular Characterizaton and Mechanism of Enzyme Catalysis," Proteins: Structure, Function, and Genetics, 27: 438-449 (1997).
Hughes et al., "Purfication, Characterization, and Cloning of α-Hydroxynitrile Lyase from Cassava (*Manihot esculenta* Crantz)," Archives of Biochemistry and Biophysics, 311(2): 496-502 (1994).
Wagner et al., "Mechanism of Cyanogenesis: The Crystal Structure of Hydroxynitrile Lyase from *Hevea brasiliensis*," Structure, 4(7): 811-822 (1996).
Communication containing the Supplemental European Search Report mailed Feb. 22, 2008, for EP Application No. EP 05728634.6-2405, 5 pages.
Gruber et al., "Biopolymers for Biocatalysis: Structure and Catalytic Mechanism of Hydroxynitrile Lyases", Journal of Polymer Science: Part A: Polymer Chemistry, vol. 42, pp. 479-486, (2004).
Hasslacher et al., "Molecular Cloning of the Full-Length cDNA of (S)-Hydroxynitrile Lyase From *Hevea brasiliensis*", The Journal of Biological Chemistry, vol. 271, No. 10, pp. 5884-5891, (1996).
Yan et al., "A Single Residual Replacement Improves the Folding and Stability of Recombinant Cassava Hydroxynitrile Lyase in *E. coli*", Biotechnology Letters, vol. 25, pp. 1041-1047, (2003).
Glieder et al., "Comprehensive Step-By-Step Engineering of an (R)-Hydroxynitrile Lyase for Large-Scale Asymmetric Synthesis", Angew. Chem. Int. Ed., vol. 42, pp. 4815-4818, (2003).
Lauble et al., "Crystal Structure of Hydroxynitrile Lyase From *Sorghum Bicolor* in Complex With the Inhibitor Benzoic Acid: A Novel Cyanogenic Enzyme", Biochemistry, vol. 41, pp. 12043-12050, (2002).
Stranzl et al., "Observation of a Short, Strong Hydrogen Bond in the Active Site of Hydroxynitrile Lyase From *Hevea brasiliensis* Explains a Large $pK_\alpha$ Shift of the Catalytic Base Induced by the Reaction Intermediate", The Journal of Biological Chemistry, vol. 279, No. 5, pp. 3699-3707, (2004).
Lauble et al., "Mechanistic Aspects of Cyanogenesis From Active-Site Mutant SER80ALA of Hydroxynitrile Lyase From *Manihot esculenta* in Complex With Acetone Cyanohydrin", Protein Science, vol. 10, pp. 1015-1022, (2001).
Lauble et al., "Structure Determinants of Substrate Specificity of Hydroxynitrile Lyase From *Manihot esculenta*", Protein Science, vol. 11, pp. 65-71, (2002).
Baik et al., "Significantly Enhanced Stability of Glucose Dehydrogenase by Directed Evolution", Appl. Microbiol. Biotechnol., vol. 61, pp. 329-335, (2003).

\* cited by examiner

*Primary Examiner*—Nashaat T Nashed
*Assistant Examiner*—Iqbal H Chowdhury
(74) *Attorney, Agent, or Firm*—Finnegan, Henderson, Farabow, Garrett, & Dunner L.L.P.

(57) ABSTRACT

This invention relates to S-hydroxynitrile lyase having excellent tolerance to heat, organic solvents, and the like, which is obtained by modifying at least one amino acid in the helix D3, helix A, and β-sheet 2 domains in the amino acid sequence of wild-type S-hydroxynitrile lyase.

5 Claims, 21 Drawing Sheets
(4 of 21 Drawing Sheet(s) Filed in Color)

Fig. 6
A
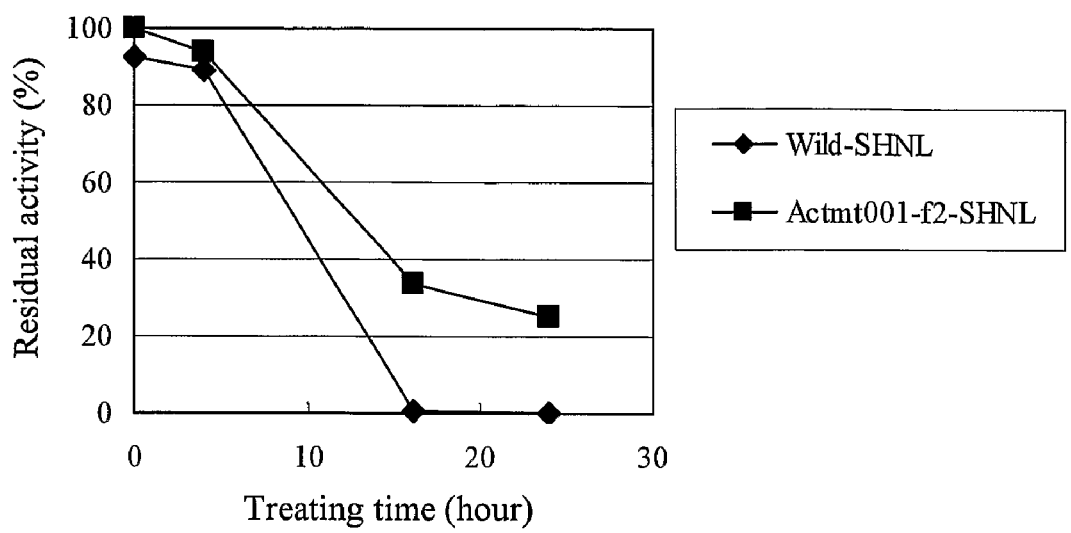
B
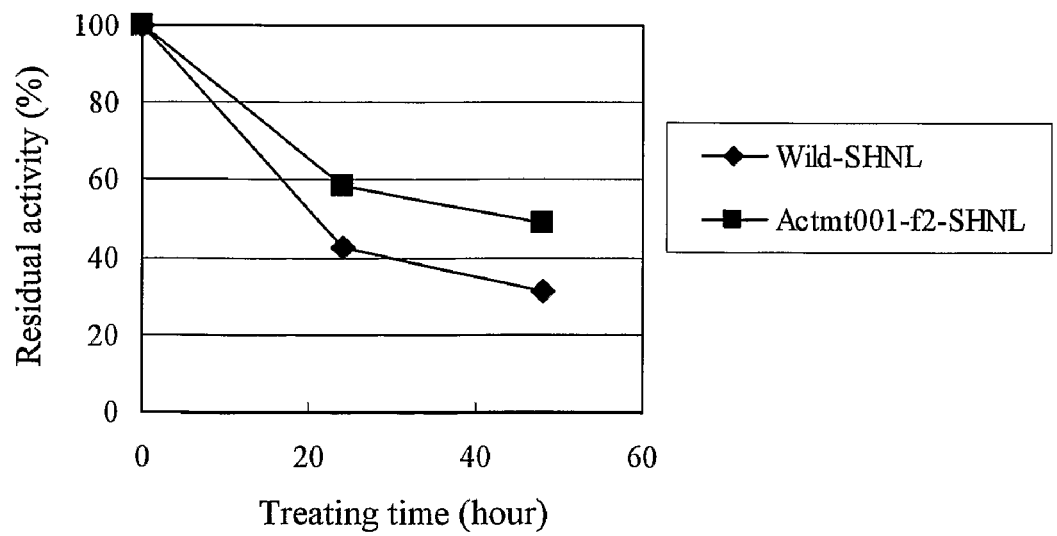

Fig. 8
A
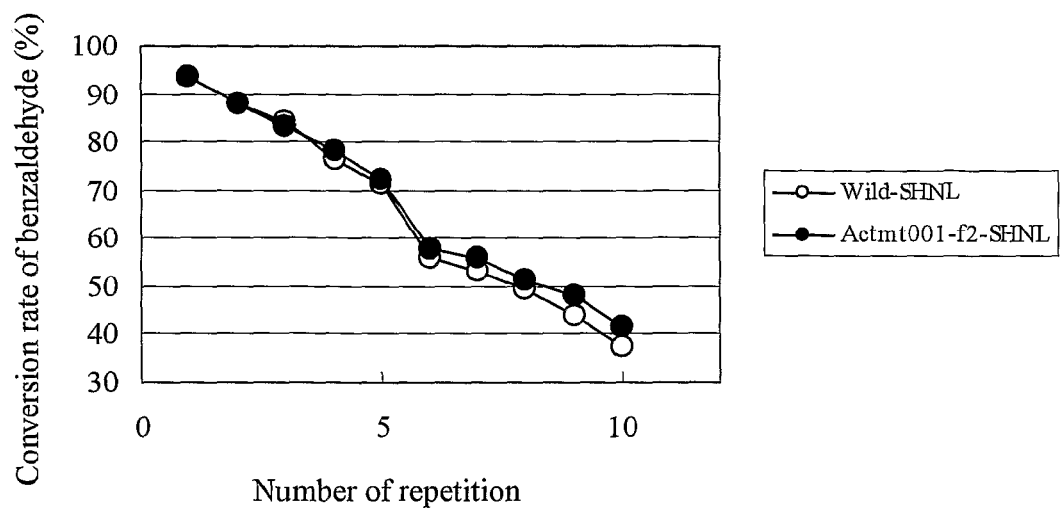
B
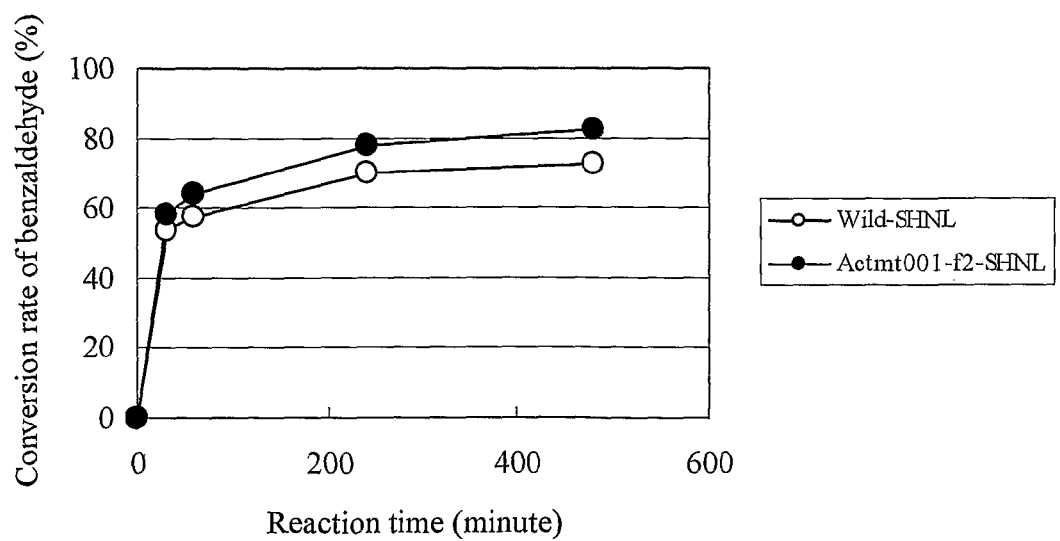

Fig. 13

```
Hevea brasiliensis    1:MAFAHFVLIHTICHGAWIWHKLKPLLEALGHKVTALDLAASGVDPRQIEEIGSFDEYSEP  60
Manihot esculenta     1:MVTAHFVLIHTICHGAWIWHKLKPALERAGHKVTALDMAASGIDPRQIEQINSFDEYSEP 60
                        * ************** ****** ** ***** *** ** *** ** * *****

Hevea brasiliensis   61:LLTELEALPPGEKVILVGESCGGLNIAIAADKYCEKIAAAVFHNSVLPDTEHCPSYVVDK 120
Manihot esculenta    61:LLTELEKLPQGEKVIIVGESCAGLNIAIAADRYVDKIAAGVFHNSLLPDTVHSPSYTVEK 120
                        ****** ** ***** ***** ********* *  *** ***** ****  ***  *

Hevea brasiliensis  121:LMEVFPDWKDTTYEFYTKDGKE-ITGLKLGFTLLRENLYTLCGPEEYELAKMLTRKGSLF 179
Manihot esculenta   121:LLESFPDWRDTEYFTFTNITGETITTMKLGFVLLRENLFTKCTDGEYELAKMVMRKGSLF 180
                         * * **** ** *  *    *  ** *** ****** *    * ******* ******

Hevea brasiliensis  180:QNILAKRPFFTKEGYGSIKKIYVWTDQDEIFLPEFQLMQIENYKPDKVYKVEGGDHKLQL 239
Manihot esculenta   181:QNVLAQRPKFTEKGYGSIKKVYIWTDQDKIFLPDFQRWQIANYKPDKVYQVQGGDHKLQL 240
                        ** ** ** ** ******* * ****** ***** *  ** ******* * *******

Hevea brasiliensis  240:TKTKEIAEILQEVADTYN                                          257
Manihot esculenta   241:TKTEEVAHILQEVADAYA                                          258
                        *** *   ******* *
```

Heating time (30min)

Fig. 15
A
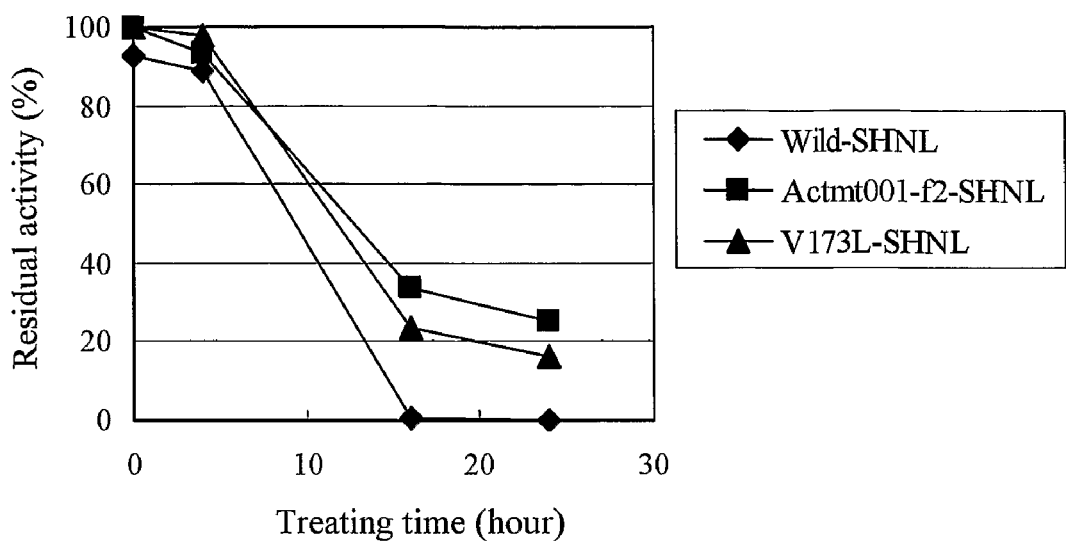
B
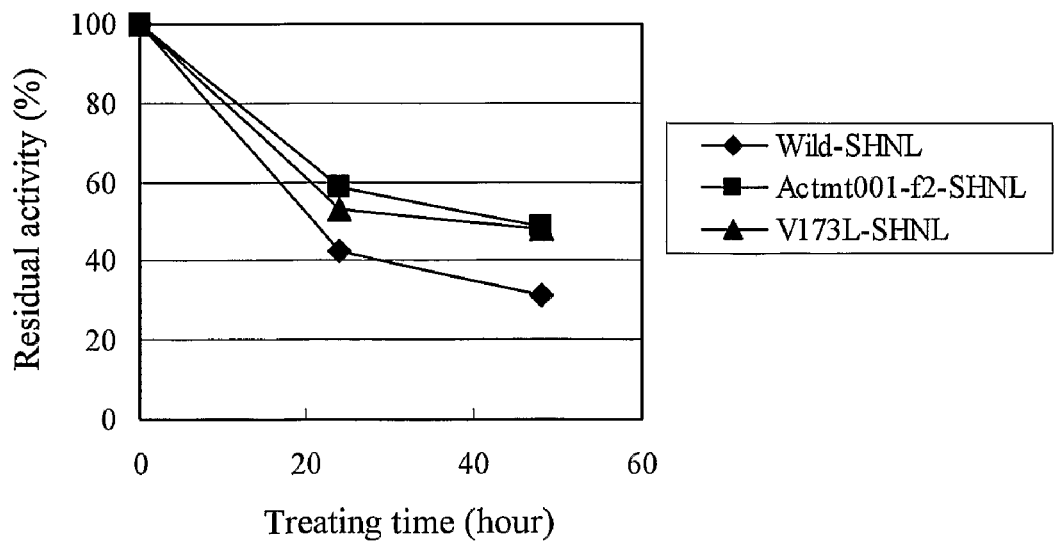

SEQUENCE LISTING

```
<160> NUMBER OF SEQ ID NOS: 44

<210> SEQ ID NO 1
<211> LENGTH: 777
<212> TYPE: DNA
<213> ORGANISM: Manihot esculenta
<220> FEATURE:
<223> OTHER INFORMATION: Inventor: Ichige, Eita; Semba, Hisashi;
      Shijuku, Toshiaki; Harayama, Shigeaki
<220> FEATURE:
<221> NAME/KEY: CDS
<222> LOCATION: (1)..(777)

<400> SEQUENCE: 1 atg gtt act gca cac ttc gtt ctg att cac acc att tgt cac ggc gca        48
Met Val Thr Ala His Phe Val Leu Ile His Thr Ile Cys His Gly Ala
1               5                   10                  15 tgg att tgg cac aaa ctg aaa ccg gcc ctg gaa cgt gct ggc cac aaa        96
Trp Ile Trp His Lys Leu Lys Pro Ala Leu Glu Arg Ala Gly His Lys
            20                  25                  30 gtt act gca ctg gac atg gca gcc agt ggc att gac ccg cgt caa att       144
Val Thr Ala Leu Asp Met Ala Ala Ser Gly Ile Asp Pro Arg Gln Ile
        35                  40                  45 gaa cag atc aac tct ttc gat gaa tac tct gaa ccg ctg ctg act ttc       192
Glu Gln Ile Asn Ser Phe Asp Glu Tyr Ser Glu Pro Leu Leu Thr Phe
```

```
                   50                  55                  60
ctg gaa aaa ctg ccg caa ggc gaa aag gtt atc att gtt ggt gaa agc      240
Leu Glu Lys Leu Pro Gln Gly Glu Lys Val Ile Ile Val Gly Glu Ser
 65                  70                  75                  80 tgt gca ggc ctg aac att gct att gct gct gat cgt tac gtt gac aaa      288
Cys Ala Gly Leu Asn Ile Ala Ile Ala Ala Asp Arg Tyr Val Asp Lys
                 85                  90                  95 att gca gct ggc gtt ttc cac aac tcc ctg ctg ccg gac acc gtt cac      336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg      384
Ser Pro Ser Tyr Thr Val Glu Lys Leu Leu Glu Ser Phe Pro Asp Trp
        115                 120                 125 cgt gac aca gaa tat ttc acg ttc acc aac atc act ggc gaa acc atc      432
Arg Asp Thr Glu Tyr Phe Thr Phe Thr Asn Ile Thr Gly Glu Thr Ile
    130                 135                 140 act acc atg aaa ctg ggt ttc gtt ctg ctg cgt gaa aac ctg ttc acc      480
Thr Thr Met Lys Leu Gly Phe Val Leu Leu Arg Glu Asn Leu Phe Thr
145                 150                 155                 160 aaa tgc act gat ggc gaa tat gaa ctg gca aaa atg gtt atg cgc aag      528
Lys Cys Thr Asp Gly Glu Tyr Glu Leu Ala Lys Met Val Met Arg Lys
                165                 170                 175 ggc tct ctg ttc caa aac gtt ctg gct cag cgt ccg aag ttc act gaa      576
Gly Ser Leu Phe Gln Asn Val Leu Ala Gln Arg Pro Lys Phe Thr Glu
            180                 185                 190 aaa ggc tac ggc tct atc aag aaa gtt tat att tgg acc gat caa gac      624
Lys Gly Tyr Gly Ser Ile Lys Lys Val Tyr Ile Trp Thr Asp Gln Asp
        195                 200                 205 aaa ata ttc ctg ccg gac ttc caa cgc tgg caa att gca aac tac aaa      672
Lys Ile Phe Leu Pro Asp Phe Gln Arg Trp Gln Ile Ala Asn Tyr Lys
    210                 215                 220 ccg gac aag gtt tat cag gtt caa ggc ggc gat cac aag ctg cag ctg      720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca      768
Thr Lys Thr Glu Glu Val Ala His Ile Leu Gln Glu Val Ala Asp Ala
                245                 250                 255 tac gct taa                                                          777
Tyr Ala <210> SEQ ID NO 2
<211> LENGTH: 258
<212> TYPE: PRT
<213> ORGANISM: Manihot esculenta

<400> SEQUENCE: 2

Met Val Thr Ala His Phe Val Leu Ile His Thr Ile Cys His Gly Ala
 1               5                  10                  15

Trp Ile Trp His Lys Leu Lys Pro Ala Leu Glu Arg Ala Gly His Lys
                20                  25                  30

Val Thr Ala Leu Asp Met Ala Ala Ser Gly Ile Asp Pro Arg Gln Ile
            35                  40                  45

Glu Gln Ile Asn Ser Phe Asp Glu Tyr Ser Glu Pro Leu Leu Thr Phe
        50                  55                  60

Leu Glu Lys Leu Pro Gln Gly Glu Lys Val Ile Ile Val Gly Glu Ser
 65                  70                  75                  80

Cys Ala Gly Leu Asn Ile Ala Ile Ala Ala Asp Arg Tyr Val Asp Lys
                85                  90                  95
```

```
Ile Ala Ala Gly Val Phe His Asn Ser Leu Leu Pro Asp Thr Val His
        100                 105                 110
Ser Pro Ser Tyr Thr Val Glu Lys Leu Leu Glu Ser Phe Pro Asp Trp
    115                 120                 125
Arg Asp Thr Glu Tyr Phe Thr Phe Thr Asn Ile Thr Gly Glu Thr Ile
130                 135                 140
Thr Thr Met Lys Leu Gly Phe Val Leu Leu Arg Glu Asn Leu Phe Thr
145                 150                 155                 160
Lys Cys Thr Asp Gly Glu Tyr Glu Leu Ala Lys Met Val Met Arg Lys
                165                 170                 175
Gly Ser Leu Phe Gln Asn Val Leu Ala Gln Arg Pro Lys Phe Thr Glu
            180                 185                 190
Lys Gly Tyr Gly Ser Ile Lys Lys Val Tyr Ile Trp Thr Asp Gln Asp
        195                 200                 205
Lys Ile Phe Leu Pro Asp Phe Gln Arg Trp Gln Ile Ala Asn Tyr Lys
    210                 215                 220
Pro Asp Lys Val Tyr Gln Val Gln Gly Gly Asp His Lys Leu Gln Leu
225                 230                 235                 240
Thr Lys Thr Glu Glu Val Ala His Ile Leu Gln Glu Val Ala Asp Ala
                245                 250                 255
Tyr Ala

<210> SEQ ID NO 3
<211> LENGTH: 774
<212> TYPE: DNA
<213> ORGANISM: Hevea brasiliensis
<220> FEATURE:
<221> NAME/KEY: CDS
<222> LOCATION: (1)..(774)

<400> SEQUENCE: 3 atg gca ttc gct cat ttt gtt ctt att cat acc ata tgc cac ggt gca      48
Met Ala Phe Ala His Phe Val Leu Ile His Thr Ile Cys His Gly Ala
1               5                   10                  15 tgg att tgg cac aag ctc aaa ccc ctc ctt gag gca ctt ggc cac aag      96
Trp Ile Trp His Lys Leu Lys Pro Leu Leu Glu Ala Leu Gly His Lys
            20                  25                  30 gtt act gca ctg gac ctt gca gca agc ggc gtt gac cca agg caa att     144
Val Thr Ala Leu Asp Leu Ala Ala Ser Gly Val Asp Pro Arg Gln Ile
        35                  40                  45 gag gag att ggc tca ttt gat gag tat tct gaa ccc ttg ttg acg ttc     192
Glu Glu Ile Gly Ser Phe Asp Glu Tyr Ser Glu Pro Leu Leu Thr Phe
    50                  55                  60 ttg gag gca ctc cct cca ggg gaa aag gtg att ctg gtt ggc gag agc     240
Leu Glu Ala Leu Pro Pro Gly Glu Lys Val Ile Leu Val Gly Glu Ser
65                  70                  75                  80 tgt gga gga ctc aat ata gca att gct gct gat aaa tac tgt gaa aag     288
Cys Gly Gly Leu Asn Ile Ala Ile Ala Ala Asp Lys Tyr Cys Glu Lys
                85                  90                  95 att gca gct gct gtt ttc cac aat tca gta ttg cca gac acc gag cac     336
Ile Ala Ala Ala Val Phe His Asn Ser Val Leu Pro Asp Thr Glu His
            100                 105                 110 tgc cca tct tac gtc gtg gat aag ctc atg gag gtg ttt ccc gac tgg     384
Cys Pro Ser Tyr Val Val Asp Lys Leu Met Glu Val Phe Pro Asp Trp
        115                 120                 125 aaa gac acc acg tat ttt acg tac act aaa gat ggc aag gag ata act     432
Lys Asp Thr Thr Tyr Phe Thr Tyr Thr Lys Asp Gly Lys Glu Ile Thr
    130                 135                 140
```

```
gga ttg aaa ctg ggc ttc acg ctt ctg agg gaa aat tta tat acc ctt    480
Gly Leu Lys Leu Gly Phe Thr Leu Leu Arg Glu Asn Leu Tyr Thr Leu
145                 150                 155                 160 tgc ggt cct gag gaa tat gaa ctg gcg aag atg ttg aca agg aag gga    528
Cys Gly Pro Glu Glu Tyr Glu Leu Ala Lys Met Leu Thr Arg Lys Gly
                165                 170                 175 tca tta ttt caa aat att tta gct aag cga cca ttc ttc act aag gaa    576
Ser Leu Phe Gln Asn Ile Leu Ala Lys Arg Pro Phe Phe Thr Lys Glu
            180                 185                 190 ggt tac gga tcg att aag aaa att tat gtg tgg acc gac caa gac gaa    624
Gly Tyr Gly Ser Ile Lys Lys Ile Tyr Val Trp Thr Asp Gln Asp Glu
        195                 200                 205 ata ttt tta cct gaa ttt caa ctc tgg caa ata gaa aac tat aaa cca    672
Ile Phe Leu Pro Glu Phe Gln Leu Trp Gln Ile Glu Asn Tyr Lys Pro
    210                 215                 220 gac aag gtt tat aag gtc gaa ggt gga gat cat aaa ttg cag ctt aca    720
Asp Lys Val Tyr Lys Val Glu Gly Gly Asp His Lys Leu Gln Leu Thr
225                 230                 235                 240 aag act aag gag atc gct gaa att ctc caa gag gtg gct gat acc tat    768
Lys Thr Lys Glu Ile Ala Glu Ile Leu Gln Glu Val Ala Asp Thr Tyr
                245                 250                 255 aat tga                                                            774
Asn

<210> SEQ ID NO 4
<211> LENGTH: 257
<212> TYPE: PRT
<213> ORGANISM: Hevea brasiliensis

<400> SEQUENCE: 4

Met Ala Phe Ala His Phe Val Leu Ile His Thr Ile Cys His Gly Ala
1               5                   10                  15

Trp Ile Trp His Lys Leu Lys Pro Leu Leu Glu Ala Leu Gly His Lys
            20                  25                  30

Val Thr Ala Leu Asp Leu Ala Ala Ser Gly Val Asp Pro Arg Gln Ile
        35                  40                  45

Glu Glu Ile Gly Ser Phe Asp Glu Tyr Ser Glu Pro Leu Leu Thr Phe
    50                  55                  60

Leu Glu Ala Leu Pro Pro Gly Glu Lys Val Ile Leu Val Gly Glu Ser
65                  70                  75                  80

Cys Gly Gly Leu Asn Ile Ala Ile Ala Ala Asp Lys Tyr Cys Glu Lys
                85                  90                  95

Ile Ala Ala Ala Val Phe His Asn Ser Val Leu Pro Asp Thr Glu His
            100                 105                 110

Cys Pro Ser Tyr Val Val Asp Lys Leu Met Glu Val Phe Pro Asp Trp
        115                 120                 125

Lys Asp Thr Thr Tyr Phe Thr Tyr Thr Lys Asp Gly Lys Glu Ile Thr
    130                 135                 140

Gly Leu Lys Leu Gly Phe Thr Leu Leu Arg Glu Asn Leu Tyr Thr Leu
145                 150                 155                 160

Cys Gly Pro Glu Glu Tyr Glu Leu Ala Lys Met Leu Thr Arg Lys Gly
                165                 170                 175

Ser Leu Phe Gln Asn Ile Leu Ala Lys Arg Pro Phe Phe Thr Lys Glu
            180                 185                 190

Gly Tyr Gly Ser Ile Lys Lys Ile Tyr Val Trp Thr Asp Gln Asp Glu
        195                 200                 205

Ile Phe Leu Pro Glu Phe Gln Leu Trp Gln Ile Glu Asn Tyr Lys Pro
```

```
            210                 215                 220
Asp Lys Val Tyr Lys Val Glu Gly Gly Asp His Lys Leu Gln Leu Thr
225                 230                 235                 240

Lys Thr Lys Glu Ile Ala Glu Ile Leu Gln Glu Val Ala Asp Thr Tyr
                245                 250                 255

Asn

<210> SEQ ID NO 5
<211> LENGTH: 777
<212> TYPE: DNA
<213> ORGANISM: Manihot esculenta
<220> FEATURE:
<223> OTHER INFORMATION: cDNA coding for Modified SHNL involving
      a replacement of Gly by Asp at position 165
<220> FEATURE:
<221> NAME/KEY: CDS
<222> LOCATION: (1)..(777)

<400> SEQUENCE: 5 atg gtt act gca cac ttc gtt ctg att cac acc att tgt cac ggc gca      48
Met Val Thr Ala His Phe Val Leu Ile His Thr Ile Cys His Gly Ala
1               5                   10                  15 tgg att tgg cac aaa ctg aaa ccg gcc ctg gaa cgt gct ggc cac aaa      96
Trp Ile Trp His Lys Leu Lys Pro Ala Leu Glu Arg Ala Gly His Lys
            20                  25                  30 gtt act gca ctg gac atg gca gcc agt ggc att gac ccg cgt caa att    144
Val Thr Ala Leu Asp Met Ala Ala Ser Gly Ile Asp Pro Arg Gln Ile
        35                  40                  45 gaa cag atc aac tct ttc gat gaa tac tct gaa ccg ctg ctg act ttc    192
Glu Gln Ile Asn Ser Phe Asp Glu Tyr Ser Glu Pro Leu Leu Thr Phe
    50                  55                  60 ctg gaa aaa ctg ccg caa ggc gaa aag gtt atc att gtt ggt gaa agc    240
Leu Glu Lys Leu Pro Gln Gly Glu Lys Val Ile Ile Val Gly Glu Ser
65                  70                  75                  80 tgt gca ggc ctg aac att gct att gct gct gat cgt tac gtt gac aaa    288
Cys Ala Gly Leu Asn Ile Ala Ile Ala Ala Asp Arg Tyr Val Asp Lys
                85                  90                  95 att gca gct ggc gtt ttc cac aac tcc ctg ctg ccg gac acc gtt cac    336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg    384
Ser Pro Ser Tyr Thr Val Glu Lys Leu Leu Glu Ser Phe Pro Asp Trp
        115                 120                 125 cgt gac aca gaa tat ttc acg ttc acc aac atc act ggc gaa acc atc    432
Arg Asp Thr Glu Tyr Phe Thr Phe Thr Asn Ile Thr Gly Glu Thr Ile
    130                 135                 140 act acc atg aaa ctg ggt ttc gtt ctg ctg cgt gaa aac ctg ttc acc    480
Thr Thr Met Lys Leu Gly Phe Val Leu Leu Arg Glu Asn Leu Phe Thr
145                 150                 155                 160 aaa tgc act gat gac gaa tat gaa ctg gca aaa atg gtt atg cgc aag    528
Lys Cys Thr Asp Asp Glu Tyr Glu Leu Ala Lys Met Val Met Arg Lys
                165                 170                 175 ggc tct ctg ttc caa aac gtt ctg gct cag cgt ccg aag ttc act gaa    576
Gly Ser Leu Phe Gln Asn Val Leu Ala Gln Arg Pro Lys Phe Thr Glu
            180                 185                 190 aaa ggc tac ggc tct atc aag aaa gtt tat att tgg acc gat caa gac    624
Lys Gly Tyr Gly Ser Ile Lys Lys Val Tyr Ile Trp Thr Asp Gln Asp
        195                 200                 205 aaa ata ttc ctg ccg gac ttc caa cgc tgg caa att gca aac tac aaa    672
Lys Ile Phe Leu Pro Asp Phe Gln Arg Trp Gln Ile Ala Asn Tyr Lys
    210                 215                 220
```

```
ccg gac aag gtt tat cag gtt caa ggc ggc gat cac aag ctg cag ctg    720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca    768
Thr Lys Thr Glu Glu Val Ala His Ile Leu Gln Glu Val Ala Asp Ala
                245                 250                 255 tac gct taa                                                         777
Tyr Ala
```

<210> SEQ ID NO 6
<211> LENGTH: 258
<212> TYPE: PRT
<213> ORGANISM: Manihot esculenta
<220> FEATURE:
<223> OTHER INFORMATION: Modified SHNL involving
      a replacement of Gly by Asp at position 165

<400> SEQUENCE: 6

```
Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
            20                  25                  30

Val Thr Ala Leu Asp Met Ala Ala Ser Gly Ile Asp Pro Arg Gln Ile
        35                  40                  45

Glu Gln Ile Asn Ser Phe Asp Glu Tyr Ser Glu Pro Leu Leu Thr Phe
    50                  55                  60

Leu Glu Lys Leu Pro Gln Gly Glu Lys Val Ile Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
        115                 120                 125

Arg Asp Thr Glu Tyr Phe Thr Phe Thr Asn Ile Thr Gly Glu Thr Ile
    130                 135                 140

Thr Thr Met Lys Leu Gly Phe Val Leu Leu Arg Glu Asn Leu Phe Thr
145                 150                 155                 160

Lys Cys Thr Asp Asp Glu Tyr Glu Leu Ala Lys Met Val Met Arg Lys
                165                 170                 175

Gly Ser Leu Phe Gln Asn Val Leu Ala Gln Arg Pro Lys Phe Thr Glu
            180                 185                 190

Lys Gly Tyr Gly Ser Ile Lys Lys Val Tyr Ile Trp Thr Asp Gln Asp
        195                 200                 205

Lys Ile Phe Leu Pro Asp Phe Gln Arg Trp Gln Ile Ala Asn Tyr Lys
    210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
                245                 250                 255

Tyr Ala
```

<210> SEQ ID NO 7
<211> LENGTH: 777
<212> TYPE: DNA
<213> ORGANISM: Manihot esculenta
<220> FEATURE:

<210> SEQ ID NO 7
<211> LENGTH: 777
<212> TYPE: DNA
<213> ORGANISM: Artificial Sequence
<220> FEATURE:
<223> OTHER INFORMATION: synthetic construct
<220> FEATURE:
<221> NAME/KEY: CDS
<222> LOCATION: (1)..(777)
<220> FEATURE:
<223> OTHER INFORMATION: cDNA coding for Modified SHNL involving a replacement of Gly by Glu at position 165

<400> SEQUENCE: 7

| | | | | | | | | | | | | | | | | |
|---|---|---|---|---|---|---|---|---|---|---|---|---|---|---|---|---|
| atg | gtt | act | gca | cac | ttc | gtt | ctg | att | cac | acc | att | tgt | cac | ggc | gca | 48 |
| Met | Val | Thr | Ala | His | Phe | Val | Leu | Ile | His | Thr | Ile | Cys | His | Gly | Ala | |
| 1 | | | 5 | | | | | 10 | | | | | 15 | | | |

| tgg | att | tgg | cac | aaa | ctg | aaa | ccg | gcc | ctg | gaa | cgt | gct | ggc | cac | aaa | 96 |
|---|---|---|---|---|---|---|---|---|---|---|---|---|---|---|---|---|
| Trp | Ile | Trp | His | Lys | Leu | Lys | Pro | Ala | Leu | Glu | Arg | Ala | Gly | His | Lys | |
| | | | 20 | | | | | 25 | | | | | 30 | | | |

| gtt | act | gca | ctg | gac | atg | gca | gcc | agt | ggc | att | gac | ccg | cgt | caa | att | 144 |
|---|---|---|---|---|---|---|---|---|---|---|---|---|---|---|---|---|
| Val | Thr | Ala | Leu | Asp | Met | Ala | Ala | Ser | Gly | Ile | Asp | Pro | Arg | Gln | Ile | |
| | 35 | | | | | 40 | | | | | 45 | | | | | |

| gaa | cag | atc | aac | tct | ttc | gat | gaa | tac | tct | gaa | ccg | ctg | ctg | act | ttc | 192 |
|---|---|---|---|---|---|---|---|---|---|---|---|---|---|---|---|---|
| Glu | Gln | Ile | Asn | Ser | Phe | Asp | Glu | Tyr | Ser | Glu | Pro | Leu | Leu | Thr | Phe | |
| | 50 | | | | | 55 | | | | | 60 | | | | | |

| ctg | gaa | aaa | ctg | ccg | caa | ggc | gaa | aag | gtt | atc | att | gtt | ggt | gaa | agc | 240 |
|---|---|---|---|---|---|---|---|---|---|---|---|---|---|---|---|---|
| Leu | Glu | Lys | Leu | Pro | Gln | Gly | Glu | Lys | Val | Ile | Ile | Val | Gly | Glu | Ser | |
| 65 | | | | | 70 | | | | | 75 | | | | | 80 | |

| tgt | gca | ggc | ctg | aac | att | gct | att | gct | gct | gat | cgt | tac | gtt | gac | aaa | 288 |
|---|---|---|---|---|---|---|---|---|---|---|---|---|---|---|---|---|
| Cys | Ala | Gly | Leu | Asn | Ile | Ala | Ile | Ala | Ala | Asp | Arg | Tyr | Val | Asp | Lys | |
| | | | | 85 | | | | | 90 | | | | | 95 | | |

| att | gca | gct | ggc | gtt | ttc | cac | aac | tcc | ctg | ctg | ccg | gac | acc | gtt | cac | 336 |
|---|---|---|---|---|---|---|---|---|---|---|---|---|---|---|---|---|
| Ile | Ala | Ala | Gly | Val | Phe | His | Asn | Ser | Leu | Leu | Pro | Asp | Thr | Val | His | |
| | | | 100 | | | | | 105 | | | | | 110 | | | |

| agc | ccg | tct | tac | act | gtt | gaa | aag | ctg | ctg | gaa | tcg | ttc | ccg | gac | tgg | 384 |
|---|---|---|---|---|---|---|---|---|---|---|---|---|---|---|---|---|
| Ser | Pro | Ser | Tyr | Thr | Val | Glu | Lys | Leu | Leu | Glu | Ser | Phe | Pro | Asp | Trp | |
| | 115 | | | | | 120 | | | | | 125 | | | | | |

| cgt | gac | aca | gaa | tat | ttc | acg | ttc | acc | aac | atc | act | ggc | gaa | acc | atc | 432 |
|---|---|---|---|---|---|---|---|---|---|---|---|---|---|---|---|---|
| Arg | Asp | Thr | Glu | Tyr | Phe | Thr | Phe | Thr | Asn | Ile | Thr | Gly | Glu | Thr | Ile | |
| | 130 | | | | | 135 | | | | | 140 | | | | | |

| act | acc | atg | aaa | ctg | ggt | ttc | gtt | ctg | ctg | cgt | gaa | aac | ctg | ttc | acc | 480 |
|---|---|---|---|---|---|---|---|---|---|---|---|---|---|---|---|---|
| Thr | Thr | Met | Lys | Leu | Gly | Phe | Val | Leu | Leu | Arg | Glu | Asn | Leu | Phe | Thr | |
| 145 | | | | | 150 | | | | | 155 | | | | | 160 | |

| aaa | tgc | act | gat | gaa | gaa | tat | gaa | ctg | gca | aaa | atg | gtt | atg | cgc | aag | 528 |
|---|---|---|---|---|---|---|---|---|---|---|---|---|---|---|---|---|
| Lys | Cys | Thr | Asp | Glu | Glu | Tyr | Glu | Leu | Ala | Lys | Met | Val | Met | Arg | Lys | |
| | | | | 165 | | | | | 170 | | | | | 175 | | |

| ggc | tct | ctg | ttc | caa | aac | gtt | ctg | gct | cag | cgt | ccg | aag | ttc | act | gaa | 576 |
|---|---|---|---|---|---|---|---|---|---|---|---|---|---|---|---|---|
| Gly | Ser | Leu | Phe | Gln | Asn | Val | Leu | Ala | Gln | Arg | Pro | Lys | Phe | Thr | Glu | |
| | | | 180 | | | | | 185 | | | | | 190 | | | |

| aaa | ggc | tac | ggc | tct | atc | aag | aaa | gtt | tat | att | tgg | acc | gat | caa | gac | 624 |
|---|---|---|---|---|---|---|---|---|---|---|---|---|---|---|---|---|
| Lys | Gly | Tyr | Gly | Ser | Ile | Lys | Lys | Val | Tyr | Ile | Trp | Thr | Asp | Gln | Asp | |
| | 195 | | | | | 200 | | | | | 205 | | | | | |

| aaa | ata | ttc | ctg | ccg | gac | ttc | caa | cgc | tgg | caa | att | gca | aac | tac | aaa | 672 |
|---|---|---|---|---|---|---|---|---|---|---|---|---|---|---|---|---|
| Lys | Ile | Phe | Leu | Pro | Asp | Phe | Gln | Arg | Trp | Gln | Ile | Ala | Asn | Tyr | Lys | |
| | 210 | | | | | 215 | | | | | 220 | | | | | |

| ccg | gac | aag | gtt | tat | cag | gtt | caa | ggc | ggc | gat | cac | aag | ctg | cag | ctg | 720 |
|---|---|---|---|---|---|---|---|---|---|---|---|---|---|---|---|---|
| Pro | Asp | Lys | Val | Tyr | Gln | Val | Gln | Gly | Gly | Asp | His | Lys | Leu | Gln | Leu | |
| 225 | | | | | 230 | | | | | 235 | | | | | 240 | |

| aca | aaa | act | gaa | gaa | gta | gct | cac | att | ctg | caa | gaa | gtt | gct | gat | gca | 768 |
|---|---|---|---|---|---|---|---|---|---|---|---|---|---|---|---|---|
| Thr | Lys | Thr | Glu | Glu | Val | Ala | His | Ile | Leu | Gln | Glu | Val | Ala | Asp | Ala | |
| | | | | 245 | | | | | 250 | | | | | 255 | | |

| tac | gct | taa | | | | | | | | | | | | | | 777 |
|---|---|---|---|---|---|---|---|---|---|---|---|---|---|---|---|---|
| Tyr | Ala | | | | | | | | | | | | | | | |

<210> SEQ ID NO 8
<211> LENGTH: 258
<212> TYPE: PRT

-continued

```
<213> ORGANISM: Manihot esculenta
<220> FEATURE:
<223> OTHER INFORMATION: Modified SHNL involving
      a replacement of Gly by Glu at position 165

<400> SEQUENCE: 8

Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
            20                  25                  30

Val Thr Ala Leu Asp Met Ala Ala Ser Gly Ile Asp Pro Arg Gln Ile
        35                  40                  45

Glu Gln Ile Asn Ser Phe Asp Glu Tyr Ser Glu Pro Leu Leu Thr Phe
    50                  55                  60

Leu Glu Lys Leu Pro Gln Gly Glu Lys Val Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
        115                 120                 125

Arg Asp Thr Glu Tyr Phe Thr Phe Thr Asn Ile Thr Gly Glu Thr Ile
    130                 135                 140

Thr Thr Met Lys Leu Gly Phe Val Leu Leu Arg Glu Asn Leu Phe Thr
145                 150                 155                 160

Lys Cys Thr Asp Glu Glu Tyr Glu Leu Ala Lys Met Val Met Arg Lys
                165                 170                 175

Gly Ser Leu Phe Gln Asn Val Leu Ala Gln Arg Pro Lys Phe Thr Glu
            180                 185                 190

Lys Gly Tyr Gly Ser Ile Lys Lys Val Tyr Ile Trp Thr Asp Gln Asp
        195                 200                 205

Lys Ile Phe Leu Pro Asp Phe Gln Arg Trp Gln Ile Ala Asn Tyr Lys
    210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
                245                 250                 255

Tyr Ala

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence:  primer

<400> SEQUENCE: 9
ggggaattca tggttactgc acacttcgtt ctgattcac                              39

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence:  primer

<400> SEQUENCE: 10
```

```
gggaagcttt taagcgtatg catcagcaac ttcttgcag                    39
```

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 11

```
ggggggggggc atatggttac tgcacacttc gttctgattc acac             44
```

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: primer

<400> SEQUENCE: 12

```
gggggatcct taagcgtatg catcagcaac ttcttgcag                    39
```

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 13

```
cgtgaaaacc tgttcaccaa atgcactgat gaagaatatg aactggcaaa aatg   54
```

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 14

```
cattttgcc agttcatatt cttcatcagt gcatttggtg aacaggtttt cacg    54
```

<210> SEQ ID NO 15
<211> LENGTH: 777
<212> TYPE: DNA
<213> ORGANISM: Manihot esculenta
<220> FEATURE:
<221> NAME/KEY: CDS
<222> LOCATION: (1)..(777)
<220> FEATURE:
<223> OTHER INFORMATION: cDNA coding for Modified SHNL involving
      a replacement of Val by Leu at position 173

<400> SEQUENCE: 15

```
atg gtt act gca cac ttc gtt ctg att cac acc att tgt cac ggc gca     48
Met Val Thr Ala His Phe Val Leu Ile His Thr Ile Cys His Gly Ala
1               5                   10                  15 tgg att tgg cac aaa ctg aaa ccg gcc ctg gaa cgt gct ggc cac aaa     96
Trp Ile Trp His Lys Leu Lys Pro Ala Leu Glu Arg Ala Gly His Lys
            20                  25                  30 gtt act gca ctg gac atg gca gcc agt ggc att gac ccg cgt caa att    144
Val Thr Ala Leu Asp Met Ala Ala Ser Gly Ile Asp Pro Arg Gln Ile
        35                  40                  45 gaa cag atc aac tct ttc gat gaa tac tct gaa ccg ctg ctg act ttc    192
Glu Gln Ile Asn Ser Phe Asp Glu Tyr Ser Glu Pro Leu Leu Thr Phe
    50                  55                  60
```

```
ctg gaa aaa ctg ccg caa ggc gaa aag gtt atc att gtt ggt gaa agc    240
Leu Glu Lys Leu Pro Gln Gly Glu Lys Val Ile Ile Val Gly Glu Ser
 65                  70                  75                  80 tgt gca ggc ctg aac att gct att gct gct gat cgt tac gtt gac aaa    288
Cys Ala Gly Leu Asn Ile Ala Ile Ala Ala Asp Arg Tyr Val Asp Lys
                 85                  90                  95 att gca gct ggc gtt ttc cac aac tcc ctg ctg ccg gac acc gtt cac    336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg    384
Ser Pro Ser Tyr Thr Val Glu Lys Leu Leu Glu Ser Phe Pro Asp Trp
        115                 120                 125 cgt gac aca gaa tat ttc acg ttc acc aac atc act ggc gaa acc atc    432
Arg Asp Thr Glu Tyr Phe Thr Phe Thr Asn Ile Thr Gly Glu Thr Ile
    130                 135                 140 act acc atg aaa ctg ggt ttc gtt ctg ctg cgt gaa aac ctg ttc acc    480
Thr Thr Met Lys Leu Gly Phe Val Leu Leu Arg Glu Asn Leu Phe Thr
145                 150                 155                 160 aaa tgc act gat ggc gaa tat gaa ctg gca aaa atg ctg atg cgc aag    528
Lys Cys Thr Asp Gly Glu Tyr Glu Leu Ala Lys Met Leu Met Arg Lys
                165                 170                 175 ggc tct ctg ttc caa aac gtt ctg gct cag cgt ccg aag ttc act gaa    576
Gly Ser Leu Phe Gln Asn Val Leu Ala Gln Arg Pro Lys Phe Thr Glu
            180                 185                 190 aaa ggc tac ggc tct atc aag aaa gtt tat att tgg acc gat caa gac    624
Lys Gly Tyr Gly Ser Ile Lys Lys Val Tyr Ile Trp Thr Asp Gln Asp
        195                 200                 205 aaa ata ttc ctg ccg gac ttc caa cgc tgg caa att gca aac tac aaa    672
Lys Ile Phe Leu Pro Asp Phe Gln Arg Trp Gln Ile Ala Asn Tyr Lys
    210                 215                 220 ccg gac aag gtt tat cag gtt caa ggc ggc gat cac aag ctg cag ctg    720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca    768
Thr Lys Thr Glu Glu Val Ala His Ile Leu Gln Glu Val Ala Asp Ala
                245                 250                 255 tac gct taa                                                        777
Tyr Ala

<210> SEQ ID NO 16
<211> LENGTH: 258
<212> TYPE: PRT
<213> ORGANISM: Manihot esculenta
<220> FEATURE:
<223> OTHER INFORMATION: Modified S

```
                85                  90                  95
Ile Ala Ala Gly Val Phe His Asn Ser Leu Leu Pro Asp Thr Val His
            100                 105                 110
Ser Pro Ser Tyr Thr Val Glu Lys Leu Leu Glu Ser Phe Pro Asp Trp
        115                 120                 125
Arg Asp Thr Glu Tyr Phe Thr Phe Thr Asn Ile Thr Gly Glu Thr Ile
    130                 135                 140
Thr Thr Met Lys Leu Gly Phe Val Leu Leu Arg Glu Asn Leu Phe Thr
145                 150                 155                 160
Lys Cys Thr Asp Gly Glu Tyr Glu Leu Ala Lys Met Leu Met Arg Lys
                165                 170                 175
Gly Ser Leu Phe Gln Asn Val Leu Ala Gln Arg Pro Lys Phe Thr Glu
            180                 185                 190
Lys Gly Tyr Gly Ser Ile Lys Lys Val Tyr Ile Trp Thr Asp Gln Asp
        195                 200                 205
Lys Ile Phe Leu Pro Asp Phe Gln Arg Trp Gln Ile Ala Asn Tyr Lys
    210                 215                 220
Pro Asp Lys Val Tyr Gln Val Gln Gly Gly Asp His Lys Leu Gln Leu
225                 230                 235                 240
Thr Lys Thr Glu Glu Val Ala His Ile Leu Gln Glu Val Ala Asp Ala
                245                 250                 255
Tyr Ala

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence:  primer
<220> FEATURE:
<221> NAME/KEY: misc_feature
<222> LOCATION: (25)..(27)
<223> OTHER INFORMATION: n is a, c, g, or t

<400> SEQUENCE: 17
ggcgaatatg aactggcaaa atgnnnatg cgcaagggct ctctg                45

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence:  primer
<220> FEATURE:
<221> NAME/KEY: misc_feature
<222> LOCATION: (19)..(21)
<223> OTHER INFORMATION: n is a, c, g, or t

<400> SEQUENCE: 18
cagagagccc ttgcgcatnn ncattttgc cagttcatat tcgcc                45

<210> SEQ ID NO 19
<211> LENGTH: 777
<212> TYPE: DNA
<213> ORGANISM: Manihot esculenta
<220> FEATURE:
<221> NAME/KEY: CDS
<222> LOCATION: (1)..(777)
<220> FEATURE:
<223> OTHER INFORMATION: cDNA coding for Modified SHNL involving
      a replacement of Met by Leu at position 174

<400> SEQUENCE: 19
```

```
atg gtt act gca cac ttc gtt ctg att cac acc att tgt cac ggc gca        48
Met Val Thr Ala His Phe Val Leu Ile His Thr Ile Cys His Gly Ala
1               5                   10                  15 tgg att tgg cac aaa ctg aaa ccg gcc ctg gaa cgt gct ggc cac aaa        96
Trp Ile Trp His Lys Leu Lys Pro Ala Leu Glu Arg Ala Gly His Lys
            20                  25                  30 gtt act gca ctg gac atg gca gcc agt ggc att gac ccg cgt caa att       144
Val Thr Ala Leu Asp Met Ala Ala Ser Gly Ile Asp Pro Arg Gln Ile
        35                  40                  45 gaa cag atc aac tct ttc gat gaa tac tct gaa ccg ctg ctg act ttc       192
Glu Gln Ile Asn Ser Phe Asp Glu Tyr Ser Glu Pro Leu Leu Thr Phe
    50                  55                  60 ctg gaa aaa ctg ccg caa ggc gaa aag gtt atc att gtt ggt gaa agc       240
Leu Glu Lys Leu Pro Gln Gly Glu Lys Val Ile Ile Val Gly Glu Ser
65                  70                  75                  80 tgt gca ggc ctg aac att gct att gct gct gat cgt tac gtt gac aaa       288
Cys Ala Gly Leu Asn Ile Ala Ile Ala Ala Asp Arg Tyr Val Asp Lys
                85                  90                  95 att gca gct ggc gtt ttc cac aac tcc ctg ctg ccg gac acc gtt cac       336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg       384
Ser Pro Ser Tyr Thr Val Glu Lys Leu Leu Glu Ser Phe Pro Asp Trp
        115                 120                 125 cgt gac aca gaa tat ttc acg ttc acc aac atc act ggc gaa acc atc       432
Arg Asp Thr Glu Tyr Phe Thr Phe Thr Asn Ile Thr Gly Glu Thr Ile
    130                 135                 140 act acc atg aaa ctg ggt ttc gtt ctg ctg cgt gaa aac ctg ttc acc       480
Thr Thr Met Lys Leu Gly Phe Val Leu Leu Arg Glu Asn Leu Phe Thr
145                 150                 155                 160 aaa tgc act gat ggc gaa tat gaa ctg gca aaa atg gtt ttg cgc aag       528
Lys Cys Thr Asp Gly Glu Tyr Glu Leu Ala Lys Met Val Leu Arg Lys
                165                 170                 175 ggc tct ctg ttc caa aac gtt ctg gct cag cgt ccg aag ttc act gaa       576
Gly Ser Leu Phe Gln Asn Val Leu Ala Gln Arg Pro Lys Phe Thr Glu
            180                 185                 190 aaa ggc tac ggc tct atc aag aaa gtt tat att tgg acc gat caa gac       624
Lys Gly Tyr Gly Ser Ile Lys Lys Val Tyr Ile Trp Thr Asp Gln Asp
        195                 200                 205 aaa ata ttc ctg ccg gac ttc caa cgc tgg caa att gca aac tac aaa       672
Lys Ile Phe Leu Pro Asp Phe Gln Arg Trp Gln Ile Ala Asn Tyr Lys
    210                 215                 220 ccg gac aag gtt tat cag gtt caa ggc ggc gat cac aag ctg cag ctg       720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca       768
Thr Lys Thr Glu Glu Val Ala His Ile Leu Gln Glu Val Ala Asp Ala
                245                 250                 255 tac gct taa                                                           777
Tyr Ala
```

<210> SEQ ID NO 20
<211> LENGTH: 258
<212> TYPE: PRT
<213> ORGANISM: Manihot esculenta
<220> FEATURE:
<223> OTHER INFORMATION: Modified SHNL involving
      a replacement of Met by Leu at position 174

<400> SEQUENCE: 20

```
Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
            20                  25                  30

Val Thr Ala Leu Asp Met Ala Ala Ser Gly Ile Asp Pro Arg Gln Ile
        35                  40                  45

Glu Gln Ile Asn Ser Phe Asp Glu Tyr Ser Glu Pro Leu Leu Thr Phe
    50                  55                  60

Leu Glu Lys Leu Pro Gln Gly Glu Lys Val Ile Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
        115                 120                 125

Arg Asp Thr Glu Tyr Phe Thr Phe Thr Asn Ile Thr Gly Glu Thr Ile
    130                 135                 140

Thr Thr Met Lys Leu Gly Phe Val Leu Leu Arg Glu Asn Leu Phe Thr
145                 150                 155                 160

Lys Cys Thr Asp Gly Glu Tyr Glu Leu Ala Lys Met Val Leu Arg Lys
                165                 170                 175

Gly Ser Leu Phe Gln Asn Val Leu Ala Gln Arg Pro Lys Phe Thr Glu
            180                 185                 190

Lys Gly Tyr Gly Ser Ile Lys Lys Val Tyr Ile Trp Thr Asp Gln Asp
        195                 200                 205

Lys Ile Phe Leu Pro Asp Phe Gln Arg Trp Gln Ile Ala Asn Tyr Lys
    210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
                245                 250                 255

Tyr Ala

<210> SEQ ID NO 21
<211> LENGTH: 777
<212> TYPE: DNA
<213> ORGANISM: Manihot esculenta
<220> FEATURE:
<221> NAME/KEY: CDS
<222> LOCATION: (1)..(777)
<220> FEATURE:
<223> OTHER INFORMATION: cDNA coding for Modified SHNL(SHNL
      Actmt022-G12) involving a replacement of Lys by Asn at position 21

<400> SEQUENCE: 21 atg gtt act gca cac ttc gtt ctg att cac acc att tgt cac ggc gca      48
Met Val Thr Ala His Phe Val Leu Ile His Thr Ile Cys His Gly Ala
1               5                   10                  15 tgg att tgg cac aat ctg aaa ccg gcc ctg gaa cgt gct ggc cac aaa      96
Trp Ile Trp His Asn Leu Lys Pro Ala Leu Glu Arg Ala Gly His Lys
            20                  25                  30 gtt act gca ctg gac atg gca gcc agt ggc att gac ccg cgt caa att     144
Val Thr Ala Leu Asp Met Ala Ala Ser Gly Ile Asp Pro Arg Gln Ile
        35                  40                  45 gaa cag atc aac tct ttc gat gaa tac tct gaa ccg ctg ctg act ttc     192
Glu Gln Ile Asn Ser Phe Asp Glu Tyr Ser Glu Pro Leu Leu Thr Phe
    50                  55                  60
```

```
ctg gaa aaa ctg ccg caa ggc gaa aag gtt atc att gtt ggt gaa agc    240
Leu Glu Lys Leu Pro Gln Gly Glu Lys Val Ile Ile Val Gly Glu Ser
 65                  70                  75                  80 tgt gca ggc ctg aac att gct att gct gct gat cgt tac gtt gac aaa    288
Cys Ala Gly Leu Asn Ile Ala Ile Ala Ala Asp Arg Tyr Val Asp Lys
                 85                  90                  95 att gca gct ggc gtt ttc cac aac tcc ctg ctg ccg gac acc gtt cac    336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg    384
Ser Pro Ser Tyr Thr Val Glu Lys Leu Leu Glu Ser Phe Pro Asp Trp
        115                 120                 125 cgt gac aca gaa tat ttc acg ttc acc aac atc act ggc gaa acc atc    432
Arg Asp Thr Glu Tyr Phe Thr Phe Thr Asn Ile Thr Gly Glu Thr Ile
    130                 135                 140 act acc atg aaa ctg ggt ttc gtt ctg ctg cgt gaa aac ctg ttc acc    480
Thr Thr Met Lys Leu Gly Phe Val Leu Leu Arg Glu Asn Leu Phe Thr
145                 150                 155                 160 aaa tgc act gat ggc gaa tat gaa ctg gca aaa atg gtt atg cgc aag    528
Lys Cys Thr Asp Gly Glu Tyr Glu Leu Ala Lys Met Val Met Arg Lys
                165                 170                 175 ggc tct ctg ttc caa aac gtt ctg gct cag cgt ccg aag ttc act gaa    576
Gly Ser Leu Phe Gln Asn Val Leu Ala Gln Arg Pro Lys Phe Thr Glu
            180                 185                 190 aaa ggc tac ggc tct atc aag aaa gtt tat att tgg acc gat caa gac    624
Lys Gly Tyr Gly Ser Ile Lys Lys Val Tyr Ile Trp Thr Asp Gln Asp
        195                 200                 205 aaa ata ttc ctg ccg gac ttc caa cgc tgg caa att gca aac tac aaa    672
Lys Ile Phe Leu Pro Asp Phe Gln Arg Trp Gln Ile Ala Asn Tyr Lys
    210                 215                 220 ccg gac aag gtt tat cag gtt caa ggc ggc gat cac aag ctg cag ctg    720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca    768
Thr Lys Thr Glu Glu Val Ala His Ile Leu Gln Glu Val Ala Asp Ala
                245                 250                 255 tac gct taa                                                        777
Tyr Ala

<210> SEQ ID NO 22
<211> LENGTH: 258
<212> TYPE: PRT
<213> ORGANISM: Manihot esculenta
<220> FEATURE:
<223> OTHER INFORMATION: Modified SHNL(SHNL Actmt022-G12) involving
      a replacement of Lys by Asn at position 21

<400> SEQUENCE: 22

Met Val Thr Ala His Phe Val Leu Ile His Thr Ile Cys His Gly Ala
 1               5                  10                  15

Trp Ile Trp His Asn Leu Lys Pro Ala Leu Glu Arg Ala Gly His Lys
                20                  25                  30

Val Thr Ala Leu Asp Met Ala Ala Ser Gly Ile Asp Pro Arg Gln Ile
            35                  40                  45

Glu Gln Ile Asn Ser Phe Asp Glu Tyr Ser Glu Pro Leu Leu Thr Phe
        50                  55                  60

Leu Glu Lys Leu Pro Gln Gly Glu Lys Val Ile Ile Val Gly Glu Ser
 65                  70                  75                  80

Cys Ala Gly Leu Asn Ile Ala Ile Ala Ala Asp Arg Tyr Val Asp Lys
```

-continued

```
                    85                  90                  95
Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
        115                 120                 125

Arg Asp Thr Glu Tyr Phe Thr Phe Thr Asn Ile Thr Gly Glu Thr Ile
    130                 135                 140

Thr Thr Met Lys Leu Gly Phe Val Leu Leu Arg Glu Asn Leu Phe Thr
145                 150                 155                 160

Lys Cys Thr Asp Gly Glu Tyr Glu Leu Ala Lys Met Val Met Arg Lys
                165                 170                 175

Gly Ser Leu Phe Gln Asn Val Leu Ala Gln Arg Pro Lys Phe Thr Glu
            180                 185                 190

Lys Gly Tyr Gly Ser Ile Lys Lys Val Tyr Ile Trp Thr Asp Gln Asp
        195                 200                 205

Lys Ile Phe Leu Pro Asp Phe Gln Arg Trp Gln Ile Ala Asn Tyr Lys
    210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
                245                 250                 255

Tyr Ala

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (19)..(21)
<223> OTHER INFORMATION: n is a, c, g, or t

<400> SEQUENCE: 23
ggcgcatgga tttggcacnn nctgaaaccg gccctggaa                          39

<210> SEQ ID NO 24
<211> LENGTH: 39
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (19)..(21)
<223> OTHER INFORMATION: n is a, c, g, or t

<400> SEQUENCE: 24
ttccagggcc ggtttcagnn ngtgccaaat ccatgcgcc                          39

<210> SEQ ID NO 25
<211> LENGTH: 777
<212> TYPE: DNA
<213> ORGANISM: Manihot esculenta
<220> FEATURE:
<221> NAME/KEY: CDS
<222> LOCATION: (1)..(777)
<220> FEATURE:
<223> OTHER INFORMATION: cDNA coding for Modified SHNL involving
      a replacement of Lys by Glu at position 21

<400> SEQUENCE: 25
```

```
atg gtt act gca cac ttc gtt ctg att cac acc att tgt cac ggc gca       48
Met Val Thr Ala His Phe Val Leu Ile His Thr Ile Cys His Gly Ala
 1               5                  10                  15 tgg att tgg cac gaa ctg aaa ccg gcc ctg gaa cgt gct ggc cac aaa       96
Trp Ile Trp His Glu Leu Lys Pro Ala Leu Glu Arg Ala Gly His Lys
                20                  25                  30 gtt act gca ctg gac atg gca gcc agt ggc att gac ccg cgt caa att      144
Val Thr Ala Leu Asp Met Ala Ala Ser Gly Ile Asp Pro Arg Gln Ile
         35                  40                  45 gaa cag atc aac tct ttc gat gaa tac tct gaa ccg ctg ctg act ttc      192
Glu Gln Ile Asn Ser Phe Asp Glu Tyr Ser Glu Pro Leu Leu Thr Phe
     50                  55                  60 ctg gaa aaa ctg ccg caa ggc gaa aag gtt atc att gtt ggt gaa agc      240
Leu Glu Lys Leu Pro Gln Gly Glu Lys Val Ile Ile Val Gly Glu Ser
 65                  70                  75                  80 tgt gca ggc ctg aac att gct att gct gct gat cgt tac gtt gac aaa      288
Cys Ala Gly Leu Asn Ile Ala Ile Ala Ala Asp Arg Tyr Val Asp Lys
                 85                  90                  95 att gca gct ggc gtt ttc cac aac tcc ctg ctg ccg gac acc gtt cac      336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg      384
Ser Pro Ser Tyr Thr Val Glu Lys Leu Leu Glu Ser Phe Pro Asp Trp
        115                 120                 125 cgt gac aca gaa tat ttc acg ttc acc aac atc act ggc gaa acc atc      432
Arg Asp Thr Glu Tyr Phe Thr Phe Thr Asn Ile Thr Gly Glu Thr Ile
    130                 135                 140 act acc atg aaa ctg ggt ttc gtt ctg ctg cgt gaa aac ctg ttc acc      480
Thr Thr Met Lys Leu Gly Phe Val Leu Leu Arg Glu Asn Leu Phe Thr
145                 150                 155                 160 aaa tgc act gat ggc gaa tat gaa ctg gca aaa atg gtt atg cgc aag      528
Lys Cys Thr Asp Gly Glu Tyr Glu Leu Ala Lys Met Val Met Arg Lys
                165                 170                 175 ggc tct ctg ttc caa aac gtt ctg gct cag cgt ccg aag ttc act gaa      576
Gly Ser Leu Phe Gln Asn Val Leu Ala Gln Arg Pro Lys Phe Thr Glu
            180                 185                 190 aaa ggc tac ggc tct atc aag aaa gtt tat att tgg acc gat caa gac      624
Lys Gly Tyr Gly Ser Ile Lys Lys Val Tyr Ile Trp Thr Asp Gln Asp
        195                 200                 205 aaa ata ttc ctg ccg gac ttc caa cgc tgg caa att gca aac tac aaa      672
Lys Ile Phe Leu Pro Asp Phe Gln Arg Trp Gln Ile Ala Asn Tyr Lys
    210                 215                 220 ccg gac aag gtt tat cag gtt caa ggc ggc gat cac aag ctg cag ctg      720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca      768
Thr Lys Thr Glu Glu Val Ala His Ile Leu Gln Glu Val Ala Asp Ala
                245                 250                 255 tac gct taa                                                          777
Tyr Ala <210> SEQ ID NO 26
<211> LENGTH: 258
<212> TYPE: PRT
<213> ORGANISM: Manihot esculenta
<220> FEATURE:
<223> OTHER INFORMATION: Modified SHNL involving
      a replacement of Lys by Glu at position 21

<400> SEQUENCE: 26
```

```
Met Val Thr Ala His Phe Val Leu Ile His Thr Ile Cys His Gly Ala
1               5                   10                  15

Trp Ile Trp His Glu Leu Lys Pro Ala Leu Glu Arg Ala Gly His Lys
            20                  25                  30

Val Thr Ala Leu Asp Met Ala Ala Ser Gly Ile Asp Pro Arg Gln Ile
        35                  40                  45

Glu Gln Ile Asn Ser Phe Asp Glu Tyr Ser Glu Pro Leu Leu Thr Phe
    50                  55                  60

Leu Glu Lys Leu Pro Gln Gly Glu Lys Val Ile Ile Val Gly Glu Ser
65              70                  75                  80

Cys Ala Gly Leu Asn Ile Ala Ile Ala Ala Asp Arg Tyr Val Asp Lys
            85                  90                  95

Ile Ala Ala Gly Val Phe His Asn Ser Leu Leu Pro Asp Thr Val His
        100                 105                 110

Ser Pro Ser Tyr Thr Val Glu Lys Leu Leu Glu Ser Phe Pro Asp Trp
    115                 120                 125

Arg Asp Thr Glu Tyr Phe Thr Phe Thr Asn Ile Thr Gly Glu Thr Ile
130                 135                 140

Thr Thr Met Lys Leu Gly Phe Val Leu Leu Arg Glu Asn Leu Phe Thr
145                 150                 155                 160

Lys Cys Thr Asp Gly Glu Tyr Glu Leu Ala Lys Met Val Met Arg Lys
            165                 170                 175

Gly Ser Leu Phe Gln Asn Val Leu Ala Gln Arg Pro Lys Phe Thr Glu
        180                 185                 190

Lys Gly Tyr Gly Ser Ile Lys Lys Val Tyr Ile Trp Thr Asp Gln Asp
    195                 200                 205

Lys Ile Phe Leu Pro Asp Phe Gln Arg Trp Gln Ile Ala Asn Tyr Lys
210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
            245                 250                 255

Tyr Ala

<210> SEQ ID NO 27
<211> LENGTH: 777
<212> TYPE: DNA
<213> ORGANISM: Manihot esculenta
<220> FEATURE:
<221> NAME/KEY: CDS
<222> LOCATION: (1)..(777)
<220> FEATURE:
<223> OTHER INFORMATION: cDNA coding for Modified SHNL involving
      a replacement of Lys by Asp at position 21

<400> SEQUENCE: 27 atg gtt act gca cac ttc gtt ctg att cac acc att tgt cac ggc gca      48
Met Val Thr Ala His Phe Val Leu Ile His Thr Ile Cys His Gly Ala
1               5                   10                  15 tgg att tgg cac gac ctg aaa ccg gcc ctg gaa cgt gct ggc cac aaa      96
Trp Ile Trp His Asp Leu Lys Pro Ala Leu Glu Arg Ala Gly His Lys
            20                  25                  30 gtt act gca ctg gac atg gca gcc agt ggc att gac ccg cgt caa att    144
Val Thr Ala Leu Asp Met Ala Ala Ser Gly Ile Asp Pro Arg Gln Ile
        35                  40                  45 gaa cag atc aac tct ttc gat gaa tac tct gaa ccg ctg ctg act ttc    192
Glu Gln Ile Asn Ser Phe Asp Glu Tyr Ser Glu Pro Leu Leu Thr Phe
    50                  55                  60
```

```
ctg gaa aaa ctg ccg caa ggc gaa aag gtt atc att gtt ggt gaa agc    240
Leu Glu Lys Leu Pro Gln Gly Glu Lys Val Ile Ile Val Gly Glu Ser
 65                  70                  75                  80 tgt gca ggc ctg aac att gct att gct gct gat cgt tac gtt gac aaa    288
Cys Ala Gly Leu Asn Ile Ala Ile Ala Ala Asp Arg Tyr Val Asp Lys
                 85                  90                  95 att gca gct ggc gtt ttc cac aac tcc ctg ctg ccg gac acc gtt cac    336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg    384
Ser Pro Ser Tyr Thr Val Glu Lys Leu Leu Glu Ser Phe Pro Asp Trp
        115                 120                 125 cgt gac aca gaa tat ttc acg ttc acc aac atc act ggc gaa acc atc    432
Arg Asp Thr Glu Tyr Phe Thr Phe Thr Asn Ile Thr Gly Glu Thr Ile
    130                 135                 140 act acc atg aaa ctg ggt ttc gtt ctg ctg cgt gaa aac ctg ttc acc    480
Thr Thr Met Lys Leu Gly Phe Val Leu Leu Arg Glu Asn Leu Phe Thr
145                 150                 155                 160 aaa tgc act gat ggc gaa tat gaa ctg gca aaa atg gtt atg cgc aag    528
Lys Cys Thr Asp Gly Glu Tyr Glu Leu Ala Lys Met Val Met Arg Lys
                165                 170                 175 ggc tct ctg ttc caa aac gtt ctg gct cag cgt ccg aag ttc act gaa    576
Gly Ser Leu Phe Gln Asn Val Leu Ala Gln Arg Pro Lys Phe Thr Glu
            180                 185                 190 aaa ggc tac ggc tct atc aag aaa gtt tat att tgg acc gat caa gac    624
Lys Gly Tyr Gly Ser Ile Lys Lys Val Tyr Ile Trp Thr Asp Gln Asp
        195                 200                 205 aaa ata ttc ctg ccg gac ttc caa cgc tgg caa att gca aac tac aaa    672
Lys Ile Phe Leu Pro Asp Phe Gln Arg Trp Gln Ile Ala Asn Tyr Lys
    210                 215                 220 ccg gac aag gtt tat cag gtt caa ggc ggc gat cac aag ctg cag ctg    720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca    768
Thr Lys Thr Glu Glu Val Ala His Ile Leu Gln Glu Val Ala Asp Ala
                245                 250                 255 tac gct taa                                                        777
Tyr Ala

<210> SEQ ID NO 28
<211> LENGTH: 258
<212> TYPE: PRT
<213> ORGANISM: Manihot esculenta
<220> FEATURE:
<223> OTHER INFORMATION: Modified SHNL involving
      a replacement of Lys by Asp at position 21

<400> SEQUENCE: 28

Met Val Thr Ala His Phe Val Leu Ile His Thr Ile Cys His Gly Ala
1               5                   10                  15

Trp Ile Trp His Asp Leu Lys Pro Ala Leu Glu Arg Ala Gly His Lys
            20                  25                  30

Val Thr Ala Leu Asp Met Ala Ala Ser Gly Ile Asp Pro Arg Gln Ile
        35                  40                  45

Glu Gln Ile Asn Ser Phe Asp Glu Tyr Ser Glu Pro Leu Leu Thr Phe
    50                  55                  60

Leu Glu Lys Leu Pro Gln Gly Glu Lys Val Ile Ile Val Gly Glu Ser
65                  70                  75                  80

Cys Ala Gly Leu Asn Ile Ala Ile Ala Ala Asp Arg Tyr Val Asp Lys
```

```
                    85                  90                  95
Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
        115                 120                 125

Arg Asp Thr Glu Tyr Phe Thr Phe Thr Asn Ile Thr Gly Glu Thr Ile
    130                 135                 140

Thr Thr Met Lys Leu Gly Phe Val Leu Leu Arg Glu Asn Leu Phe Thr
145                 150                 155                 160

Lys Cys Thr Asp Gly Glu Tyr Glu Leu Ala Lys Met Val Met Arg Lys
            165                 170                 175

Gly Ser Leu Phe Gln Asn Val Leu Ala Gln Arg Pro Lys Phe Thr Glu
        180                 185                 190

Lys Gly Tyr Gly Ser Ile Lys Lys Val Tyr Ile Trp Thr Asp Gln Asp
    195                 200                 205

Lys Ile Phe Leu Pro Asp Phe Gln Arg Trp Gln Ile Ala Asn Tyr Lys
210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
            245                 250                 255

Tyr Ala

<210> SEQ ID NO 29
<211> LENGTH: 777
<212> TYPE: DNA
<213> ORGANISM: Manihot esculenta
<220> FEATURE:
<221> NAME/KEY: CDS
<222> LOCATION: (1)..(777)
<220> FEATURE:
<223> OTHER INFORMATION: cDNA coding for Modified SHNL involving
      a replacement of Lys by Asn at position 21

<400> SEQUENCE: 29 atg gtt act gca cac ttc gtt ctg att cac acc att tgt cac ggc gca    48
Met Val Thr Ala His Phe Val Leu Ile His Thr Ile Cys His Gly Ala
1               5                   10                  15 tgg att tgg cac aac ctg aaa ccg gcc ctg gaa cgt gct ggc cac aaa    96
Trp Ile Trp His Asn Leu Lys Pro Ala Leu Glu Arg Ala Gly His Lys
            20                  25                  30 gtt act gca ctg gac atg gca gcc agt ggc att gac ccg cgt caa att   144
Val Thr Ala Leu Asp Met Ala Ala Ser Gly Ile Asp Pro Arg Gln Ile
        35                  40                  45 gaa cag atc aac tct ttc gat gaa tac tct gaa ccg ctg ctg act ttc   192
Glu Gln Ile Asn Ser Phe Asp Glu Tyr Ser Glu Pro Leu Leu Thr Phe
    50                  55                  60 ctg gaa aaa ctg ccg caa ggc gaa aag gtt atc att gtt ggt gaa agc   240
Leu Glu Lys Leu Pro Gln Gly Glu Lys Val Ile Ile Val Gly Glu Ser
65                  70                  75                  80 tgt gca ggc ctg aac att gct att gct gct gat cgt tac gtt gac aaa   288
Cys Ala Gly Leu Asn Ile Ala Ile Ala Ala Asp Arg Tyr Val Asp Lys
            85                  90                  95 att gca gct ggc gtt ttc cac aac tcc ctg ctg ccg gac acc gtt cac   336
Ile Ala Ala Gly Val Phe His Asn Ser Leu Leu Pro Asp Thr Val His
        100                 105                 110 agc ccg tct tac act gtt gaa aag ctg ctg gaa tcg ttc ccg gac tgg   384
Ser Pro Ser Tyr Thr Val Glu Lys Leu Leu Glu Ser Phe Pro Asp Trp
    115                 120                 125
```

-continued

```
cgt gac aca gaa tat ttc acg ttc acc aac atc act ggc gaa acc atc        432
Arg Asp Thr Glu Tyr Phe Thr Phe Thr Asn Ile Thr Gly Glu Thr Ile
130                 135                 140 act acc atg aaa ctg ggt ttc gtt ctg ctg cgt gaa aac ctg ttc acc        480
Thr Thr Met Lys Leu Gly Phe Val Leu Leu Arg Glu Asn Leu Phe Thr
145                 150                 155                 160 aaa tgc act gat ggc gaa tat gaa ctg gca aaa atg gtt atg cgc aag        528
Lys Cys Thr Asp Gly Glu Tyr Glu Leu Ala Lys Met Val Met Arg Lys
                165                 170                 175 ggc tct ctg ttc caa aac gtt ctg gct cag cgt ccg aag ttc act gaa        576
Gly Ser Leu Phe Gln Asn Val Leu Ala Gln Arg Pro Lys Phe Thr Glu
            180                 185                 190 aaa ggc tac ggc tct atc aag aaa gtt tat att tgg acc gat caa gac        624
Lys Gly Tyr Gly Ser Ile Lys Lys Val Tyr Ile Trp Thr Asp Gln Asp
        195                 200                 205 aaa ata ttc ctg ccg gac ttc caa cgc tgg caa att gca aac tac aaa        672
Lys Ile Phe Leu Pro Asp Phe Gln Arg Trp Gln Ile Ala Asn Tyr Lys
    210                 215                 220 ccg gac aag gtt tat cag gtt caa ggc ggc gat cac aag ctg cag ctg        720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca        768
Thr Lys Thr Glu Glu Val Ala His Ile Leu Gln Glu Val Ala Asp Ala
                245                 250                 255 tac gct taa                                                            777
Tyr Ala
```

<210> SEQ ID NO 30
<211> LENGTH: 258
<212> TYPE: PRT
<213> ORGANISM: Manihot esculenta
<220> FEATURE:
<223> OTHER INFORMATION: Modified SHNL involving
      a replacement of Lys by Asn at position 21

<400> SEQUENCE: 30

```
Met Val Thr Ala His Phe Val Leu Ile His Thr Ile Cys His Gly Ala
1               5                   10                  15

Trp Ile Trp His Asn Leu Lys Pro Ala Leu Glu Arg Ala Gly His Lys
            20                  25                  30

Val Thr Ala Leu Asp Met Ala Ala Ser Gly Ile Asp Pro Arg Gln Ile
        35                  40                  45

Glu Gln Ile Asn Ser Phe Asp Glu Tyr Ser Glu Pro Leu Leu Thr Phe
    50                  55                  60

Leu Glu Lys Leu Pro Gln Gly Glu Lys Val Ile Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
        115                 120                 125

Arg Asp Thr Glu Tyr Phe Thr Phe Thr Asn Ile Thr Gly Glu Thr Ile
    130                 135                 140

Thr Thr Met Lys Leu Gly Phe Val Leu Leu Arg Glu Asn Leu Phe Thr
145                 150                 155                 160

Lys Cys Thr Asp Gly Glu Tyr Glu Leu Ala Lys Met Val Met Arg Lys
                165                 170                 175
```

```
Gly Ser Leu Phe Gln Asn Val Leu Ala Gln Arg Pro Lys Phe Thr Glu
            180                 185                 190

Lys Gly Tyr Gly Ser Ile Lys Lys Val Tyr Ile Trp Thr Asp Gln Asp
        195                 200                 205

Lys Ile Phe Leu Pro Asp Phe Gln Arg Trp Gln Ile Ala Asn Tyr Lys
    210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
            245                 250                 255

Tyr Ala

<210> SEQ ID NO 31
<211> LENGTH: 777
<212> TYPE: DNA
<213> ORGANISM: Manihot esculenta
<220> FEATURE:
<221> NAME/KEY: CDS
<222> LOCATION: (1)..(777)
<220> FEATURE:
<223> OTHER INFORMATION: cDNA coding for Modified SHNL involving
      replacement of Gly by Glu at position 165 and Val by Leu at
      position 173

<400> SEQUENCE: 31 atg gtt act gca cac ttc gtt ctg att cac acc att tgt cac ggc gca      48
Met Val Thr Ala His Phe Val Leu Ile His Thr Ile Cys His Gly Ala
1               5                   10                  15 tgg att tgg cac aaa ctg aaa ccg gcc ctg gaa cgt gct ggc cac aaa      96
Trp Ile Trp His Lys Leu Lys Pro Ala Leu Glu Arg Ala Gly His Lys
            20                  25                  30 gtt act gca ctg gac atg gca gcc agt ggc att gac ccg cgt caa att     144
Val Thr Ala Leu Asp Met Ala Ala Ser Gly Ile Asp Pro Arg Gln Ile
        35                  40                  45 gaa cag atc aac tct ttc gat gaa tac tct gaa ccg ctg ctg act ttc     192
Glu Gln Ile Asn Ser Phe Asp Glu Tyr Ser Glu Pro Leu Leu Thr Phe
    50                  55                  60 ctg gaa aaa ctg ccg caa ggc gaa aag gtt atc att gtt ggt gaa agc     240
Leu Glu Lys Leu Pro Gln Gly Glu Lys Val Ile Ile Val Gly Glu Ser
65                  70                  75                  80 tgt gca ggc ctg aac att gct att gct gct gat cgt tac gtt gac aaa     288
Cys Ala Gly Leu Asn Ile Ala Ile Ala Ala Asp Arg Tyr Val Asp Lys
                85                  90                  95 att gca gct ggc gtt ttc cac aac tcc ctg ctg ccg gac acc gtt cac     336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg     384
Ser Pro Ser Tyr Thr Val Glu Lys Leu Leu Glu Ser Phe Pro Asp Trp
        115                 120                 125 cgt gac aca gaa tat ttc acg ttc acc aac atc act ggc gaa acc atc     432
Arg Asp Thr Glu Tyr Phe Thr Phe Thr Asn Ile Thr Gly Glu Thr Ile
    130                 135                 140 act acc atg aaa ctg ggt ttc gtt ctg ctg cgt gaa aac ctg ttc acc     480
Thr Thr Met Lys Leu Gly Phe Val Leu Leu Arg Glu Asn Leu Phe Thr
145                 150                 155                 160 aaa tgc act gat gaa gaa tat gaa ctg gca aaa atg ctg atg cgc aag     528
Lys Cys Thr Asp Glu Glu Tyr Glu Leu Ala Lys Met Leu Met Arg Lys
                165                 170                 175 ggc tct ctg ttc caa aac gtt ctg gct cag cgt ccg aag ttc act gaa     576
Gly Ser Leu Phe Gln Asn Val Leu Ala Gln Arg Pro Lys Phe Thr Glu
```

```
                180              185              190
aaa ggc tac ggc tct atc aag aaa gtt tat att tgg acc gat caa gac    624
Lys Gly Tyr Gly Ser Ile Lys Lys Val Tyr Ile Trp Thr Asp Gln Asp
        195              200              205 aaa ata ttc ctg ccg gac ttc caa cgc tgg caa att gca aac tac aaa    672
Lys Ile Phe Leu Pro Asp Phe Gln Arg Trp Gln Ile Ala Asn Tyr Lys
210              215              220 ccg gac aag gtt tat cag gtt caa ggc ggc gat cac aag ctg cag ctg    720
Pro Asp Lys Val Tyr Gln Val Gln Gly Gly Asp His Lys Leu Gln Leu
225              230              235              240 aca aaa act gaa gaa gta gct cac att ctg caa gaa gtt gct gat gca    768
Thr Lys Thr Glu Glu Val Ala His Ile Leu Gln Glu Val Ala Asp Ala
            245              250              255 tac gct taa                                                        777
Tyr Ala

<210> SEQ ID NO 32
<211> LENGTH: 258
<212> TYPE: PRT
<213> ORGANISM: Manihot esculenta
<220> FEATURE:
<223> OTHER INFORMATION: Modified SHNL involving
      replacement of Gly by Glu at position 165 and Val by Leu at
      position 173

<400> SEQUENCE: 32

Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
            20                  25                  30

Val Thr Ala Leu Asp Met Ala Ala Ser Gly Ile Asp Pro Arg Gln Ile
        35                  40                  45

Glu Gln Ile Asn Ser Phe Asp Glu Tyr Ser Glu Pro Leu Leu Thr Phe
    50                  55                  60

Leu Glu Lys Leu Pro Gln Gly Glu Lys Val Ile Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
        115                 120                 125

Arg Asp Thr Glu Tyr Phe Thr Phe Thr Asn Ile Thr Gly Glu Thr Ile
    130                 135                 140

Thr Thr Met Lys Leu Gly Phe Val Leu Leu Arg Glu Asn Leu Phe Thr
145                 150                 155                 160

Lys Cys Thr Asp Glu Glu Tyr Glu Leu Ala Lys Met Leu Met Arg Lys
                165                 170                 175

Gly Ser Leu Phe Gln Asn Val Leu Ala Gln Arg Pro Lys Phe Thr Glu
            180                 185                 190

Lys Gly Tyr Gly Ser Ile Lys Lys Val Tyr Ile Trp Thr Asp Gln Asp
        195                 200                 205

Lys Ile Phe Leu Pro Asp Phe Gln Arg Trp Gln Ile Ala Asn Tyr Lys
    210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
```

245                 250                 255
Tyr Ala

<210> SEQ ID NO 33
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 33
tatgaactgg caaaaatgct gctgcgcaag ggctctctgt tc        42

<210> SEQ ID NO 34
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 34
gaacagagag cccttgcgca gcagcatttt tgccagttca ta        42

<210> SEQ ID NO 35
<211> LENGTH: 777
<212> TYPE: DNA
<213> ORGANISM: Manihot esculenta
<220> FEATURE:
<221> NAME/KEY: CDS
<222> LOCATION: (1)..(777)
<220> FEATURE:
<223> OTHER INFORMATION: cDNA coding for Modified SHNL involving
      replacement of Gly by Glu at position 165 and Val by Leu at
      position 173 and Met by Leu at position 174

<400> SEQUENCE: 35

```
atg gtt act gca cac ttc gtt ctg att cac acc att tgt cac ggc gca      48
Met Val Thr Ala His Phe Val Leu Ile His Thr Ile Cys His Gly Ala
1               5                   10                  15 tgg att tgg cac aaa ctg aaa ccg gcc ctg gaa cgt gct ggc cac aaa      96
Trp Ile Trp His Lys Leu Lys Pro Ala Leu Glu Arg Ala Gly His Lys
            20                  25                  30 gtt act gca ctg gac atg gca gcc agt ggc att gac ccg cgt caa att    144
Val Thr Ala Leu Asp Met Ala Ala Ser Gly Ile Asp Pro Arg Gln Ile
        35                  40                  45 gaa cag atc aac tct ttc gat gaa tac tct gaa ccg ctg ctg act ttc    192
Glu Gln Ile Asn Ser Phe Asp Glu Tyr Ser Glu Pro Leu Leu Thr Phe
    50                  55                  60 ctg gaa aaa ctg ccg caa ggc gaa aag gtt atc att gtt ggt gaa agc    240
Leu Glu Lys Leu Pro Gln Gly Glu Lys Val Ile Ile Val Gly Glu Ser
65                  70                  75                  80 tgt gca ggc ctg aac att gct att gct gct gat cgt tac gtt gac aaa    288
Cys Ala Gly Leu Asn Ile Ala Ile Ala Ala Asp Arg Tyr Val Asp Lys
                85                  90                  95 att gca gct ggc gtt ttc cac aac tcc ctg ctg ccg gac acc gtt cac    336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg    384
Ser Pro Ser Tyr Thr Val Glu Lys Leu Leu Glu Ser Phe Pro Asp Trp
        115                 120                 125 cgt gac aca gaa tat ttc acg ttc acc aac atc act ggc gaa acc atc    432
Arg Asp Thr Glu Tyr Phe Thr Phe Thr Asn Ile Thr Gly Glu Thr Ile
    130                 135                 140
```

```
act acc atg aaa ctg ggt ttc gtt ctg ctg cgt gaa aac ctg ttc acc      480
Thr Thr Met Lys Leu Gly Phe Val Leu Leu Arg Glu Asn Leu Phe Thr
145                 150                 155                 160 aaa tgc act gat gaa gaa tat gaa ctg gca aaa atg ctg ctg cgc aag      528
Lys Cys Thr Asp Glu Glu Tyr Glu Leu Ala Lys Met Leu Leu Arg Lys
            165                 170                 175 ggc tct ctg ttc caa aac gtt ctg gct cag cgt ccg aag ttc act gaa      576
Gly Ser Leu Phe Gln Asn Val Leu Ala Gln Arg Pro Lys Phe Thr Glu
        180                 185                 190 aaa ggc tac ggc tct atc aag aaa gtt tat att tgg acc gat caa gac      624
Lys Gly Tyr Gly Ser Ile Lys Lys Val Tyr Ile Trp Thr Asp Gln Asp
    195                 200                 205 aaa ata ttc ctg ccg gac ttc caa cgc tgg caa att gca aac tac aaa      672
Lys Ile Phe Leu Pro Asp Phe Gln Arg Trp Gln Ile Ala Asn Tyr Lys
210                 215                 220 ccg gac aag gtt tat cag gtt caa ggc ggc gat cac aag ctg cag ctg      720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca      768
Thr Lys Thr Glu Glu Val Ala His Ile Leu Gln Glu Val Ala Asp Ala
                245                 250                 255 tac gct taa                                                           777
Tyr Ala
```

<210> SEQ ID NO 36
<211> LENGTH: 258
<212> TYPE: PRT
<213> ORGANISM: Manihot esculenta
<220> FEATURE:
<223> OTHER INFORMATION: Modified SHNL involving replacement of Gly by
      Glu at position 165 and Val by Leu at position 173 and Met by
      Leu at position 174

<400> SEQUENCE: 36

```
Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
            20                  25                  30

Val Thr Ala Leu Asp Met Ala Ala Ser Gly Ile Asp Pro Arg Gln Ile
        35                  40                  45

Glu Gln Ile Asn Ser Phe Asp Glu Tyr Ser Glu Pro Leu Leu Thr Phe
    50                  55                  60

Leu Glu Lys Leu Pro Gln Gly Glu Lys Val Ile Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
        115                 120                 125

Arg Asp Thr Glu Tyr Phe Thr Phe Thr Asn Ile Thr Gly Glu Thr Ile
    130                 135                 140

Thr Thr Met Lys Leu Gly Phe Val Leu Leu Arg Glu Asn Leu Phe Thr
145                 150                 155                 160

Lys Cys Thr Asp Glu Glu Tyr Glu Leu Ala Lys Met Leu Leu Arg Lys
                165                 170                 175

Gly Ser Leu Phe Gln Asn Val Leu Ala Gln Arg Pro Lys Phe Thr Glu
            180                 185                 190
```

```
Lys Gly Tyr Gly Ser Ile Lys Lys Val Tyr Ile Trp Thr Asp Gln Asp
    195                 200                 205

Lys Ile Phe Leu Pro Asp Phe Gln Arg Trp Gln Ile Ala Asn Tyr Lys
    210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
            245                 250                 255

Tyr Ala

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (23)..(25)
<223> OTHER INFORMATION: n is a, c, g, or t

<400> SEQUENCE: 37
tgaaaacctg ttcaccaaat gcnnngatgg cgaatatgaa ctggc              45

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (21)..(23)
<223> OTHER INFORMATION: n is a, c, g, or t

<400> SEQUENCE: 38
gccagttcat attcgccatc nnngcatttg gtgaacaggt tttca              45

<210> SEQ ID NO 39
<211> LENGTH: 777
<212> TYPE: DNA
<213> ORGANISM: Manihot esculenta
<220> FEATURE:
<221> NAME/KEY: CDS
<222> LOCATION: (1)..(777)
<223> OTHER INFORMATION: cDNA coding for Modified SHNL involving
      a replacement of Thr by Asp at position 163

<400> SEQUENCE: 39 atg gtt act gca cac ttc gtt ctg att cac acc att tgt cac ggc gca    48
Met Val Thr Ala His Phe Val Leu Ile His Thr Ile Cys His Gly Ala
1               5                   10                  15 tgg att tgg cac aaa ctg aaa ccg gcc ctg gaa cgt gct ggc cac aaa    96
Trp Ile Trp His Lys Leu Lys Pro Ala Leu Glu Arg Ala Gly His Lys
            20                  25                  30 gtt act gca ctg gac atg gca gcc agt ggc att gac ccg cgt caa att   144
Val Thr Ala Leu Asp Met Ala Ala Ser Gly Ile Asp Pro Arg Gln Ile
        35                  40                  45 gaa cag atc aac tct ttc gat gaa tac tct gaa ccg ctg ctg act ttc   192
Glu Gln Ile Asn Ser Phe Asp Glu Tyr Ser Glu Pro Leu Leu Thr Phe
50                  55                  60 ctg gaa aaa ctg ccg caa ggc gaa aag gtt atc att gtt ggt gaa agc   240
Leu Glu Lys Leu Pro Gln Gly Glu Lys Val Ile Ile Val Gly Glu Ser
65                  70                  75                  80
```

```
tgt gca ggc ctg aac att gct att gct gct gat cgt tac gtt gac aaa    288
Cys Ala Gly Leu Asn Ile Ala Ile Ala Ala Asp Arg Tyr Val Asp Lys
        85                  90                  95 att gca gct ggc gtt ttc cac aac tcc ctg ctg ccg gac acc gtt cac    336
Ile Ala Ala Gly Val Phe His Asn Ser Leu Leu Pro Asp Thr Val His
100                 105                 110 agc ccg tct tac act gtt gaa aag ctg ctg gaa tcg ttc ccg gac tgg    384
Ser Pro Ser Tyr Thr Val Glu Lys Leu Leu Glu Ser Phe Pro Asp Trp
115                 120                 125 cgt gac aca gaa tat ttc acg ttc acc aac atc act ggc gaa acc atc    432
Arg Asp Thr Glu Tyr Phe Thr Phe Thr Asn Ile Thr Gly Glu Thr Ile
130                 135                 140 act acc atg aaa ctg ggt ttc gtt ctg ctg cgt gaa aac ctg ttc acc    480
Thr Thr Met Lys Leu Gly Phe Val Leu Leu Arg Glu Asn Leu Phe Thr
145                 150                 155                 160 aaa tgc gat gat ggc gaa tat gaa ctg gca aaa atg gtt atg cgc aag    528
Lys Cys Asp Asp Gly Glu Tyr Glu Leu Ala Lys Met Val Met Arg Lys
            165                 170                 175 ggc tct ctg ttc caa aac gtt ctg gct cag cgt ccg aag ttc act gaa    576
Gly Ser Leu Phe Gln Asn Val Leu Ala Gln Arg Pro Lys Phe Thr Glu
180                 185                 190 aaa ggc tac ggc tct atc aag aaa gtt tat att tgg acc gat caa gac    624
Lys Gly Tyr Gly Ser Ile Lys Lys Val Tyr Ile Trp Thr Asp Gln Asp
195                 200                 205 aaa ata ttc ctg ccg gac ttc caa cgc tgg caa att gca aac tac aaa    672
Lys Ile Phe Leu Pro Asp Phe Gln Arg Trp Gln Ile Ala Asn Tyr Lys
210                 215                 220 ccg gac aag gtt tat cag gtt caa ggc ggc gat cac aag ctg cag ctg    720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca    768
Thr Lys Thr Glu Glu Val Ala His Ile Leu Gln Glu Val Ala Asp Ala
            245                 250                 255 tac gct taa                                                        777
Tyr Ala

<210> SEQ ID NO 40
<211> LENGTH: 258
<212> TYPE: PRT
<213> ORGANISM: Manihot esculenta
<220> FEATURE:
<223> OTHER INFORMATION: Modified SHNL involving
      a replacement of Thr by Asp at position 163

<400> SEQUENCE: 40

Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
                20                  25                  30

Val Thr Ala Leu Asp Met Ala Ala Ser Gly Ile Asp Pro Arg Gln Ile
35                  40                  45

Glu Gln Ile Asn Ser Phe Asp Glu Tyr Ser Glu Pro Leu Leu Thr Phe
50                  55                  60

Leu Glu Lys Leu Pro Gln Gly Glu Lys Val Ile Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
            100                 105                 110
```

```
Ser Pro Ser Tyr Thr Val Glu Lys Leu Leu Glu Ser Phe Pro Asp Trp
115                 120                 125

Arg Asp Thr Glu Tyr Phe Thr Phe Thr Asn Ile Thr Gly Glu Thr Ile
130                 135                 140

Thr Thr Met Lys Leu Gly Phe Val Leu Leu Arg Glu Asn Leu Phe Thr
145                 150                 155                 160

Lys Cys Asp Asp Gly Glu Tyr Glu Leu Ala Lys Met Val Met Arg Lys
                165                 170                 175

Gly Ser Leu Phe Gln Asn Val Leu Ala Gln Arg Pro Lys Phe Thr Glu
            180                 185                 190

Lys Gly Tyr Gly Ser Ile Lys Lys Val Tyr Ile Trp Thr Asp Gln Asp
195                 200                 205

Lys Ile Phe Leu Pro Asp Phe Gln Arg Trp Gln Ile Ala Asn Tyr Lys
210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
                245                 250                 255

Tyr Ala

<210> SEQ ID NO 41
<211> LENGTH: 777
<212> TYPE: DNA
<213> ORGANISM: Manihot esculenta
<220> FEATURE:
<221> NAME/KEY: CDS
<222> LOCATION: (1)..(777)
<223> OTHER INFORMATION: cDNA coding for Modified SHNL involving
      a replacement of Thr by Glu at position 163

<400> SEQUENCE: 41 atg gtt act gca cac ttc gtt ctg att cac acc att tgt cac ggc gca      48
Met Val Thr Ala His Phe Val Leu Ile His Thr Ile Cys His Gly Ala
1               5                   10                  15 tgg att tgg cac aaa ctg aaa ccg gcc ctg gaa cgt gct ggc cac aaa      96
Trp Ile Trp His Lys Leu Lys Pro Ala Leu Glu Arg Ala Gly His Lys
            20                  25                  30 gtt act gca ctg gac atg gca gcc agt ggc att gac ccg cgt caa att     144
Val Thr Ala Leu Asp Met Ala Ala Ser Gly Ile Asp Pro Arg Gln Ile
35                  40                  45 gaa cag atc aac tct ttc gat gaa tac tct gaa ccg ctg ctg act ttc     192
Glu Gln Ile Asn Ser Phe Asp Glu Tyr Ser Glu Pro Leu Leu Thr Phe
50                  55                  60 ctg gaa aaa ctg ccg caa ggc gaa aag gtt atc att gtt ggt gaa agc     240
Leu Glu Lys Leu Pro Gln Gly Glu Lys Val Ile Ile Val Gly Glu Ser
65                  70                  75                  80 tgt gca ggc ctg aac att gct att gct gct gat cgt tac gtt gac aaa     288
Cys Ala Gly Leu Asn Ile Ala Ile Ala Ala Asp Arg Tyr Val Asp Lys
                85                  90                  95 att gca gct ggc gtt ttc cac aac tcc ctg ctg ccg gac acc gtt cac     336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg     384
Ser Pro Ser Tyr Thr Val Glu Lys Leu Leu Glu Ser Phe Pro Asp Trp
115                 120                 125 cgt gac aca gaa tat ttc acg ttc acc aac atc act ggc gaa acc atc     432
Arg Asp Thr Glu Tyr Phe Thr Phe Thr Asn Ile Thr Gly Glu Thr Ile
130                 135                 140 act acc atg aaa ctg ggt ttc gtt ctg ctg cgt gaa aac ctg ttc acc     480
```

```
Thr Thr Met Lys Leu Gly Phe Val Leu Leu Arg Glu Asn Leu Phe Thr
145                 150                 155                 160 aaa tgc gaa gat ggc gaa tat gaa ctg gca aaa atg gtt atg cgc aag    528
Lys Cys Glu Asp Gly Glu Tyr Glu Leu Ala Lys Met Val Met Arg Lys
        165                 170                 175 ggc tct ctg ttc caa aac gtt ctg gct cag cgt ccg aag ttc act gaa    576
Gly Ser Leu Phe Gln Asn Val Leu Ala Gln Arg Pro Lys Phe Thr Glu
180                 185                 190 aaa ggc tac ggc tct atc aag aaa gtt tat att tgg acc gat caa gac    624
Lys Gly Tyr Gly Ser Ile Lys Lys Val Tyr Ile Trp Thr Asp Gln Asp
195                 200                 205 aaa ata ttc ctg ccg gac ttc caa cgc tgg caa att gca aac tac aaa    672
Lys Ile Phe Leu Pro Asp Phe Gln Arg Trp Gln Ile Ala Asn Tyr Lys
210                 215                 220 ccg gac aag gtt tat cag gtt caa ggc ggc gat cac aag ctg cag ctg    720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca    768
Thr Lys Thr Glu Glu Val Ala His Ile Leu Gln Glu Val Ala Asp Ala
            245                 250                 255 tac gct taa                                                         777
Tyr Ala

<210> SEQ ID NO 42
<211> LENGTH: 258
<212> TYPE: PRT
<213> ORGANISM: Manihot esculenta
<220> FEATURE:
<223> OTHER INFORMATION: Modified SHNL involving
      a replacement of Thr by Glu at position 163

<400> SEQUENCE: 42

Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
                20                  25                  30

Val Thr Ala Leu Asp Met Ala Ala Ser Gly Ile Asp Pro Arg Gln Ile
35                  40                  45

Glu Gln Ile Asn Ser Phe Asp Glu Tyr Ser Glu Pro Leu Leu Thr Phe
50                  55                  60

Leu Glu Lys Leu Pro Gln Gly Glu Lys Val Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
115                 120                 125

Arg Asp Thr Glu Tyr Phe Thr Phe Thr Asn Ile Thr Gly Glu Thr Ile
130                 135                 140

Thr Thr Met Lys Leu Gly Phe Val Leu Leu Arg Glu Asn Leu Phe Thr
145                 150                 155                 160

Lys Cys Glu Asp Gly Glu Tyr Glu Leu Ala Lys Met Val Met Arg Lys
        165                 170                 175

Gly Ser Leu Phe Gln Asn Val Leu Ala Gln Arg Pro Lys Phe Thr Glu
180                 185                 190

Lys Gly Tyr Gly Ser Ile Lys Lys Val Tyr Ile Trp Thr Asp Gln Asp
195                 200                 205
```

```
Lys Ile Phe Leu Pro Asp Phe Gln Arg Trp Gln Ile Ala Asn Tyr Lys
210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
            245                 250                 255

Tyr Ala

<210> SEQ ID NO 43
<211> LENGTH: 777
<212> TYPE: DNA
<213> ORGANISM: Manihot esculenta
<220> FEATURE:
<221> NAME/KEY: CDS
<222> LOCATION: (1)..(777)
<223> OTHER INFORMATION: cDNA coding for Modified SHNL involving
      a replacement of Thr by Ser at position 163

<400> SEQUENCE: 43 atg gtt act gca cac ttc gtt ctg att cac acc att tgt cac ggc gca        48
Met Val Thr Ala His Phe Val Leu Ile His Thr Ile Cys His Gly Ala
1               5                   10                  15 tgg att tgg cac aaa ctg aaa ccg gcc ctg gaa cgt gct ggc cac aaa        96
Trp Ile Trp His Lys Leu Lys Pro Ala Leu Glu Arg Ala Gly His Lys
            20                  25                  30 gtt act gca ctg gac atg gca gcc agt ggc att gac ccg cgt caa att       144
Val Thr Ala Leu Asp Met Ala Ala Ser Gly Ile Asp Pro Arg Gln Ile
35                  40                  45 gaa cag atc aac tct ttc gat gaa tac tct gaa ccg ctg ctg act ttc       192
Glu Gln Ile Asn Ser Phe Asp Glu Tyr Ser Glu Pro Leu Leu Thr Phe
50                  55                  60 ctg gaa aaa ctg ccg caa ggc gaa aag gtt atc att gtt ggt gaa agc       240
Leu Glu Lys Leu Pro Gln Gly Glu Lys Val Ile Ile Val Gly Glu Ser
65                  70                  75                  80 tgt gca ggc ctg aac att gct att gct gct gat cgt tac gtt gac aaa       288
Cys Ala Gly Leu Asn Ile Ala Ile Ala Ala Asp Arg Tyr Val Asp Lys
                85                  90                  95 att gca gct ggc gtt ttc cac aac tcc ctg ctg ccg gac acc gtt cac       336
Ile Ala Ala Gly Val Phe His Asn Ser Leu Leu Pro Asp Thr Val His
            100                 105                 110 agc ccg tct tac act gtt gaa aag ctg ctg gaa tcg ttc ccg gac tgg       384
Ser Pro Ser Tyr Thr Val Glu Lys Leu Leu Glu Ser Phe Pro Asp Trp
115                 120                 125 cgt gac aca gaa tat ttc acg ttc acc aac atc act ggc gaa acc atc       432
Arg Asp Thr Glu Tyr Phe Thr Phe Thr Asn Ile Thr Gly Glu Thr Ile
130                 135                 140 act acc atg aaa ctg ggt ttc gtt ctg ctg cgt gaa aac ctg ttc acc       480
Thr Thr Met Lys Leu Gly Phe Val Leu Leu Arg Glu Asn Leu Phe Thr
145                 150                 155                 160 aaa tgc tct gat ggc gaa tat gaa ctg gca aaa atg gtt atg cgc aag       528
Lys Cys Ser Asp Gly Glu Tyr Glu Leu Ala Lys Met Val Met Arg Lys
            165                 170                 175 ggc tct ctg ttc caa aac gtt ctg gct cag cgt ccg aag ttc act gaa       576
Gly Ser Leu Phe Gln Asn Val Leu Ala Gln Arg Pro Lys Phe Thr Glu
180                 185                 190 aaa ggc tac ggc tct atc aag aaa gtt tat att tgg acc gat caa gac       624
Lys Gly Tyr Gly Ser Ile Lys Lys Val Tyr Ile Trp Thr Asp Gln Asp
195                 200                 205 aaa ata ttc ctg ccg gac ttc caa cgc tgg caa att gca aac tac aaa       672
Lys Ile Phe Leu Pro Asp Phe Gln Arg Trp Gln Ile Ala Asn Tyr Lys
```

```
                  210                 215                 220
ccg gac aag gtt tat cag gtt caa ggc ggc gat cac aag ctg cag ctg    720
Pro Asp Lys Val Tyr Gln Val Gln Gly Gly Asp His Lys Leu Gln Leu
225                 230                 235                 240 aca aaa act gaa gaa gta gct cac att ctg caa gaa gtt gct gat gca    768
Thr Lys Thr Glu Glu Val Ala His Ile Leu Gln Glu Val Ala Asp Ala
        245                 250                 255 tac gct taa                                                        777
Tyr Ala

<210> SEQ ID NO 44
<211> LENGTH: 258
<212> TYPE: PRT
<213> ORGANISM: Manihot esculenta
<220> FEATURE:
<223> OTHER INFORMATION: Modified SHNL involving
      a replacement of Thr by Ser at position 163

<400> SEQUENCE: 44

Met Val Thr Ala His Phe Val Leu Ile His Thr Ile Cys His Gly Ala
1               5                   10                  15

Trp Ile Trp His Lys Leu Lys Pro Ala Leu Glu Arg Ala Gly His Lys
            20                  25                  30

Val Thr Ala Leu Asp Met Ala Ala Ser Gly Ile Asp Pro Arg Gln Ile
35                  40                  45

Glu Gln Ile Asn Ser Phe Asp Glu Tyr Ser Glu Pro Leu Leu Thr Phe
50                  55                  60

Leu Glu Lys Leu Pro Gln Gly Glu Lys Val Ile Ile Val Gly Glu Ser
65                  70                  75                  80

Cys Ala Gly Leu Asn Ile Ala Ile Ala Ala Asp Arg Tyr Val Asp Lys
                85                  90                  95

Ile Ala Ala Gly Val Phe His Asn Ser Leu Leu Pro Asp Thr Val His
            100                 105                 110

Ser Pro Ser Tyr Thr Val Glu Lys Leu Leu Glu Ser Phe Pro Asp Trp
115                 120                 125

Arg Asp Thr Glu Tyr Phe Thr Phe Thr Asn Ile Thr Gly Glu Thr Ile
130                 135                 140

Thr Thr Met Lys Leu Gly Phe Val Leu Leu Arg Glu Asn Leu Phe Thr
145                 150                 155                 160

Lys Cys Ser Asp Gly Glu Tyr Glu Leu Ala Lys Met Val Met Arg Lys
                165                 170                 175

Gly Ser Leu Phe Gln Asn Val Leu Ala Gln Arg Pro Lys Phe Thr Glu
            180                 185                 190

Lys Gly Tyr Gly Ser Ile Lys Lys Val Tyr Ile Trp Thr Asp Gln Asp
195                 200                 205

Lys Ile Phe Leu Pro Asp Phe Gln Arg Trp Gln Ile Ala Asn Tyr Lys
210                 215                 220

Pro Asp Lys Val Tyr Gln Val Gln Gly Gly Asp His Lys Leu Gln Leu
225                 230                 235                 240

Thr Lys Thr Glu Glu Val Ala His Ile Leu Gln Glu Val Ala Asp Ala
                245                 250                 255

Tyr Ala
```

MODIFIED S-HYDROXYNITRILE LYASE

CROSS REFERENCE TO RELATED APPLICATION

This application is a national phase application based on PCT/JP2005/006730, filed Mar. 30, 2005, which claims the priority of Japanese Patent Application No. 2004-105642, filed Mar. 31, 2004, the content of which is incorporated herein by reference in its entirety.

TECHNICAL FIELD

The present invention relates to a novel modified S-hydroxynitrile lyase. More particularly, the present invention relates to S-hydroxynitrile lyase with improved stability via amino acid substitution.

BACKGROUND ART

S-Hydroxynitrile lyase catalyzes the reaction between hydrocyanic acid and aldehyde or ketone to generate optically active cyanohydrins. Optically active cyanohydrins are important intermediates for synthesizing medicines. Accordingly, it can be said that S-hydroxynitrile lyase is an industrially important enzyme.

S-hydroxynitrile lyases derived from Cassava (*Manihot esculenta*), Pará rubber tree (*Hevea brasiliensis*), and poaceous plants (i.e., sorghum (*Sorghum bicolor*)) have been known. Industry may prefer recombinant S-hydroxynitrile lyase in addition to wild-type enzymes, because separation of enzymes from organisms incurs a high cost.

Production of recombinant S-hydroxynitrile lyase requires a step of separating an enzyme from a solution of disrupted host cells without loss in its activity. A technique that employs chromatography such as ion-exchange chromatography is the most common method for separating enzymes. Due to the high cost thereof, however, a separation technique via heating is preferable at industrial levels.

Wagner et al. analyzed the crystal structure of *Hevea brasiliensis*-derived S-hydroxynitrile lyase and reported that this enzyme belongs to the α/β hydrolase superfamily. According to this report, the catalytic triad of Ser80, His235, and Asp207 constitute the enzyme's active center. It is located deep inside the protein, and it is linked to the outside through a narrow hydrophobic channel (Wagner U G. et al., Structure, 1996, Jul. 15, 4(7), pp. 811-822). In order to improve substrate receptivity of enzymes, modified S-hydroxynitrile lyase was developed. In this S-hydroxynitrile lyase, bulky amino acids are substituted with smaller amino acids, in the hydrophobic channel. (JP Patent Publication (Kokai) No. 2000/125886A). However, modification of S-hydroxynitrile lyase for other purposes than the substrate receptivity, for example, modification to improve thermostability, has not yet been reported.

DISCLOSURE OF THE INVENTION

An objective of the present invention is to provide novel S-hydroxynitrile lyase with improved heat tolerance and stability.

The present inventors have conducted concentrated studies in order to attain the above object. As a result, they found that amino acid substitution in S-hydroxynitrile lyase through genetic engineering could produce enzymes having significantly improved stability from that of the enzyme before modification. This has led to the completion of the present invention.

More specifically, the present invention relates to modified S-hydroxynitrile lyase, which is obtained by modifying at least one amino acid in the helix D3', helix A, and β-sheet 2 domains in the amino acid sequence of wild-type S-hydroxynitrile lyase.

Examples of wild-type S-hydroxynitrile lyase include one derived from cassava (*Manihot esculenta*) (SEQ ID NO: 2) and one derived from Pará rubber tree (*Hevea brasiliensis*) (SEQ ID NO: 4). When such wild-type S-hydroxynitrile lyase derived from *Manihot esculenta* or *Hevea brasiliensis* is employed, it is preferable to modify at least one amino acid in the region between amino acids 15 and 28 (helix A), the region between amino acids 32 and 36 (β-sheet 2), or the region between amino acids 163 and 174 (helix D3') in the amino acid sequence as shown in SEQ ID NO: 2 or the region between amino acids 15 and 28 (helix A), the region between amino acids 32 and 36 (β-sheet 2), or the region between amino acids 162 and 173 (helix D3') in the amino acid sequence as shown in SEQ ID NO: 4.

An embodiment of the modified enzyme according to the present invention is modified S-hydroxynitrile lyase, which is obtained by modifying at least one amino acid selected from amino acid residues 21, 163, 165, 169, 172, 173, and 174 in the amino acid sequence as shown in SEQ ID NO: 2.

In particular, modified S-hydroxynitrile lyase obtained by substituting amino acid 165 with an acidic amino acid in the amino acid sequence as shown in SEQ ID NO: 2 has high thermostability and organic solvent tolerance. Also, modified S-hydroxynitrile lyase obtained by modifying amino acid residue 173 to be adjacent to another monomeric amino acid in the amino acid sequence as shown in SEQ ID NO: 2 has high thermostability and organic solvent tolerance. Further, modified S-hydroxynitrile lyase obtained by modifying amino acid 163 has high thermostability.

Modified S-hydroxynitrile lyase has higher stability than that of enzymes before modification when obtained by introducing: a) substitution from lysine to aspartic acid, glutamic acid, or asparagine at position 21, b) substitution from glycine to aspartic acid or glutamic acid at position 165, c) substitution from valine to leucine at position 173, d) substitution from methionine to leucine at position 174, or e) substitution from threonine to aspartic acid, glutamic acid, or serine at position 163 to the amino acid sequence as shown in SEQ ID NO: 2. Such substitution may be introduced into a single site. Alternatively, two or more of such substitutions may be combined and introduced into two or more sites to further enhance enzyme stability.

An example of preferable modified S-hydroxynitrile lyase is one having the amino acid sequence as shown in SEQ ID NO: 6, 8, 16, 20, 22, 26, 28, 32, 36, 40, 42, or 44.

The temperature at which enzyme activity of the modified S-hydroxynitrile lyase according to the present invention is reduced to half the original level via heating for 30 minutes is preferably higher by 1° C. or more than that for wild-type S-hydroxynitrile lyase.

The present invention also provides DNA that encodes the modified S-hydroxynitrile lyase according to the present invention. A preferable example of such DNA is one that encodes the amino acid sequence as shown in SEQ ID NO: 6, 8, 16, 20, 22, 26, 28, 32, 36, 40, 42, or 44.

The present invention provides a method for producing modified S-hydroxynitrile lyase comprising cultivation of a host cell having DNA that encodes the modified S-hydroxynitrile lyase of the present invention introduced therein and recovering a protein having S-hydroxynitrile lyase activity from the resulting culture product.

Further, the present invention provides a method for producing optically active cyanohydrin comprising allowing the modified S-hydroxynitrile lyase of the present invention to react with a carbonyl compound and cyanide.

Furthermore, the present invention provides a method for improving stability of S-hydroxynitrile lyase by modifying at least one amino acid in helix D3', helix A, and β-sheet 2 domains in the amino acid sequence of wild-type S-hydroxynitrile lyase.

The modified S-hydroxynitrile lyase of the present invention has thermostability and organic solvent tolerance which are significantly improved from those of existing enzymes. Accordingly, this enzyme can be more extensively employed for industrial production of optically active cyanohydrin. The aforementioned modified S-hydroxynitrile lyase can be easily and cost-effectively purified from a solution of disrupted cells via heat treatment, without deteriorating enzyme activity. Thus, efficient production of recombinant S-hydroxynitrile lyase can be realized.

Hereafter, the present invention is described in detail.

1. Wild-Type S-Hydroxynitrile Lyase

In the present invention, the term "wild-type S-hydroxynitrile lyase (hereafter abbreviated to "SHNL")" refers to SHNL isolated and purified from a plant or SHNL having the amino acid sequence identical to that of the former SHNL. The origin of the wild-type SHNL is not particularly limited. Examples thereof include SHNL derived from poaceous plants such as sorghum (*Sorghum bicolor*), SHNL derived from Euphorbiaceae plants such as cassava (*Manihot esculenta*) or Pará rubber tree (*Hevea brasiliensis*), SHNL derived from Olacaceae plants such as *Ximenia americana*. The amino acid sequences and the nucleotide sequences of the genes of such SHNLs are already known and can be easily obtained from public databases such as GenBank. For example, the SHNL gene derived from Pará rubber tree (*Hevea brasiliensis*), the SHNL gene derived from *Manihot esculenta*, and the SHNL gene derived from sorghum are registered in the GenBank under the accession Nos. U40402 (SEQ ID NO: 3 is equivalent to CDS of U40402), Z29091, and AJ421152, respectively.

2. Conformation of S-Hydroxynitrile Lyase

Conformations of some SHNLs have been already analyzed. For example, data thereof can be obtained from the database PDB Retriever of the DNA Databank of Japan. Based on such information on conformations, SHNL forms a homodimer (see FIG. 7 and FIG. 11.) SHNL's active center is located deep inside the protein, and it is linked to the outside though a narrow hydrophobic channel.

SHNL has a domain that is referred to as "helix D3'" which binds to the helix A and β-sheet 2 domains of another SHNL when they form dimer formation. Positions of helix A, β-sheet 2, and helix D3' of the *Manihot esculenta*-derived SHNL and the *Hevea brasiliensis*-derived SHNL in the amino acid sequences are shown below.

|  | Helix A | β-sheet 2 | Helix D3' |
|---|---|---|---|
| *Manihot esculenta*-derived SHNL | 15-28 | 32-36 | 163-174 |
| *Hevea brasiliensis*-derived SHNL | 15-28 | 32-36 | 162-173 |

(Each number indicates an amino acid number in the sequence shown in the sequence listings)

As shown above, with respect to the *Manihot esculenta*-derived SHNL, helix D3' is equivalent to the region between amino acids 163 and 174 in the amino acid sequence as shown in SEQ ID NO: 2. With respect to *Hevea brasiliensis*-derived SHNL, helix D3' is equivalent to the region between amino acids 162 and 173 in the amino acid sequence as shown in SEQ ID NO: 4.

FIG. 13 shows the aligned amino acid sequences of the cassava (*Manihot esculenta*)-derived SHNL and of the Pará rubber tree (*Hevea brasiliensis*)-derived SHNL. Amino acid homology between these SHNLs is 74%, and amino acids of each SHNL are not completely identical. For example, *Hevea brasiliensis*-derived SHNL lacks the amino acid that is equivalent to amino acid 139 of the *Manihot esculenta*-derived SHNL. Thus, the amino acid number in the helix D3' domain is out of alignment by one residue. However, both SHNLs belong to the α/β hydrolase superfamily and their conformations are similar to each other. The same applies to SHNLs derived from plants of other species.

In the present invention, "helix D3'" refers to a domain that binds to "helix A" and "β-sheet 2" of another SHNL monomer when SHNL forms a dimer, which is deeply involved with thermostability or enzyme activity of SHNL. More specifically, the "helix D3'" domain is equivalent to the region between amino acids 163 and 174 of the amino acid sequence of *Manihot esculenta*-derived SHNL as shown in SEQ ID NO: 2, the region between amino acids 162 and 173 of the amino acid sequence of *Hevea brasiliensis*-derived SHNL as shown in SEQ ID NO: 4, or a region between the aforementioned amino acids in the SHNL derived from other plants. The position of helix D3' in the SHNL derived from other plants can be determined as the region corresponding to the region between amino acids 163 and 174 in SEQ ID NO: 2 or amino acids 162 and 173 in SEQ ID NO: 4 by aligning the amino acid sequence of the SHNL in question with the amino acid sequence as shown in SEQ ID NO: 2 or 4.

In the present invention, the "helix A" domain is the region between amino acids 15 and 28 in the amino acid sequence of the *Manihot esculenta*-derived SHNL as shown in SEQ ID NO: 2 or that of the *Hevea brasiliensis*-derived SHNL as shown in SEQ ID NO: 4. Alternatively, it is a region between the aforementioned amino acids in the SHNL derived from other plants. The position of helix A in the SHNL derived from other plants can be determined as the region corresponding to the region between amino acids 15 and 28 in SEQ ID NO: 2 or 4 by aligning the amino acid sequence of the SHNL in question with the amino acid sequence as shown in SEQ ID NO: 2 or 4.

In the present invention, the "β-sheet 2" domain is the region between amino acids 32 and 36 in the amino acid sequence of the *Manihot esculenta*-derived SHNL as shown in SEQ ID NO: 2 or that of the *Hevea brasiliensis*-derived SHNL as shown in SEQ ID NO: 4. Alternatively, it is a region between the aforementioned amino acids in the SHNL derived from other plants. The position of helix D3' in the SHNL derived from other plants can be determined as the region corresponding to the region between amino acids 32 and 36 in SEQ ID NO: 2 or 4 by aligning the amino acid sequence of the SHNL in question with the amino acid sequence as shown in SEQ ID NO: 2 or 4.

3. Modified S-Hydroxynitrile Lyase

The present invention relates to modified s-hydroxynitrile lyase having improved stability, which is obtained by modifying at least one amino acid in helix D3', helix A, and β-sheet 2 domains in the amino acid sequence of wild-type S-hydroxynitrile lyase.

"Amino acid modification" refers to substitution of an amino acid with an amino acid of a different type, such as reciprocal substitution of amino acids. Alternatively, modification may be carried out via introducing an adequate substituent or modifying group.

Amino acid substitution may be carried out via site-directed mutagenesis into a gene that encodes the amino acid sequence in accordance with a conventional technique. Such site-directed mutagenesis can be easily performed using a commercially available kit (for example, QuikChange XL Site-Directed Mutagenesis Kit (Stratagene) or Transformer™ Site-Directed Mutagenesis Kit (Clontech.))

In the present invention, "improved stability" refers to improvement in, for example, thermostability or organic solvent tolerance. "Improved thermostability" refers to the fact that the level of enzyme activity remaining after modified SHNL is heated and then cooled to room temperature is higher than that of wild-type SHNL that had been similarly heated. More specifically, the temperature at which enzyme activity of the modified SHNL is reduced to half the original level via heating for 30 minutes is higher by 1° C. or more than that for wild-type SHNL that is adjusted to have the same activity level and the same protein level therewith. Such phenomenon is explained as follows: "the level of thermostability/heat tolerance is improved by 1° C." More specifically, the temperature at which enzyme activity is reduced to half the original level via heating for 30 minutes is higher by 1° C. or more than that for wild-type S-hydroxynitrile lyase. The modified SHNL according to the present invention has high organic solvent tolerance in addition to high heat tolerance. Thus, it can be said to be a very useful enzyme for industrial production.

In the present invention, an amino acid in the helix D3' domain of an SHNL monomer and an amino acid in helix A and β-sheet 2 domains of another SHNL monomer are optimized to improve enzyme thermostability. An example of an effective means for improving enzyme thermostability is a method for reinforcing the capacity of oligomer formation. It is considered that ionic bonding or hydrophobic interactions between amino acid residues of monomers are involved with dimer formation of SHNL. Such factors are assumed to be effective when the distance between amino acid residues is less than 2 to 5 angstroms. Thus, an amino acid to be modified preferably has an amino acid residue of the helix D3', the helix A, or β-sheet 2 domains of another monomer within 10 angstroms therefrom (the distance between amino acid residues can be optimized via amino acid modification if the distance is within 10 angstroms). Such amino acids are amino acids 164 to 166 and amino acids 168 to 174 as shown in SEQ ID NO: 2 in the case of the helix D3' domain.

Preferable examples of the modified SHNL according to the present invention include S-hydroxynitrile lyase obtained by substituting glycine-165 with an acidic amino acid, such as aspartic acid or glutamic acid (SEQ ID NO: 6 or 8), S-hydroxynitrile lyase obtained by substituting valine-173 with leucine (SEQ ID NO: 16), S-hydroxynitrile lyase obtained by substituting methionine-174 with leucine (SEQ ID NO: 20), S-hydroxynitrile lyase obtained by substituting lysine-21 with aspartic acid, glutamic acid, or asparagine (SEQ ID NO: 22, 26, or 28), S-hydroxynitrile lyase obtained by substituting threonine-163 with aspartic acid, glutamic acid, or serine (SEQ ID NO: 40, 42, or 44), and S-hydroxynitrile lyase having mutation sites consisting of a combination of the aforementioned substitutions (SEQ ID NOs: 32 and 36) in the amino acid sequence as shown in SEQ ID NO: 2. Such modified SHNL is an excellent heat tolerant enzyme having the temperature at which the enzyme activity is reduced to half the original level is improved by 5° C. from that of wild-type SHNL and is organic solvent tolerant. Thus, it is a very useful enzyme at industrial production process.

4. Production of Modified S-Hydroxynitrile Lyase 4.1 DNA that Encodes Modified SHNL DNA that encodes the modified SHNL protein according to the present invention is obtained by introducing site-directed mutations into the gene of known wild-type SHNL. Specifically, a pair of primers that can modify a codon that encodes the amino acid of interest is designed. Next, the resulting pair of primers is used to perform extension reaction utilizing DNA that encodes wild-type SHNL as the template. Site-directed mutagenesis can be easily carried out utilizing commercialized kits (for example, QuikChange XL Site-Directed Mutagenesis Kit (Stratagene) or Transformer™ Site-Directed Mutagenesis Kit (Clontech)).

Examples of DNA that encodes the modified SHNL protein according to the present invention include DNA having the nucleotide sequence as shown in SEQ ID NO: 5, 7, 15, 19, 21, 25, 27, 29, 31, 35, 39, 41, or 43.

4.2 Recombinant Vector

DNA that encodes the aforementioned modified SHNL is then ligated (inserted) to a known vector such as a plasmid to prepare a recombinant vector. Such vector is not particularly limited as long as it can replicate the gene of interest in a host. Examples include plasmid DNA and phage DNA.

Examples of such plasmid DNA include *E. coli*-derived plasmid (for example, pET21 vector having a particularly potent T7 promoter, such as pBR322, pBR325, pUC18, pUC119, pTrcHis, or pBlueBacHis, is preferable), *Bacillus subtilis*-derived plasmids (for example, pUB110 and pTP5), and yeast-derived plasmid (for example, YEp13, YEp24, YCp50, or pYE52). An example of phage DNA is λphage.

The gene of the present invention is inserted into the aforementioned vector by first cleaving purified DNA with an adequate restriction enzyme, and inserting the cleaved DNA into an adequate restriction enzyme site or multi-cloning site of the vector DNA for ligation.

In order to express a foreign gene in a host, an adequate promoter needs to be positioned before a structural gene. Such promoter is not particularly limited. Any promoter that is known to function in a host can be employed. Promoters will be described in detail concerning each host in sections concerning transformants below. If necessary, a cis element such as an enhancer, splicing signal, poly A additional signal, libosome binding sequence (SD sequence), terminator sequence, and the like may be positioned.

4.3 Modified SHNL Expression System (Transformant)

Subsequently, the aforementioned recombinant vector is introduced into a host in a manner such that the target gene can be expressed therein to prepare a modified SHNL expression system. A host cell is not particularly limited as long as the DNA of the present invention can be expressed therein. Examples thereof include: bacteria belonging to *Escherichia* such as *Escherichia coli*, *Bacillus* such as *Bacillus subtilis*, *Pseudomonas* such as *Pseudomonas putida*, or *Rhizobium* such as *Rhizobium meliloti*; yeast such as *Saccharomyces cervisiae*, *Schizosaccharomyces pombe*, and *Pichia pastoris*; animal cells such as COS cells and CHO cells; and insect cells such as Sf19 and Sf21.

Where a bacterium such as *E. coli* is used as a host, it is preferable that the recombinant vector of the present invention be capable of self-replicating in the bacterium and, at the same time, be also comprised of a promoter, a ribosome binding sequence, the gene of the present invention, and a transcription termination sequence. Further, it may also comprise a gene for regulating a promoter. Examples of *E. coli* include *E. coli* HMS174 (DE3), K12, DH1, and B strains and examples of *Bacillus subtilis* include *Bacillus subtilis* MI 114 and 207-21. A promoter is not particularly limited as long as it can express the gene of interest in a host such as *E. coli*. For example, *E. coli*-derived or phage-derived promoters can be employed, such as: trp promoter, lac promoter, $P_L$ promoter, and $P_R$ promoter. Alternatively, an artificially designed and modified promoter, such as tac promoter, may also be employed. A method for introducing a recombinant vector into a bacterium is not particularly limited. For example, a method involving the use of calcium ions (Cohen, S. N. et al., Ploc. Natl. Acad. Sci., U.S.A., 69: 2110-2114, 1972) and electroporation can be employed.

Where yeast is used as a host, for example, *Saccharomyces cerevisiae*, *Schizosaccharomyces pombe*, or *Pichea pastris*, is used. A promoter is not particularly limited as long as it can express the gene of interest in yeast. For example, gal1 promoter, gal10 promoter, heat shock protein promoter, MFα1 promoter, PHO5 promoter, PGK promoter, GAP promoter, ADH promoter, or AOX1 promoter can be employed. A method for introducing a vector into yeast is not particularly limited. Examples of such methods include electroporation (Becker, D. M. et al., Methods. Enzymol., 194: 182-187, 1990), the spheroplast method (Hinnen, A. et al., Proc. Natl. Acad. Sci., U.S.A., 75: 1929-1933, 1978), and the lithium acetate method (Itoh, H., J. Bacteriol., 153: 163-168, 1983).

4.4 Culture of Transformant

The modified SHNL of the present invention can be obtained by culturing the transformant according to the present invention in an adequate medium and recovering a protein having enzyme activity from the culture product. A method for culturing the transformant according to the present invention is adequately determined in accordance with a host. In the case of a transformant where bacteria such as *E. coli* or yeast is employed as a host, for example, either a natural or synthetic medium may be used as long as it contains carbon sources, nitrogen sources, and inorganic salts assimilable by the microorganism and is capable of efficiently culturing the transformant.

During the culture, an antibiotic such as ampicillin or tetracycline may be added to the medium, if necessary. When a microorganism transformed with an expression vector containing an inducible promoter is cultured, an inducer may be added to the medium, if necessary. When a microorganism transformed with an expression vector containing lac promoter is cultured, for example, isopropyl-β-thiogalactopyranoside (IPTG) may be added to the medium. When culturing a microorganism transformed with an expression vector containing trp promoter, indoleacrylic acid (IAA) or the like may be added to the medium.

If the enzyme protein of the present invention is produced in the relevant microorganism or cell after the culture, the cultured microorganism or cell is disrupted. If the protein of the present invention is secreted outside of the microorganism or cell, the culture broth may be used in that state or subjected to centrifugation or another procedure to remove the microorganism or cell.

Ammonium sulfate precipitation, SDS-PAGE, gel filtration, ion exchange chromatography, affinity chromatography, or other means are employed independently or in an appropriate combination to isolate and purify proteins.

The enzyme activity of the modified SHNL according to the present invention can be confirmed by adding the enzyme to a reaction solution that contains a substrate, i.e., adequate cyanide, and aldehyde or ketone and detecting the generated optically active cyanohydrin. Optically active cyanohydrin can be confirmed by, for example, gas chromatography or high-performance liquid chromatography. Alternatively, an antibody that specifically binds to the modified SHNL of the present invention can be prepared to confirm the expression via Western blotting using the resulting antibody. For example, the enzyme activity of SHNL can be confirmed by assaying the amount of aldehyde generated per unit time (calculated based on the absorbance at 249.6 nm) upon degradation of mandelonitrile by SHNL.

In general, a procedure such as ion-exchange chromatography is necessary for purifying SHNL. If the modified SHNL of the present invention is subjected to heating, however, a protein derived from the host (*E. coli*) can be removed via centrifugation or other means while maintaining the enzyme activity. Accordingly, the modified SHNL of the present invention can be simply and cost-effectively purified and can significantly improve the efficiency of producing recombinant enzymes.

The modified SHNL of the present invention can be produced in accordance with the methods disclosed in JP Patent Publication (Kokai) Nos. 10-373246 A (1998), 10-373248A (1998), or 11-367251 A (1999).

5. Synthesis of Optically Active Cyanohydrin Using Modified S-Hydroxynitrile Lyase The modified SHNL of the present invention can synthesize optically active cyanohydrin with the production efficiency and optical purity equivalent to those of wild-type SHNL, in spite of its high thermostability and organic solvent tolerance. Optically active cyanohydrin can be synthesized with the use of the present invention's modified SHNL in the same manner as wild-type SHNL.

Specifically, the modified SHNL of the present invention and a reaction substrate are added to a reaction solvent, and reaction is carried out at 10° C. to 50° C. for 20 minutes to 24 hours. Thus, optically active cyanohydrin can be synthesized. The reaction time is adequately determined in accordance with the conversion rate of the substrate. Examples of a reaction substrate that can be employed include a carbonyl compound and cyanide. A carbonyl compound is an aldehyde or ketone represented by COR1R2 wherein R1 and R2 each independently represent: a hydrogen atom, substituted or non-substituted, linear or branched, and saturated alkyl having 1 to 18 carbon atoms, or a substituted or non-substituted cyclic 5-22-membered aromatic group, provided that R1 and R2 do not simultaneously represent a hydrogen atom. Cyanide is not particularly limited as long as it generates cyanide ions ($CN^-$). Examples thereof that can be employed include hydrogen cyanides such as sodium cyanide or potassium cyanide and cyanohydrins such as acetone cyanohydrin.

Use of a reaction solvent mainly composed of an organic solvent that is hardly soluble or insoluble in water is preferable from the viewpoints as described below. That is, when a large quantity of water is present in a reaction system, racemization of optically active cyanohydrin generated via enzyme reaction is likely to occur. When aldehyde or ketone having a low degree of water solubility is used as a starting material, the production efficiency is deteriorated. Such organic solvent is not particularly limited if it does not affect the synthesis of optically active cyanohydrin via enzyme reaction. An organic solvent can be adequately selected in accordance with properties of aldehyde or ketone that is used as a starting material for synthesis or properties of cyanohydrin that is a generated product. Specific examples include: aliphatic or aromatic, linear, branched, or cyclic, and saturated or unsaturated hydrocarbon solvents that may be optionally halogenated, such as pentane, hexane, toluene, xylene, and methylene chloride; aliphatic or aromatic, linear, branched, or cyclic, and saturated or unsaturated alcohol solvents that may be optionally halogenated, such as isopropyl alcohol, n-butanol, isobutanol, t-butanol, hexanol, cyclohexanol, and n-amyl alcohol; aliphatic or aromatic, linear, branched, or cyclic, and saturated or unsaturated ether solvents that may be optionally halogenated, such as diethyl ether, dipropyl ether, diisopropyl ether, dibutyl ether, and methyl t-butyl ether; and aliphatic or aromatic, linear, branched, or cyclic, and saturated or unsaturated ester solvents that may be optionally halogenated, such as methyl formate, methyl acetate, ethyl acetate, butyl acetate, and methyl propionate. They may be used alone or in combinations of two or more. The aforementioned solvent that comprises or is saturated with water or an aqueous buffer can also be employed.

In the process of industrial production, the modified SHNL may be utilized as an enzyme immobilized on an adequate inorganic carrier (see, for example, JP Patent Publication (Kokai) No. 2002-176974 A). Examples of preferable methods for synthesizing cyanohydrin with the use of the modified SHNL of the present invention include those disclosed in JP Patent Publication (Kokai) Nos. 2002-355085 A, 2002-176974 A, 2001-363840 A, 2001-346596 A, 2001-190275 A, 2000-245286 A, 2001-120289 A, and 2000-217590 A.

BRIEF DESCRIPTION OF THE DRAWINGS

The patent or application file contains at least one drawing executed in color. Copies of this patent or patent application publication with drawings will be provided by the Office upon request and payment of the necessary fee.

FIG. 6 is a graph showing organic solvent tolerance of Actmt-001f2-SHNL (A: ethanol tolerance; B: ethyl acetate tolerance).

FIG. 8 is a graph showing the rate of benzaldehyde conversion through repetitive reactions of Actmt-001f2-SHNL (A: changes in the conversion rate 1 hour after the initiation of the reaction depending on the number of repetition; B: changes in the conversion rate in the 11th reaction with the elapse of time).

FIG. 13 is a diagram showing the aligned amino acid sequences of the cassava (*Manihot esculenta*)-derived SHNL (SEQ ID NO.: 2) and of the Pará rubber tree (*Hevea brasiliensis*)-derived SHNL (SEQ ID NO.: 4).

FIG. 15 is a graph showing organic solvent tolerance of V173L-SHNL (A: ethanol tolerance; B: ethyl acetate tolerance).

Figure 1:
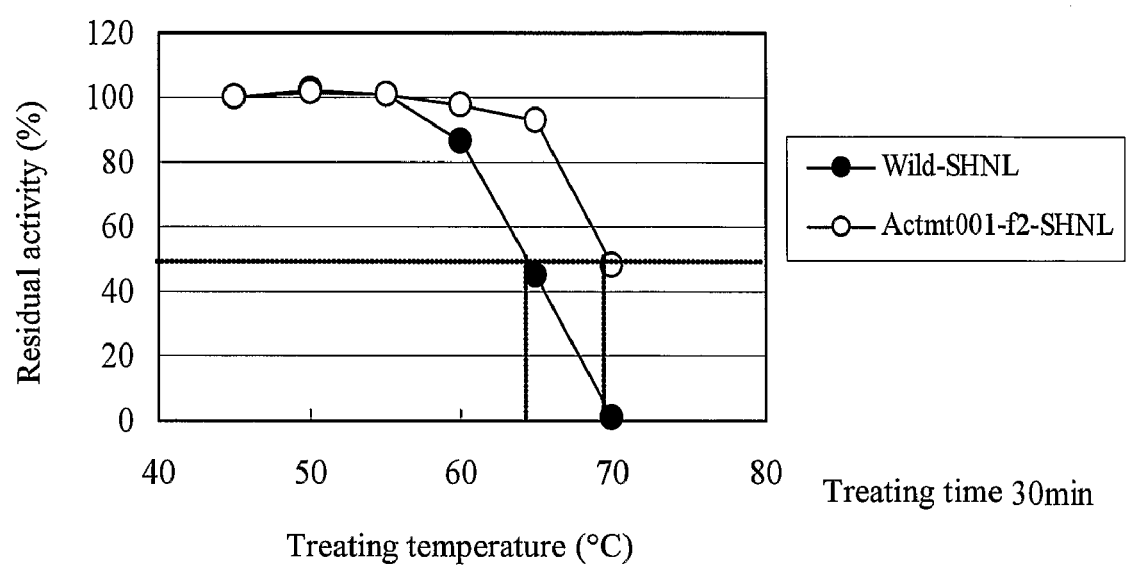
FIG. 1 is a graph showing the results of comparing thermostability of Wild-SHNL and that of Actmt-001f2-SHNL.

This description includes part or all of the contents as disclosed in the description of Japanese Patent Application No. 2004-105642, which is a priority document of the present application.

BEST MODES FOR CARRYING OUT THE INVENTION

Hereafter, the present invention is described in greater detail with reference to the examples, although the technical scope of the present invention is not limited thereto.

EXAMPLE 1

Preparation of Modified Enzyme Actmt-001f2-SHNL

1. Mutagenesis

Mutagenesis into the S-hydroxynitrile lyase (Wild-SHNL) gene derived from cassava (*Manihot esculenta*) (SEQ ID NO: 1: Japanese Patent Application No. 2002-365675) was carried out using the GeneMorph® PCR Mutagenesis Kit (Stratagene). PCR was carried out using 600 ng of the pKK223-3/SHNL-Wild plasmid having the Wild-SHNL gene incorporated into the multi-cloning site of pKK223-3 (Amersham Biosciences) as the template and the following oligo DNA as primers.

```
Forward primer:
                                       (SEQ ID NO: 9)
5'-GGG GAA TTC ATG GTT ACT GCA CAC TTC GTT CTG ATT

CAC-3'

Reverse primer:
                                       (SEQ ID NO: 10)
5'-GGG AAG CTT TTA AGC GTA TGC ATC AGC AAC TTC TTG

CAG-3'
```

2. Transformation

The resulting PCR product (SHNL-Mutants) was digested with EcoRI and HindIII restriction enzymes (Toyobo Co., Ltd.), and the resultant was ligated to the pKK233-3 vector, the multi-cloning site of which has also been digested with the EcoRI and HindIII restriction enzymes. The LigaFast™ Rapid DNA Ligation System (Promega) was used for ligation. The ligation reaction solution was applied to DH5α competent cells (Toyobo Co., Ltd.) for transformation, and a plurality of DH5α/pKK223-3/SHNL-Actmt strains were obtained.

3. Selection and Recombination into High-Expression Vector

A plurality of DH5α/pKK223-3/SHNL-Actmt strains were cultured in test tubes, 1 ml each of the culture solution was fractionated, the fractionated culture solution was centrifuged to remove the supernatant, and cell pellets were obtained. The obtained cells were resuspended in 200 μl of sodium citrate buffer (pH 5.5) and then disrupted via an ultrasonic cell homogenizer. The disrupted cells were centrifuged at 15,000 rpm for 5 minutes to obtain a solution of disrupted cells. This solution of disrupted cells was heated at 60° C. for 2 hours, and SHNL activity of the solution was then assayed. The SHNL activity was determined based on the amount of aldehyde generated per unit time upon mandelonitrile degradation by SHNL at 20° C. The amount of aldehyde generated per unit time is determined by measuring the increase in absorbance at 249.6 nm (with the use of a spectrophotometer, manufactured by Shimadzu Co., Ltd.).

On the basis of the result, the DH5α/pKK223-3/SHNL-Actmt001f2 strain that was still active after heating was selected as a thermostable strain. The selected strain was subjected to colony PCR, and the resulting PCR product was used as the template for sequencing. Based on the results of analyzing the reaction product, DH5α/pKK223-3/SHNL-Actmt001f2 was found to have a nucleotide sequence (SEQ ID NO: 5) derived from the nucleotide sequence as shown in SEQ ID NO: 1 by substitution of guanine by adenine at position 494. Thus, Actmt001f2-SHNL was found to be modified SHNL having an amino acid sequence (SEQ ID NO: 6) derived from the amino acid sequence of Wild-SHNL (SEQ ID NO: 2) by substitution of glycine by aspartic acid at position 165. Hereafter, this modified SHNL (SHNL in which glycine at position 165 has been substituted with aspartic acid) is referred to as "Actmt-001f2-SHNL."

Subsequently, the SHNL-Actmt001f2 gene was introduced into the pET21 vector (Novagen) that permits high-level expression of proteins. The pKK223-3/SHNL-Actmt001f2 plasmid was prepared, and PCR was carried out using the resulting plasmid as the template, the primers shown below, and the DNA polymerase (KODplus, TOYOBO, Co., Ltd.) to remove the EcoRI and HindIII restriction enzyme sites that have been added to both terminuses of the template. The NdeI and BamHI restriction enzyme sites were added instead.

```
Forward primer:
                                          (SEQ ID NO: 11)
5'-GGG GGG GGG CAT ATG GTT ACT GCA CAC TTC GTT CTG
ATT CAC AC-3'

Reverse primer:
                                          (SEQ ID NO: 12)
5'-GGG GGA TCC TTA AGC GTA TGC ATC AGC AAC TTC TTG
CAG-3'
```

The resulting PCR product was digested with NdeI (New England Bio Labs) and BamHI restriction enzymes (Toyobo Co., Ltd.), and the resultant was ligated to the pET21a vector (Novagen), the multi-cloning site of which has also been digested with the NdeI and BamHI restriction enzymes. The LigaFast™ Rapid DNA Ligation System (Promega) was used for ligation. The ligation reaction solution was applied to BL21 (DE3) competent cells (Novagen) for transformation, and BL21(DE3)/pET21a/SHNL-Actmt001f2, which is the expression system for SHNL in which amino acid 165 had been substituted with Asp was obtained.

EXAMPLE 2

Experiment for Thermostability of Actmt001f2-SHNL

1. Method of Experimentation

1) Preparation of Enzyme Solution

E. coli strains, BL21(DE3)/pET21a/SHNL-Wild and BL21(DE3)/pET21a/SHNL-Actmt001f2, were cultured in 5 ml of LB medium at 37° C. for 12 hours. The resulting culture broth (100 μl) was inoculated to 5 ml of NS-2 medium shown below, and IPTG was added thereto to perform culture at 20° C. for 60 hours. After the completion of culture, the culture solution was centrifuged to obtain the cell pellets. The cell pellets were suspended in a 0.2M sodium citrate buffer (pH 5.5) and cells were ultrasonically disrupted. The solution of disrupted cells was centrifuged, the supernatant was recovered as enzyme solutions of Wild-SHNL and Actmt-001f2-SHNL. The enzyme solution of Wild-SHNL had an activity level of 74 U/ml and a protein concentration of 6.29 mg/ml. The enzyme solution of Actmt-001f2-SHNL had an activity level of 69 U/ml and a protein concentration of 5.96 mg/ml.

TABLE 1

| Composition of NS-2 medium (pH 6) | |
|---|---|
| Glycerol | 40 g |
| $(NH_4)_2SO_4$ | 10 g |
| $KH_2PO_4$ | 2 g |
| $K_2HPO_4$ | 6 g |
| Yeast Ext | 40 g |
| $MgSO_4$ | 1 g |
| Adekanol | 20 drops |
| Total | 1 liter (the total amount was adjusted to 1 liter with distilled water) |

The aforementioned medium was autoclaved, and filter-sterilized ampicilin (100 mg/l: final concentration) and filter-sterilized IPTG (238 mg/l: final concentration) was added.

2) Heat Treatment of Enzyme Solution

The enzyme solutions of Wild-SHNL and Actmt-001f2-SHNL (200 μl each) were placed in Eppendorf tubes and the enzyme solutions were heated to 45° C. to 70° C. in a heat block. After the heat treatment of the 30 minutes, the samples were recovered by centrifugation, and the level of residual activity was assayed in relation to the enzyme activity at the initiation of the reactions. The enzyme activity was assayed in the manner as described in Example 1.

2. Result of Experiment

The activity of the solution of wild-SHNL was reduced to half the original level at 65° C.; however, 90% or more activity of Actmt-001f2-SHNL remained (FIG. 1). The activity of Actmt-001f2-SHNL was reduced to half the original level at around 70° C. This indicated that heat tolerance thereof was improved by approximately 5° C. from that of Wild-SHNL. Accordingly, heat tolerance of *Manihot esculenta*-derived SHNL was found to improve by substitution of amino acid 165 from glycine to aspartic acid.

Figure 2:
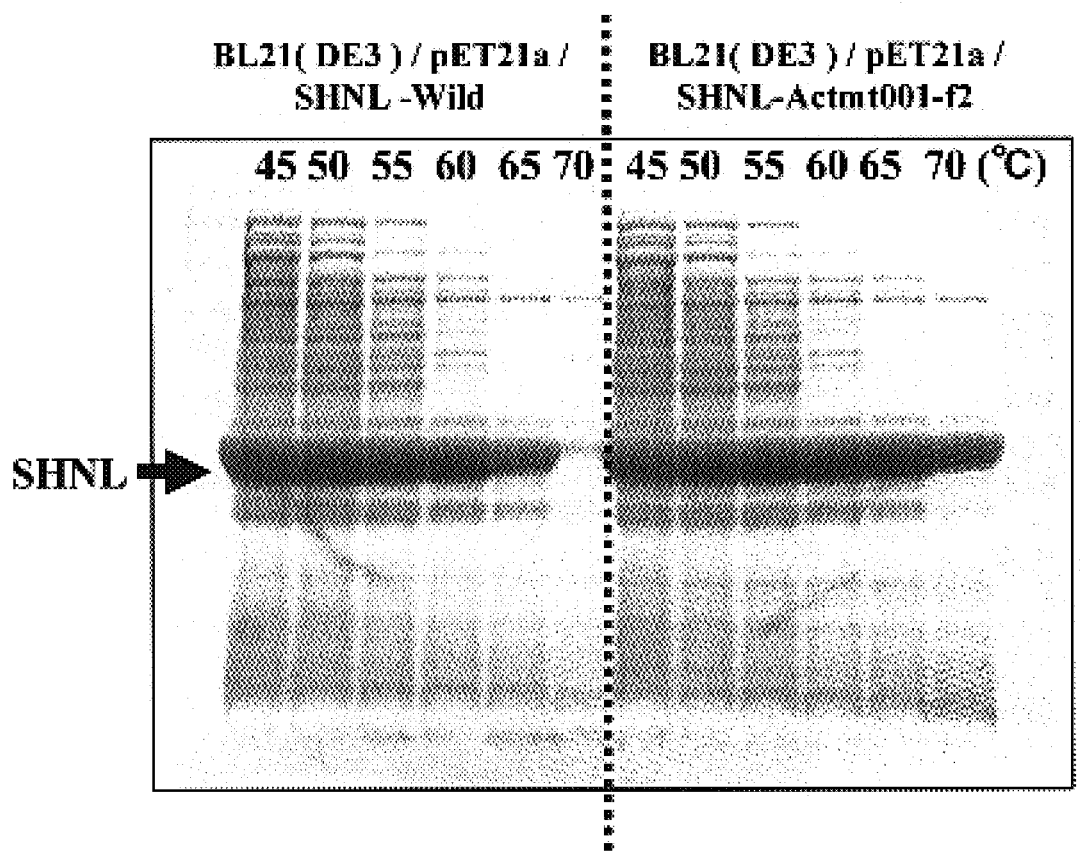
FIG. 2 is a photograph showing the results of analyzing the heated Wild-SHNL and Actmt-001f2-SHNL via SDS-PAGE samples.

The heated enzyme solution sample was analyzed via SDS-PAGE (FIG. 2). Because the sample was heated and then centrifuged, denatured water insolublized proteins were removed.

As shown in FIG. 2, the amount of enzyme in Wild-SHNL begins to rapidly decrease at 60° C. (see the band indicated by an arrow in FIG. 2), and substantially disappears at 70° C. In contrast, the amount of enzyme in Actmt-001f2-SHNL decreases, however, a sufficient amount of enzyme remains at 70° C. The result of SDS-PAGE is consistent with the result of assaying enzyme activity (FIG. 1).

Figure 3:
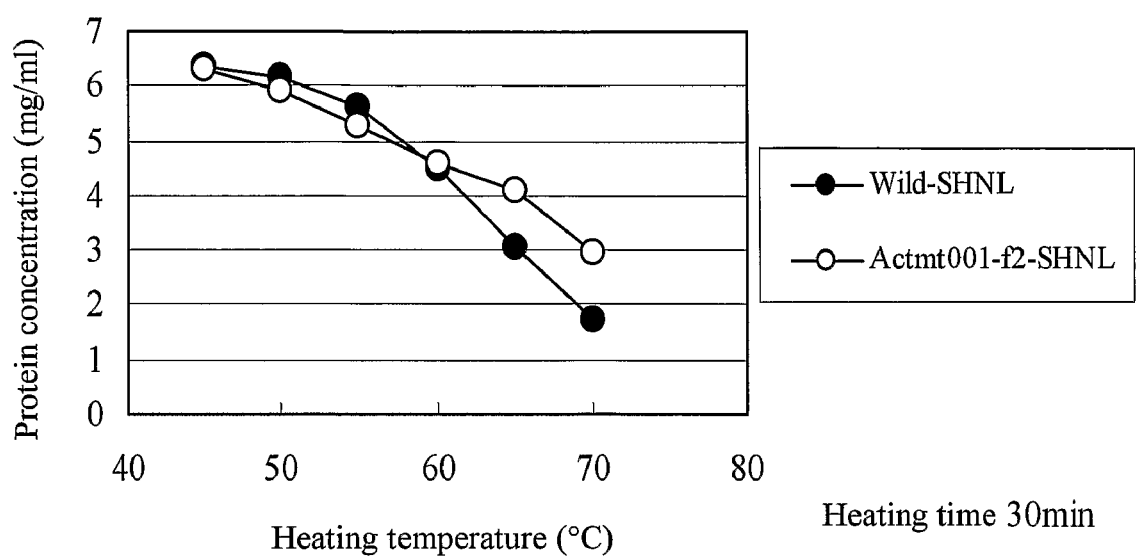
FIG. 3 is a graph showing changes in protein levels in the heated Wild-SHNL and Actmt-001f2-SHNL samples.

FIG. 3 shows the heat-induced changes in the protein concentration in the sample. The sample at 45° C. contains a large quantity of proteins derived from an *E. coli* host (FIGS. 2 and 3). Since such proteins are denatured and insolubilized in water via heating, they are removed from the sample as the temperature rises. Thus, the protein concentration in the Wild-SHNL sample and that in the Actmt-001f2-SHNL decreased in an almost linear fashion as the temperature increased.

Generally, procedures such as gel filtration chromatography are required for enzyme purification. If Actmt-001f2-SHNL is heated, *E. coli*-derived proteins can be removed while maintaining the enzyme activity via centrifugation or other means. Accordingly, it was considered that Actmt-001f2-SHNL could be simply and cost-effectively purified.

EXAMPLE 3

Examination of Changes in Stability and Protein Concentration of Actmt-001f2-SHNL via Heating at 60° C.

In order to verify that *E. coli*-derived proteins can be actually removed while maintaining enzyme activity via heating, the following experiment was carried out.

1. Method of Experimentation

1) Preparation of Enzyme Solution

*E. Coli* strains, BL21(DE3)/pET21a/SHNL-Wild and BL21(DE3)/pET21a/SHNL-Actmt001f2, were cultured in 5 ml of LB medium at 37° C. for 12 hours. The resulting culture solution (100 µl) was inoculated to 5 ml of NS-2 medium, and IPTG was added to perform culture at 20° C. for 60 hours. After the completion of culture, the culture solution was centrifuged to recover cells. The recovered cells were suspended in a 0.2M sodium citrate buffer (pH 5.5) and cells were ultrasonically disrupted. The solution of disrupted cells was centrifuged, the supernatant was recovered, and the enzyme solutions of Wild-SHNL and Actmt-001f2-SHNL were obtained. The enzyme solution of Wild-SHNL had an activity level of 83 U/ml and a protein concentration of 7.01 mg/ml. The enzyme solution of Actmt-001f2-SHNL had an activity level of 81 U/ml and a protein concentration of 6.65 mg/ml.

2) Heat Treatment of Enzyme Solution

The enzyme solutions of Wild-SHNL and Actmt-001f2-SHNL (200 µl each) were placed in Eppendorf tubes and the enzyme solutions were heated to 60° C. in a heat block. The solutions were centrifuged every 30 minutes, 10 µl each of the samples were recovered, and the level of residual activity and the protein concentration were assayed.

2. Result of Experiment

1) Residual Activity

Figure 4:
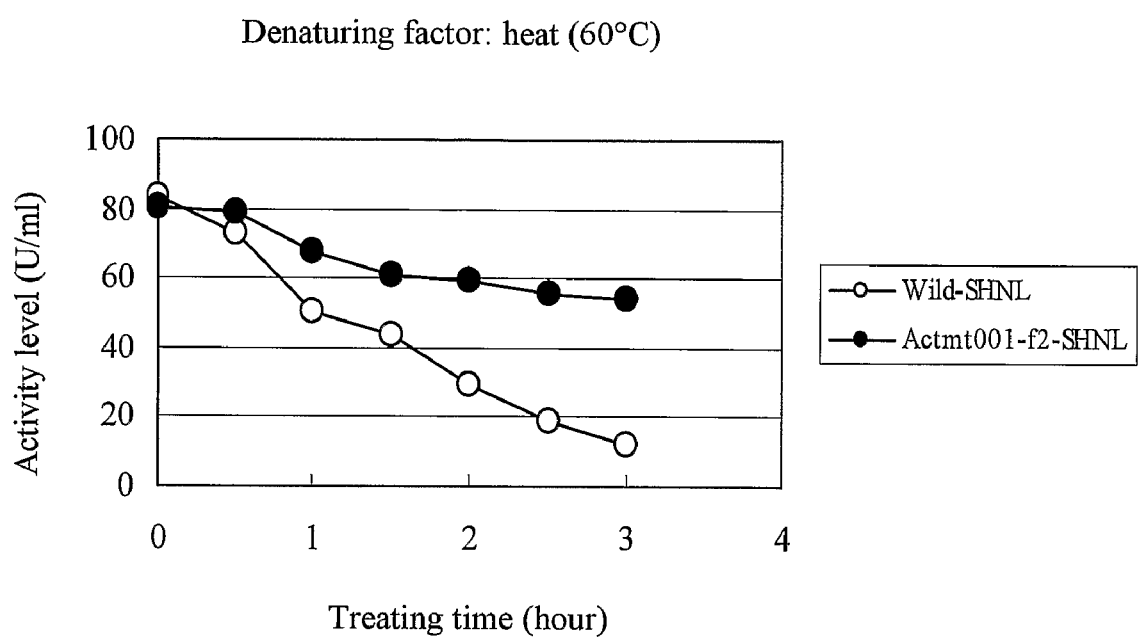
FIG. 4 is a graph showing the results of comparing thermostability of Wild-SHNL and that of Actmt-001f2-SHNL.

The activity of Wild-SHNL was reduced to half the original level via heating for 1.5 hour; however, 75% of activity of Actmt-001f2-SHNL still remained after heating for 1.5 hour (FIG. 4).

2) Changes in Protein Concentration

Figure 5:
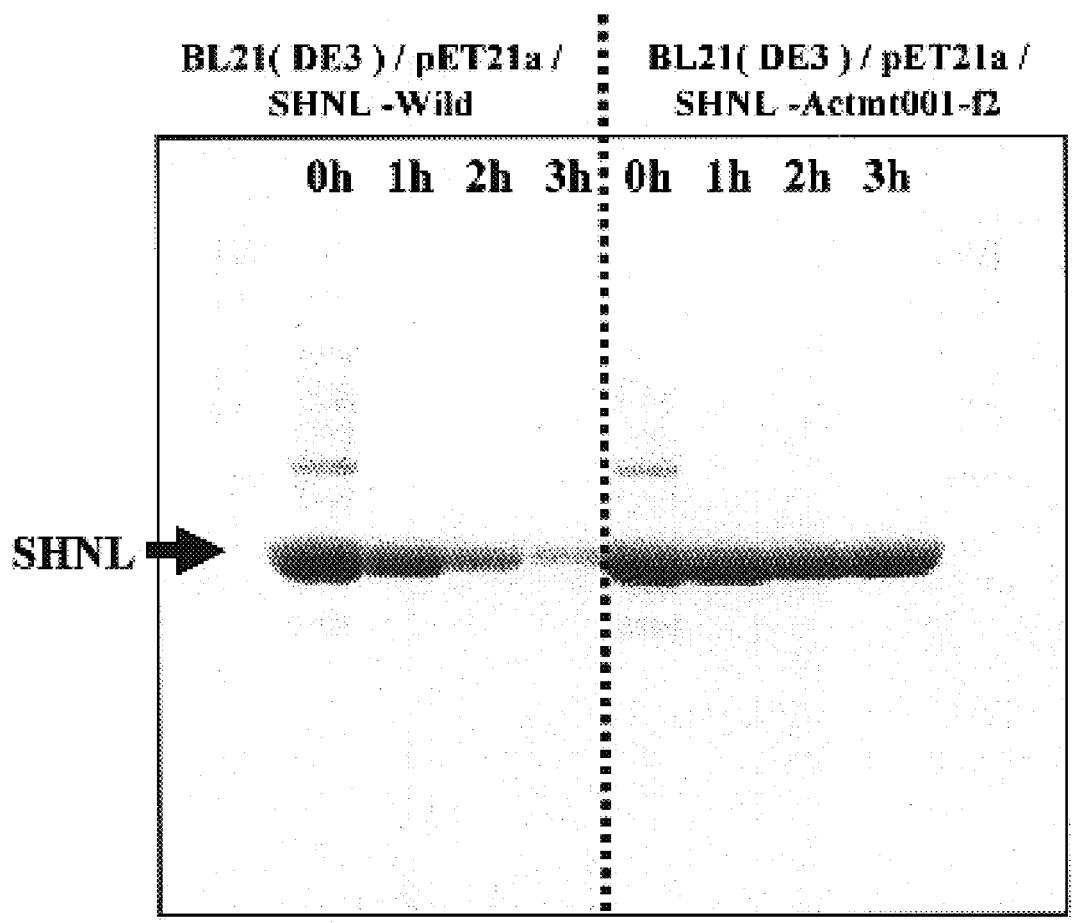
FIG. 5 is a photograph showing the results of analyzing the heated Wild-SHNL and Actmt-001f2-SHNL samples (supernatants) via SDS-PAGE.
Figure 7:
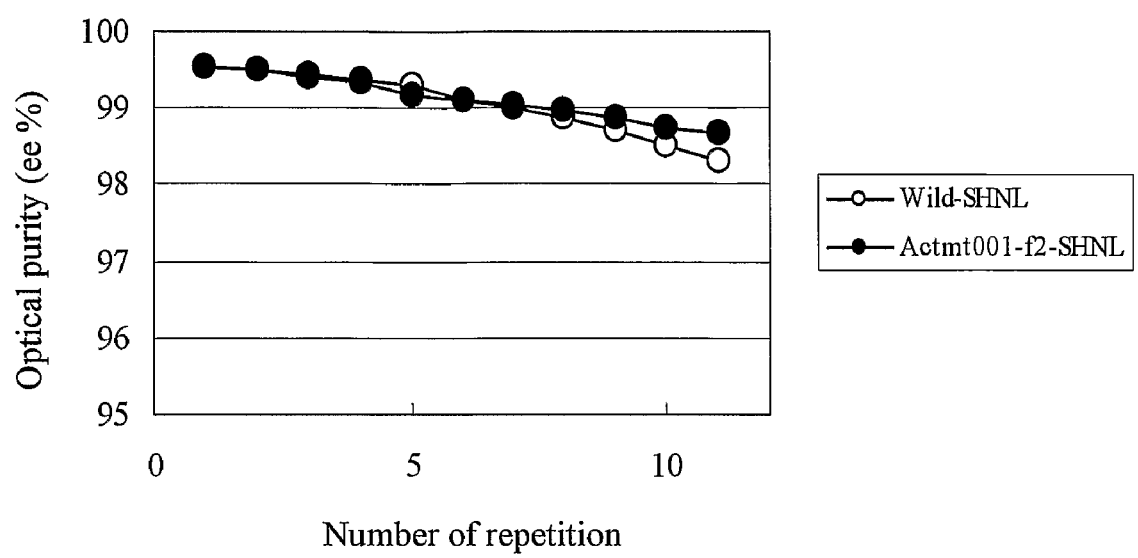
FIG. 7 is a graph showing the optical purity of S-mandelonitrile 1 hour after the initiation of the repetitive reaction of Actmt-001f2-SHNL.

The resulting samples were analyzed via SDS-PAGE. Based on the results of SDS-PAGE (FIG. 5), the samples contained a large quantity of *E. coli*-derived proteins at 0 hour (without heating). In the case of the heated samples, however, *E. coli*-derived proteins were found to be removed from the Wild-SHNL and Actmt-001f2-SHNL samples.

The protein concentration in the Actmt-001f2-SHNL sample after heating for 1 hour was 4.25 mg/ml, which was reduced to 64% of the initial level (Table 2). In contrast, the residual activity of Actmt-001f2-SHNL after heating for 1 hour was 80% or higher. Accordingly, it was found that *E. coli*-derived proteins could be removed from Actmt-001f2-SHNL while maintaining enzyme activity via heating. In the case of Wild-SHNL, the protein concentration 1 hour later was 4.21 mg/ml, and the residual activity was 60%, which was the value reduced to 63% of the initial level.

TABLE 2

Changes in stability and protein concentration (mg/ml-sample) via heating at 60° C.

| Heating time | Wild-SHNL | | Actmt-001f2-SHNL | |
|---|---|---|---|---|
| 0 hr | 7.01 | (100) | 6.65 | (100) |
| 1 hr | 4.21 | (61) | 4.25 | (83) |
| 2 hr | 3.37 | (35) | 4.14 | (73) |

* Values in the parentheses represent the residual activity (%) at that time point As apparent from the data, Wild-SHNL is disadvantageously denatured and inactivated with other contaminating proteins via heating at 60° C. Thus, separation and purification via heating at temperatures higher than this level is difficult. Although heating at 45° C. to 55° C. is feasible, the rate of contaminating proteins being denatured is very mild in such a temperature range, as is apparent from FIG. 3. Accordingly, a considerable amount of time would be required for sufficient separation and purification.

EXAMPLE 4

Organic Solvent Tolerance of Actmt-001f2-SHNL

In general, thermostability of enzymes is deeply involved with other environmental stresses such as stability in organic solvents. Thus, Actmt-001f2-SHNL can also have improved stability in organic solvents. Therefore, organic solvent tolerance of Actmt-001f2-SHNL was examined.

1. Method of Experimentation

1) Preparation of Enzyme Solution

An enzyme solution was prepared in the same manner as in Example 2. When stress tolerance of enzymes is assayed, contaminating proteins in the sample sometimes function as protecting agents, and tolerance may appear to be improved. Thus, the aforementioned samples were diluted with bovine serum albumin and a buffer, all the samples were adjusted to have an activity level of 44.19 U/ml and a specific activity level of 6.50 U/mg, and influences of contaminating proteins were eliminated from the experimentation system.

2) Organic Solvent Treatment

Ethanol and ethyl acetate were added to the enzyme solution as organic solvents. The final concentration of ethanol was 30%, and that of ethyl acetate was 40%. Thereafter, the samples were stored for 50 hours with agitation. Centrifugation was carried out every several hours, 10 µl each of the supernatant (aqueous layer) was fractionated as the samples, and the activity level was assayed.

2. Result of Experimentation

Ethanol tolerance (FIG. 6A) and ethyl acetate tolerance (FIG. 6B) of Actmt-001f2-SHNL were superior to those of Wild-SHNL.

EXAMPLE 5

Production of Optically Active Cyanohydrin by Actmt-001f2-SHNL

SHNL is an enzyme that catalyzes the reaction between an aldehyde or ketone and hydrocyanic acid to synthesize optically active cyanohydrin. The ability of Actmt-001f2-SHNL for catalyzing this reaction was examined by comparing with that of Wild-SHNL.

1. Method of Experimentation

1) Preparation of Enzyme Solution

BL21(DE3)/pET21a/SHNL-Wild and BL21(DE3)/pET21a/SHNL-Actmt001f2 were cultured, the culture solutions were centrifuged to remove the supernatants, and cell pellets were obtained. A sodium citrate buffer (0.66 g, pH 5.5) was added to the cell pellets (0.33 g) for resuspension, and cells were disrupted via an ultrasonic cell homogenizer. The disrupted cells were centrifuged at 15,000 rpm for 5 minutes to obtain solutions of disrupted cells. The solutions of disrupted cells were heated at 50° C. for 3 hours and then centrifuged. The supernatants were filtered through a 0.45 µm-filter, followed by concentration via ultrafiltration. A sodium citrate buffer (pH 5.5) was added to each of these enzyme concentrates to adjust the activity levels as shown below. The prepared enzyme solution (0.3 ml) was mixed with 300 mg of silica gel to obtain immobilized enzymes.

TABLE 3

| Enzyme | Activity level (U/ml) | Specific activity level (U/mg) |
| --- | --- | --- |
| Wild-SHNL | 250 | 31.02 |
| Actmt-001f2-SHNL | 250 | 27.16 |

2) Enzyme Reaction

A 0.2M citrate buffer (0.337 ml, pH 5.5) was added to 4.492 ml of t-butyl methyl ether and 1.61 M HCN. This solution was agitated for 30 minutes and then allowed to stand, followed by removal of an aqueous layer. This solution was added to a 9 ml screw vial containing 300 mg of the immobilized enzymes prepared above. Benzaldehyde (0.508 ml) was added, and the mixture was agitated via a bottle roller to perform enzyme reaction. The reaction solution (4 ml) was recovered 1 hour after the initiation of the reaction. Subsequently, the same amount of HCN/t-butyl methyl ether solution, which had been subjected to the same treatment, was added, and the same amount of benzaldehyde was added to perform enzyme reaction. The reaction solution (5 ml) was recovered 1 hour after the initiation of the reaction. This reaction was repeated and a total of 11 enzyme reactions were carried out. At the 11th reaction, the reaction time was extended to assay the process of enzyme reaction, and the process was analyzed.

2. Result of Experimentation

The thermostable enzyme (Actmt-001f2-SHNL) generated S-mandelonitrile at the same reaction rate as Wild-SHNL. Thus, Actmt-001f2-SHNL was found to have the capacity for synthesizing optically active cyanohydrin, which was equivalent to that of Wild-SHNL. As the reaction was repeatedly carried out, the reaction rates thereof gradually declined. The degree of the reaction rate decline was milder in the case of Actmt-001f2-SHNL (FIG. 8A).

As a result of comparing the processes of the 11th reaction, the reaction rate of Actmt-001f2-SHNL was improved by approximately 10% (FIG. 8B). This may result from a possibility such that stability of the thermostable enzyme (Actmt-001f2-SHNL) in the enzyme reaction system was improved in addition to the heat tolerance.

3. Conclusion

Actmt-001f2-SHNL was found to be capable of synthesizing optically active cyanohydrin with the productivity and optical purity that were the same as those of Wild-SHNL. Further, approximately 10% of lifespan prolongation was observed via the repeated reactions.

EXAMPLE 6

Preparation of BL21(DE3)/pET21a/SHNL-G165E

In the thermostable enzyme Actmt-001f2-SHNL, position 165 of its amino acid sequence was substituted with an acidic amino acid (aspartic acid). The BL21(DE3)/pET21a/SHNL-G165E expression system for SHNL (nucleotide sequence: SEQ ID NO: 7; amino acid sequence: SEQ ID NO: 8) in which amino acid 165 had been substituted with an acidic amino acid (glutamic acid) was prepared.

1. Mutagenesis

In the same manner as in Example 1, the QuikChange XL Site-Directed Mutagenesis Kit (Stratagene) was used for modifying amino acid 165. The pET21a/SHNL-Wild plasmid (10 ng) was used as the template, and the following oligo DNA was used as primers to perform elongation. The resulting reaction product was digested with the DpnI restriction enzyme attached to the kit.

```
Forward primer:
                                      (SEQ ID NO: 13)
5'-CGT GAA AAC CTG TTC ACC AAA TGC ACT GAT GAA GAA

TAT GAA CTG GCA AAA ATG-3'

Reverse primer:
                                      (SEQ ID NO: 14)
5'-CAT TTT TGC CAG TTC ATA TTC TTC ATC AGT GCA TTT

GGT GAA CAG GTT TTC ACG-3'
```

2. Transformation

The resulting reaction product processed with restriction enzymes was applied to XL10-Gold competent cells attached to the kit for transformation, and the obtained cells were subjected to colony PCR. The resulting PCR product was used as the template for sequencing, and the reaction product was analyzed. Based on the analysis, a cell in which GC at positions 494 and 495 in the nucleotide sequence had been modified by AA was selected. The pET21a/SHNL-G165E plasmid was prepared therefrom, applied to BL21(DE3) competent cells (Novagen) for transformation, and the BL21 (DE3)/pET21a/SHNL-G165E expression system for SHNL, in which amino acid 165 had been substituted with Glu, was prepared.

EXAMPLE 7

Changes in Heat Tolerance Depending on Amino Acid Type at Substitution Site

The position 165 in the amino acid sequence of SHNL was substituted with various types of polar amino acids, and subsequent effect on heat tolerance of SHNL was examined.

1. Method of Experimentation

In accordance with Example 1 and Example 6, mutagenesis into 165-Gly was carried out using the QuikChange XL Site-Directed Mutagenesis Kit (Stratagene), and the following mutants were prepared.

i) DH5α/pKK223-3/Actmt001f2-Glu (substitution of amino acid 165 for glutamic acid)

ii) DH5 α/pKK223-3/Actmt001f2-Lys (substitution of amino acid 165 for lysine)

iii) DH5α/pKK223-3/Actmt001f2-Arg (substitution of amino acid 165 for arginine)

iv) DH5α/pKK223-3/Actmt001f2-Ala (substitution of amino acid 165 for alanine)

Glutamic acid is an amino acid having an acidic residue as with aspartic acid. Lysine and arginine are basic amino acids. Alanine is a neutral amino acid as with glycine. These four mutants, DH5α/pKK223-3/SHNL-Actmt001-f2, and SHNL-Wild (6 strains in total) were subjected to the heating test in the same manner as in Example 2.

2. Results of Experimentation

Figure 9:
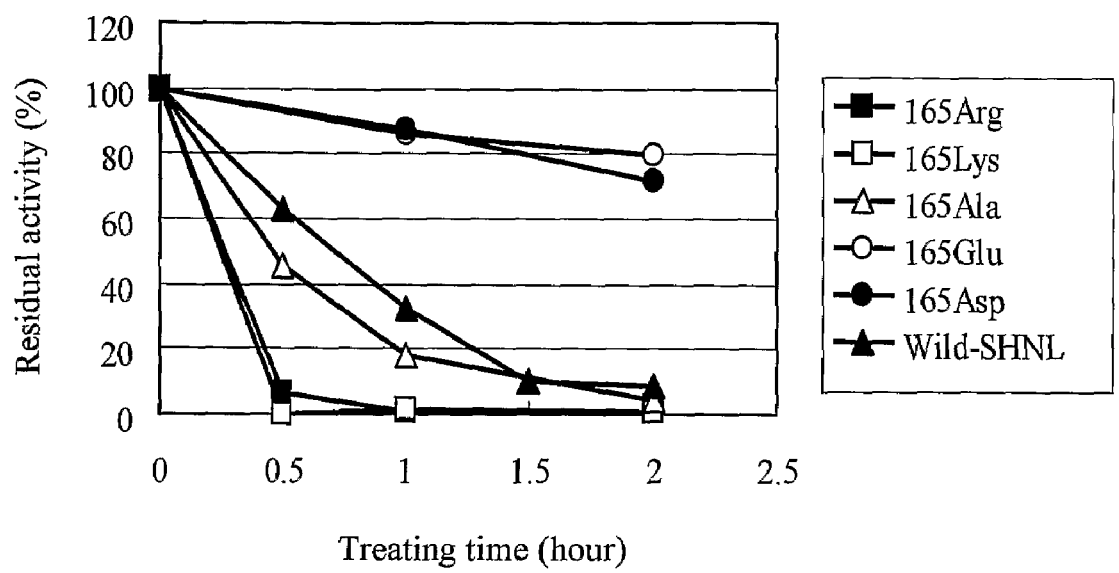
FIG. 9 is a graph showing changes in enzyme activities of various types of modified SHNL via heating.

As a result of the heating test in accordance with Example 2, the modified SHNL exhibited roughly 3 types of heat tolerances depending on different properties of amino acid residues that had been introduced (FIG. 9).

1) Substitution for Basic Amino Acid (Arg, Lys)

Activity of the modified SHNL substantially completely disappeared in 30 minutes. Heat tolerance was apparently deteriorated compared to that of Wild SHNL.

2) Substitution for Neutral Amino Acid (Ala)

Modified SHNL exhibited the heat tolerance equivalent to that of Wild SHNL (165-Gly, neutral).

3) Substitution for Acidic Amino Acid (Glu)

The activity level changed in the substantially same manner as with the case of Actmt-001f2-SHNL (165-Asp, acidic). The highest level of heat tolerance was exhibited among three types of amino acids.

As is apparent from the above results, heat tolerance of modified SHNL in which amino acid 165 had been substituted with an acidic amino acid was improved. In contrast, heat tolerance of modified SHNL in which amino acid 165 had been substituted with a basic amino acid was significantly deteriorated.

Figure 10:
FIG. 10 is a diagram showing the three-dimensional structure of SHNL (red: 165 Gly; black: 21 Lys).
Figure 11:
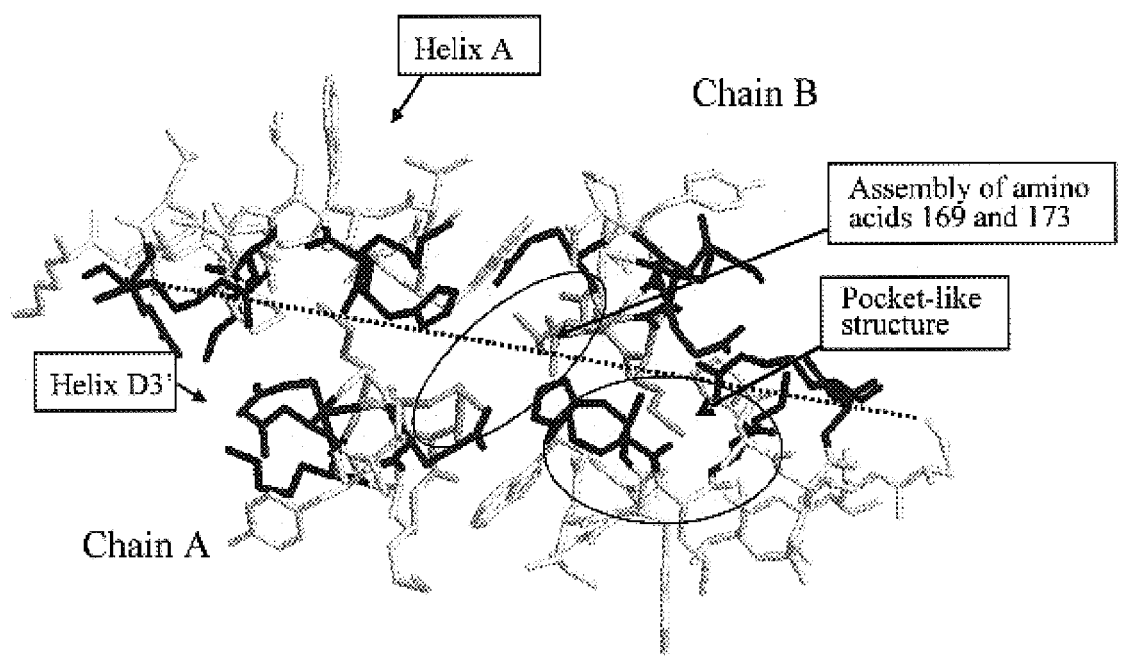
FIG. 11 is a diagram showing positions of amino acid side chains at the binding site of the SHNL dimer (red: acidic amino acid; blue: basic amino acid).

FIG. 10 shows a three-dimensional structure of SHNL, where a red portion indicates 165-Gly and a black portion indicates 21-Lys. SHNL is present as a homodimer. According to the report by Wagner et al. (Mechanism of cyanogenesis: the crystal structure of hydroxynitrile lyase from *Hevea brasilinsis*, Structure, 1996, vol. 4, No. 7), 165-Gly is a constituent amino acid of a helix referred to as "D3' (162-173)." D3' is a domain that binds to the helix A (15-28) domain and the β-sheet 2 (32-36) domain of another SHNL monomer when SHNL forms a dimer. Substitution from glycine to aspartic acid causes D3' to be negatively charged, it enhances the binding strength of helix A and β-sheet 2 to positive amino acid residues (20-His, 21-Lys, and 23-Lys), and it stabilizes dimer formation. These phenomena were considered to partially contribute to improvement in heat tolerance.

EXAMPLE 8

Modification of Helix D3'

Preparation of BL21(DE3)/pET21a/SHNL-SD173-1e9

Amino acids 165 to 173 of helix D3' (163-174) are positioned crosswise to amino acids 17 to 21 of helix A, and they are adjacent to each other. Amino acid substitution in such regions can influence the level of heat tolerance. Thus, amino acid 173 of the amino acid sequence of SHNL was substituted from Val to Leu, and the resulting influences on thermostability of SHNL were examined.

1. Mutagenesis

In accordance with Example 1 and Example 6, SHNL (SEQ ID NO: 16) in which amino acid 173 had been substituted with Leu was prepared using the QuikChange XL Site-Directed Mutagenesis Kit (Stratagene).

Elongation reaction was carried out using the pET21a-SHNL-Wild plasmid (10 ng) as the template and the following oligo DNA as primers. Subsequently, the resulting reaction product was digested with the DpnI restriction enzyme attached to the kit.

```
Forward primer:
                                        (SEQ ID NO: 17)
5'-GGC GAA TAT GAA CTG GCA AAA ATG NNN ATG CGC AAG

GGC TCT CTG-3'

Reverse primer:
                                        (SEQ ID NO: 18)
5'-CAG AGA GCC TTT GCG CAT NNN CAT TTT TGC CAG TTC

ATA TTC GCC-3'
```

2. Transformation and Heat Tolerance Assay

The resulting reaction product processed with restriction enzymes was applied to XL10-Gold competent cells attached to the kit for transformation, and all the obtained colonies formed on an LB (Amp) plate were suspended in LB (Amp) liquid medium. The pET21a/SHNL-SD173-1NNNMutants plasmid were prepared from the resulting suspension and then add to BL21(DE3) competent cells (Novagen) for transformation to prepare BL21(DE3)/pET21a/SHNL-SD173-1NNNMutants strains.

Multiple BL21(DE3)/pET21a/SHNL-SD173-1NNNMutants strains were cultured in test tubes, 1 ml each of the culture broth was fractionated, the fractionated culture broth was centrifuged to remove the supernatant, and cell pellets were obtained. The obtained cells were resuspended in 200 μl of sodium citrate buffer (pH 5.5) and then disrupted via an ultrasonic cell homogenizer. The disrupted cells were centrifuged at 15,000 rpm for 5 minutes to obtain a solution of disrupted cells. This solution of disrupted cells was heated at 60° C. for 2 hours, and SHNL activity of the solution was then assayed. On the basis of the assay result, the BL21(DE3)/ pET21a/SHNL-SD173-1e9 and other 3 strains that were still active after heating were selected as thermostable strains. The selected strains were subjected to colony PCR, and the resulting PCR product was used as the template for sequencing. Based on the results of analyzing the reaction product, SHNL-SD173-1e9 was found to have a nucleotide sequence (SEQ ID NO: 15) in which amino acids 517 to 519, i.e., GTT(V), of the nucleotide sequence had been modified to CTG(L) and amino acid 173 had been substituted from valine to leucine. Hereafter, SHNL-SD173-1e9 is referred to as SHNL-V173L. All of the other three strains were found to be mutants in which amino acid 173 had been substituted from valine to leucine.

EXAMPLE 9

Evaluation of Heat Tolerance of V173L-SHNL

Thermostability of V173-SHNL was compared with that of Wild-SHNL and that of Actmt001-f2-SHNL.

1. Method of Experimentation

1) Preparation of Enzyme Solution

E. coli strains, i.e., BL21(DE3)/pET21a/SHNL-Wild, BL21(DE3)/pET21a/SHNL-Actmt001-f2, and BL21(DE3)/pET21a/SHNL-V173L, were cultured in the same manner as in Example 2 to obtain enzyme solutions. The aforementioned samples were diluted with bovine serum albumin and a buffer, all the samples were adjusted to have an activity level of 17.6 U/ml, a specific activity level of 4.5 U/mg, and the protein concentration of 3.9 mg/ml, and influences of contaminating proteins were eliminated from the experimentation system.

2) Heat Treatment of Enzyme Solution

Figure 14:
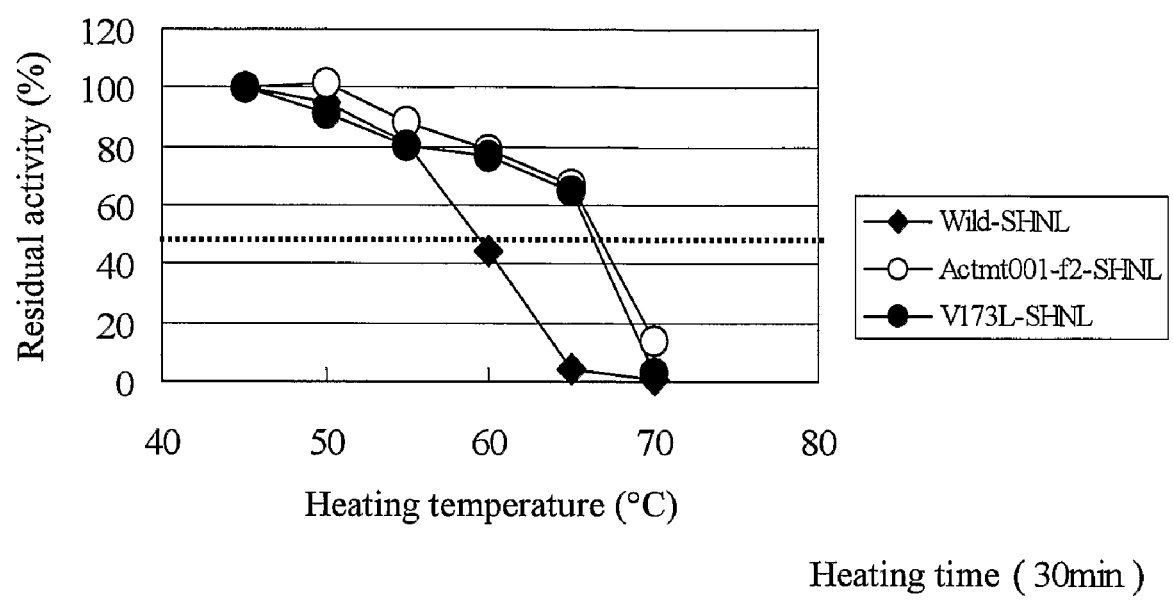
FIG. 14 is a graph showing the results of comparing thermostability of Wild-SHNL, that of Actmt-001f2-SHNL, and that of V173L-SHNL.

The enzyme solutions of Wild-SHNL, Actmt001-f2-SHNL, and V173L-SHNL (200 µl each) were placed in Eppendorf tubes and the enzyme solutions were heated to 45° C. to 70° C. in a heat block. After the heat treatment of 30 minutes, the samples were recovered by centrifugation, and the level of residual activity was assayed (FIG. 14).

As a result, the temperature at which enzyme activity of the sample was reduced to half the original level was 60° C. in the case of Wild-SHNL, and that of V173L-SHNL and that of Actmt001-f2-SHNL were around 65° C., which indicates that these samples had improved heat tolerance by approximately 5° C. from Wild-SHNL. Thus, V173L-SHNL was found to have heat tolerance that was equivalent to that of Actmt001-2-SHNL.

Amino acid 173 of SHNL, i.e., valine, is adjacent to the amino acid of another monomer, i.e., valine, at the time of dimer formation (the distance between terminuses is approximately 4.5 angstroms). Substitution from valine to leucine results in extension of amino acid residue 173 by one carbon. Accordingly, the distance between residues can become narrow when carbon chains elongate, and hydrophobic interaction between non-polar amino acid residues can be reinforced.

EXAMPLE 10

Organic Solvent Tolerance of Modified Enzyme V173L-SHNL

As mentioned in Example 4, ethanol tolerance and ethyl acetate tolerance of the thermostable modified enzyme (Actmt001-f2-SHNL) were superior to those of Wild-SHNL.

The modified enzyme (V173L-SHNL) mentioned in Example 9 has thermostability that is substantially the same as that of Actmt001-f2-SHNL. Thus, tolerance of V173L-SHNL to ethanol and to ethyl acetate was also examined.

1. Method of Experimentation

1) Preparation of Enzyme Solution

E. coli strains, i.e., BL21(DE3)/pET21a/SHNL-Wild, BL21(DE3)/pET21a/SHNL-Actmt001-f2, and BL21(DE3)/pET21a/SHNL-V173L, were cultured in the same manner as in Example 2 to prepare enzyme solutions. The prepared enzyme solutions were diluted with bovine serum albumin and a 0.2M sodium citrate buffer, all the samples were adjusted to have an activity level of 45 U/ml and a specific activity level of 6.5 U/mg, and influences of contaminating proteins were eliminated from the experimentation system.

2) Organic Solvent Treatment

The enzyme solutions were treated with ethanol and with ethyl acetate in the same manner as in Example 4, and the residual activity was assayed.

2. Result of Experimentation

V173L-SHNL was found to be more tolerant to ethanol (FIG. 15A) and to ethyl acetate (FIG. 15B) than Wild-SHNL. Further, V173L-SHNL was more tolerant to ethanol than Actmt001-f2-SHNL. While the residual activity after 16 hours treatment of Actmt001-f2-SHNL was 23%, V173L-SHNL was 34%, respectively. Tolerances of two types of modified enzymes to ethyl acetate were at the substantially same level.

EXAMPLE 11

Acquisition of Modified Enzyme Actmt020-b8-SHNL

1. Mutagenesis

In the same manner as in Example 1, mutagenesis into the Wild-SHNL gene was carried out using the GeneMorph™ PCR Mutagenesis Kit. The template and the primers employed in Example 1 were employed.

2. Transformation

In the same manner as in Example 1, the resulting PCR product was ligated to the pKK223-3 vector and applied to DH5α competent cells for transformation to obtain a plurality of DH5α/pKK223-3/SHNL-Actmt020 strains.

3. Selection of Thermostable Enzyme and Sequence Analysis

In the same manner as in Example 1, the DH5α/pKK223-3/SHNL-Actmt020-b8 strain that had been still active after heating was selected. Colony PCR was carried out using primers as shown in SEQ ID NO: 9 and SEQ ID NO: 10 and the selected strain was used as the template. Further, sequencing was carried out using the resulting PCR product as the template and the same primers. The analysis of the reaction product demonstrated that SHNL-Actmt020-b8 had a nucleotide sequence (SEQ ID NO: 19) derived from the nucleotide sequence as shown in SEQ ID NO: 1 by modification of amino acid 520 from adenine to thymine. Accordingly, it was verified that SHNL-Actmt020-b8 was a modified SHNL having an amino acid sequence (SEQ ID NO: 20) derived from the amino acid sequence of Wild-SHNL (SEQ ID NO: 2) by substitution of amino acid 174 from methionine to leucine. Hereafter, this modified SHNL is referred to as "Actmt020-b8-SHNL."

EXAMPLE 12

Thermostability of Modified Enzyme Actmt020-b8-SHNL

1. Method of Experimentation

1) Preparation of Enzyme Solution

The *E. coli* strain, DH5α/pKK223-3/SHNL-Actmt020-b8, which had been constructed in Example 11, and the DH5α/pKK223-3/SHNL-Wild strain as a control were both cultured in the same manner as in Example 2 to prepare enzyme solutions. The prepared enzyme solutions were diluted with bovine serum albumin and a 0.2M sodium citrate buffer, all the samples were adjusted to have an activity level of 3.15 U/ml and the protein concentration of 1.38 mg/ml, and influences of contaminating proteins were eliminated from the experimentation system.

2) Heat Treatment of Enzyme Solution

The enzyme solutions were heated to 60° C. in the same manner as in Example 3. The solutions were centrifuged every 30 minutes after the initiation of heating, and the supernatant was subjected to assay of residual activity in relation to the enzyme activity before heating.

2. Result of Experimentation

Figure 16:
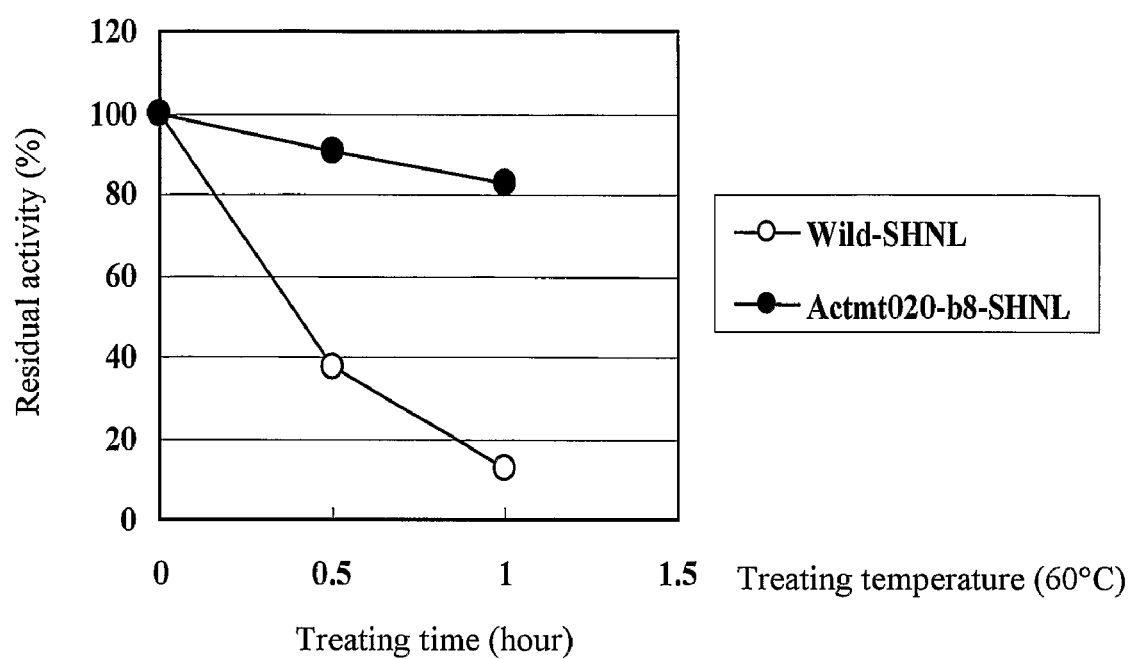
FIG. 16 is a graph showing the thermostability of modified enzyme Actmt0020-b8-SHNL.

Actmt020-b08-SHNL exhibited significantly improved thermostability compared to that of Wild-SHNL (FIG. 16). Thus, it was found that substitution of amino acid 174 that constitutes helix D3' from methionine to leucine could improve the thermostability of SHNL.

EXAMPLE 13

Acquisition of Modified Enzyme Actmt022-g12-SHNL

1. Mutagenesis

In the same manner as in Example 1, mutagenesis into the Wild-SHNL gene was carried out using the GeneMorph™ PCR Mutagenesis Kit. The template and the primers employed in Example 1 were employed.

2. Transformation

In the same manner as in Example 1, the resulting PCR product was ligated to the pKK223-3 vector and applied to DH5 α competent cells for transformation to obtain a plurality of DH5α/pKK223-3/SHNL-Actmt022 strains.

3. Selection of Thermostable Enzyme and Sequence Analysis

In the same manner as in Example 1, the DH5α/pKK223-3/SHNL-Actmt022-g12 strain that had been still active after heating was selected. Colony PCR was carried out using primers as shown in SEQ ID NO: 9 and SEQ ID NO: 10 and the selected strain was used as the template. Further, sequencing was carried out using the resulting PCR product as the template and the same primers. The analysis of the reaction product demonstrated that SHNL-Actmt022-g12 had a nucleotide sequence (SEQ ID NO: 21) derived from the nucleotide sequence as shown in SEQ ID NO: 1 by modification of amino acid 63 from adenine to thymine. Accordingly, it was verified that Actmt022-g12-SHNL was a modified SHNL having an amino acid sequence (SEQ ID NO: 22) derived from the amino acid sequence of Wild-SHNL (SEQ ID NO: 2) by substitution of amino acid 21 from lysine to asparagine. Lysine at position 21 in the amino acid sequence was an amino acid that constitutes helix A where a dimer is formed.

EXAMPLE 14

Construction of Modified Enzyme with Amino Acid Substitution at Lys-21

The position 21 in the amino acid sequence of SHNL was substituted with various types of amino acids, and influences thereof on heat tolerance of SHNL were examined.

1) Mutagenesis

In the same manner as in Example 8, the QuikChange XL Site-Directed Mutagenesis Kit (Stratagene) was employed. Extension reaction was carried out using 10 ng of pET21a/SHNL-Wild as the template and primers as shown in SEQ ID NO: 23 and in SEQ ID NO: 24. Subsequently, the resulting reaction product was digested with the DpnI restriction enzyme attached to the kit.

2) Transformation

The resulting reaction product processed with restriction enzymes was applied to XL10-Gold competent cells attached to the kit for transformation and then cultured on an LB (Amp) plate. The resulting colonies formed on the plate were resuspended in LB (Amp) liquid medium to prepare the pET21a/SHNL-SDLys21NNN plasmid. This plasmid was applied to BL21(DE3) competent cells (Novagen) for transformation to prepare a plurality of BL21(DE3)/pET21a/SHNL-SDLys21NNN strains.

3) Selection of Modified SHNL

The prepared *E. coli* BL21(DE3)/pET21a/SHNL-SDLys21NNN strains were cultured in the same manner as in Example 2. The resulting culture broths were employed to select modified strains having improved thermostability in accordance with the method of Example 1. As a result, three types of modified strains, i.e., BL21(DE3)/pET21a/SHNL-SDLys21-RAM1, BL21(DE3)/pET21a/SHNL-SDLys21-RAM6, and BL21(DE3)/pET21a/SHNL-SDLys21-RAM8, were found to be active after heating. Subsequently, colony PCR was carried out using primers as shown in SEQ ID NO: 9 and in SEQ ID NO: 10 and the selected strains as templates. Further, sequencing was carried out using the resulting PCR product as the template and the same primers. The analysis of the reaction product demonstrated that SHNL-SDLys21-RAM1 had a nucleotide sequence (SEQ ID NO: 25) derived from the nucleotide sequence as shown in SEQ ID NO: 1 by substitution of amino acid 61 from adenine to guanine. Accordingly, it was verified that SDLys21-RAM1-SHNL was a modified SHNL having an amino acid sequence (SEQ ID NO: 26) derived from the amino acid sequence of Wild-SHNL (SEQ ID NO: 2) by substitution of amino acid 21 from lysine to glutamic acid. Similarly, SHNL-SDLys21-RAM6 had a nucleotide sequence (SEQ ID NO: 27) derived from the nucleotide sequence as shown in SEQ ID NO: 1 by substitution of amino acid 61 to 63 from AAA to GAC. Accordingly, it was verified that SDLys21-RAM6-SHNL was a modified SHNL having an amino acid sequence (SEQ ID NO: 28) derived from the amino acid sequence of Wild-SHNL (SEQ ID NO: 2) by substitution of amino acid 21 from lysine to aspartic acid. Further, SHNL-SDLys21-RAM8 had a nucleotide sequence (SEQ ID NO: 29) derived from the nucleotide sequence as shown in SEQ ID NO: 1 by substitution of amino acid 63 from adenine to cytosine. Accordingly, it was verified that SDLys21-RAM8 SHNL was a modified SHNL having an amino acid sequence (SEQ ID NO: 30) derived from the amino acid sequence of Wild-SHNL (SEQ ID NO: 2) by substitution of amino acid 21 from lysine to asparagine. Hereafter, SDLys21-RAM1 SHNL is referred to as "K21E-

SHNL," RAM6 is referred to as "K21D-SHNL," and RAM8 is referred to as "K21N-SHNL."

EXAMPLE 15

Heat Tolerance of Modified Enzymes K21E-SHNL, K21D-SHNL, and K21N-SHNL

1. Method of Experimentation

1) Preparation of Enzyme Solution

The *E. Coli* strains, BL21(DE3)/pET21a/SHNL-K21E, BL21(DE3)/pET21a/SHNL-K21D, and BL21(DE3)/pET21a/SHNL-K21N, constructed in Example 14 and the BL21(DE3)/pET21a/SHNL-Wild strain as a control were cultured in the same manner as in Example 2 to prepare enzyme solutions. The prepared enzyme solutions were diluted with bovine serum albumin and a 0.2M sodium citrate buffer, all the samples were adjusted to have an activity level of 11 U/ml and a protein concentration of 6.8 mg/ml, and influences of contaminating proteins were eliminated from the experimentation system.

2) Heat Treatment of Enzyme Solution

The enzyme solutions were heated to 45° C. to 65° C. in the same manner as in Example 2. After the heat treatment of 30 minutes, the solutions were centrifuged, and the supernatant was subjected to assay of residual activity in relation to the enzyme activity before heating.

2. Result of Experimentation

Figure 17:
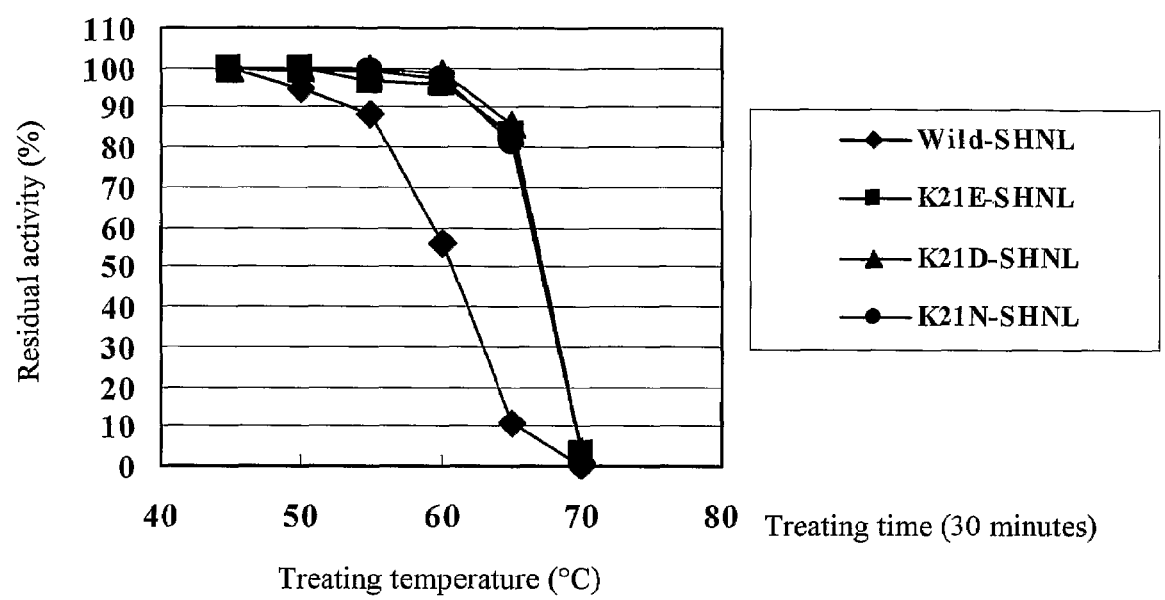
FIG. 17 is a graph showing the thermostability of Lys-21 modified enzyme.

K21E-SHNL, K21D-SHNL, and K21N-SHNL exhibited significantly improved thermostability compared to that of Wild-SHNL (FIG. 17). Thus, it was found that substitution of amino acid 21 that constitutes helix A from lysine to glutamic acid, aspartic acid, or asparagine could improve thermostability of SHNL.

EXAMPLE 16

Preparation of SHNL Genes, i.e., SHNL-G165E, V173L and SHNL-G165E, V173L, M174L, Having Multiple Modification Sites Modified SHNL, i.e., Actmt001-f2-SHNL, V173L-SHNL, and Actmt020-b8-SHNL, each independently possessed a single amino acid modification site. Further their heat and organic solvent tolerance were superior to those of Wild-SHNL. In order to further improve heat tolerance and organic solvent tolerance, modification sites of individual strains of these strains were introduced in combination to a single gene.

1. Construction of SHNL Gene, i.e., SHNL-G165E, V173L, Having Multiple Modification Sites 1) Mutagenesis In the same manner as in Example 8, the QuikChange XL Site-Directed Mutagenesis Kit (Stratagene) was employed. Extension reaction was carried out using 10 ng of pET21a/SHNL-SD173-1e9 plasmid as the template and primers as shown in SEQ ID NO: 13 and in SEQ ID NO: 14. Subsequently, the resulting reaction product was digested with the DpnI restriction enzyme attached to the kit.

2) Transformation

The resulting reaction product processed with restriction enzymes was applied to XL10-Gold competent cells attached to the kit for transformation. The resulting colonies formed on the LB (Amp) plate were recovered and then cultured in LB (Amp) liquid medium at 37° C. for 12 hours. Plasmids were isolated from the culture broth and extension reaction was carried out using the resulting plasmids as the template and primers as shown in SEQ ID NO: 9 and in SEQ ID NO: 10. Further, sequencing was carried out using the resulting reaction product as the template and the same primers. According to the results of analyzing the reaction product, the pET21a/SHNL-G165E, V173L plasmid having the SHNL genes (nucleotide sequence: SEQ ID NO: 31; amino acid sequence: SEQ ID NO: 32) with 2 amino acid mutations (Gly-to-Glu at position 165 and Val-to-Leu at position 173) were selected. The selected plasmid was applied to BL21(DE3) competent cells (Novagen) for transformation to prepare the BL21(DE3)/pET21a/SHNL-G165E, V173L strain.

2. Construction of SHNL Gene, i.e., SHNL-G165E, V173L, M174L, Having Multiple Modification Sites 1) Mutagenesis In the same manner as in Example 8, the QuikChange XL Site-Directed Mutagenesis Kit (Stratagene) was employed. The extension reaction was carried out using 10 ng of pET21a/SHNL-G165E, V173L plasmid as the template and primers as shown in SEQ ID NO: 33 and in SEQ ID NO: 34. Subsequently, the resulting reaction product was digested with the DpnI restriction enzyme attached to the kit.

2) Transformation

The resulting reaction product processed with restriction enzymes was applied to XL10-Gold competent cells attached to the kit for transformation. The resulting colonies formed on the LB (Amp) plate were recovered and then cultured in LB (Amp) liquid medium at 37° C. for 12 hours. Plasmids were isolated from the culture solution and extension reaction was carried out using the resulting plasmids as the template and primers as shown in SEQ ID NO: 9 and in SEQ ID NO: 10. Further, sequencing was carried out using the resulting reaction product as the template and the same primers. According to the results of analyzing the reaction product, the pET21a/SHNL-G165E, V173L, M174L plasmid having the SHNL genes (nucleotide sequence: SEQ ID NO: 35; amino acid sequence: SEQ ID NO: 36) with 3 amino acid mutations (Gly-to-Glu at position 165, Val-to-Leu at position 173, and Met-to-Leu at position 174) was selected. The selected plasmid was applied to BL21(DE3) competent cells (Novagen) for transformation to prepare the BL21(DE3)/pET21a/SHNL-G165E, V 173L, M 174L strain.

EXAMPLE 17

Thermostability of SHNL Genes, i.e., G165E, V173L, M174L-SHNL and G165E, V173L, M174L-SHNL, Having Multiple Mutation Sites 1. Method of Experimentation 1) Preparation of Enzyme Solution The *E. coli* strains, i.e., BL21(DE3)/pET21a/SHNL-G165E, BL21(DE3)/pET21a/SHNL-V173L, BL21(DE3)/pET21a/SHNL-G165E, BL21(DE3)/pET21a/SHNL-V173L, BL21(DE3)/pET21a/SHNL-M174L, constructed in Example 16 and BL21(DE3)/pET21a/SHNL-Wild, were cultured in the same manner as in Example 2 to prepare enzyme solutions. The prepared enzyme solutions were diluted with bovine serum albumin and a 0.2M sodium citrate buffer, all the samples were adjusted to have an activity level of 70 U/ml and a protein concentration of 6 mg/ml, and influences of contaminating proteins were eliminated from the experimentation system.

2) Heat Treatment of Enzyme Solution

The enzyme solutions were heated to 45° C. to 75° C. in the same manner as in Example 2. After the heat treatment of 30 minutes, the enzyme solutions were centrifuged, and the supernatant was subjected to assay of residual activity in relation to the enzyme activity before heating.

2. Result of Experimentation

Figure 18:
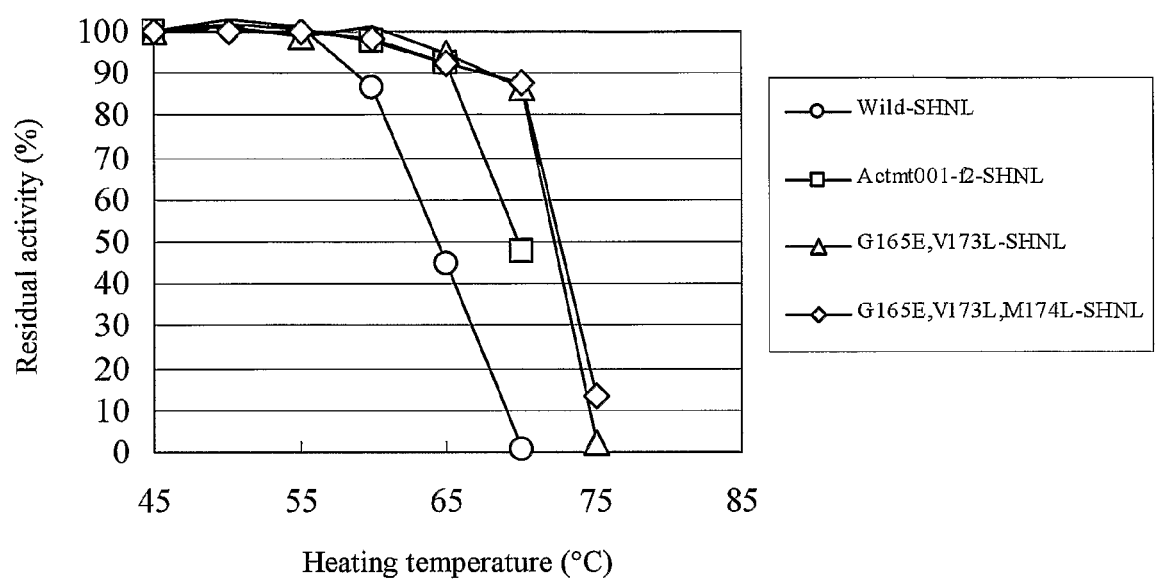
FIG. 18 is a graph showing the thermostability of SHNL having multiple modification sites.

G165E, V173L-SHNL and G165E, V173L, M174L-SHNL exhibited significantly improved thermostability compared to that of Wild-SHNL and the level of residual activities at 70° C. was approximately 90% in both cases (FIG. 18). In the case of G165E, V173L-SHNL, the activity level was rapidly inactivated at 75° C. and the level of residual activity was 2%. G165E, V173L, M174L-SHNL with 3 modification sites remained 13% of its activity at 75° C. Thus, it was found that thermostability could be further improved by aggregating modification sites of individual strains on a single gene.

EXAMPLE 18

Organic Solvent Tolerance of SHNL Genes, i.e., SHNL-G165E, V173L-SHNL and G165E, V173L, M174L-SHNL, Having Multiple Substitution Sites 1. Method of Experimentation 1) Preparation of Enzyme Solution The *E. coli* strains, i.e., BL21(DE3)/pET21a/SHNL-Wild, BL21(DE3)/pET21a/SHNL-G165E, V173L, and BL21 (DE3)/pET21a/SHNL-G165E, V173L, M174L, were cultured in the same manner as in Example 2 to prepare enzyme solutions. The prepared enzyme solutions were diluted with bovine serum albumin and a 0.2M sodium citrate buffer, all the samples were adjusted to have an activity level of 45 U/ml and a specific activity level of 6.5 mg/ml, and influences of contaminating proteins were eliminated from the experimentation system.

2) Organic Solvent Treatment

The enzyme solutions were treated with ethanol and with ethyl acetate in the same manner as in Example 4, and the residual activity was assayed.

2. Result of Experimentation

Figure 19:
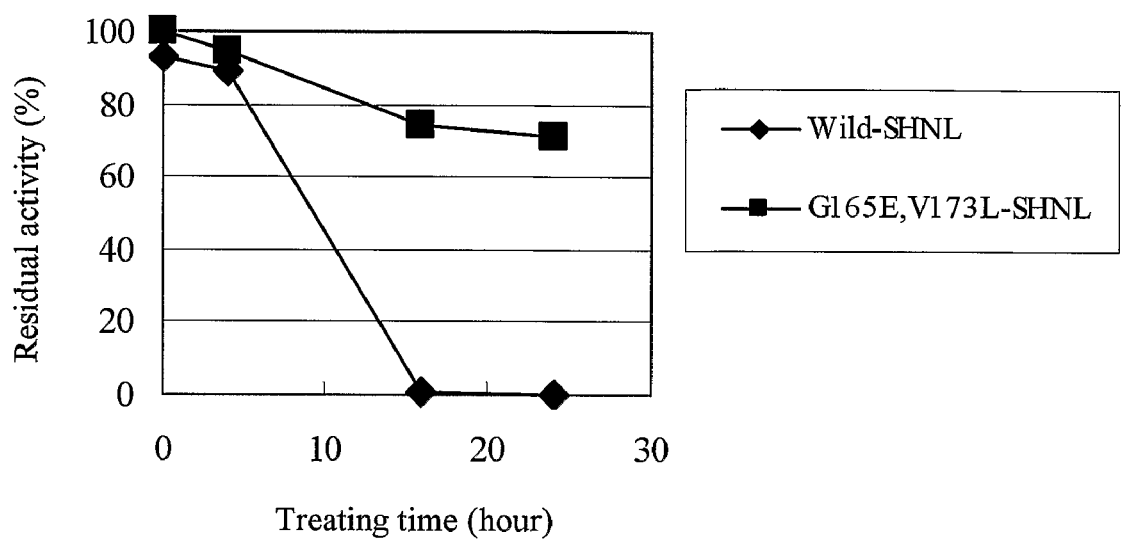
FIG. 19 is a graph showing ethanol tolerance of G165E, V173L-SHNL.

The enzyme solutions were treated with ethanol. As a result, activity of Wild-SHNL substantially disappeared 16 hours after the initiation of treatment. However, G165E, V173-SHNL having multiple substitution sites retained its activity as much as 73% (FIG. 19). As mentioned in Example 4 and in Example 11, Actmt001-f2, V173L-SHNL having a single amino acid mutation retained 20% to 30% of tolerance to ethanol after 16 hours of treatment. Thus, ethanol tolerance of SHNL having multiple substitution sites was found to be significantly improved.

Figure 20:
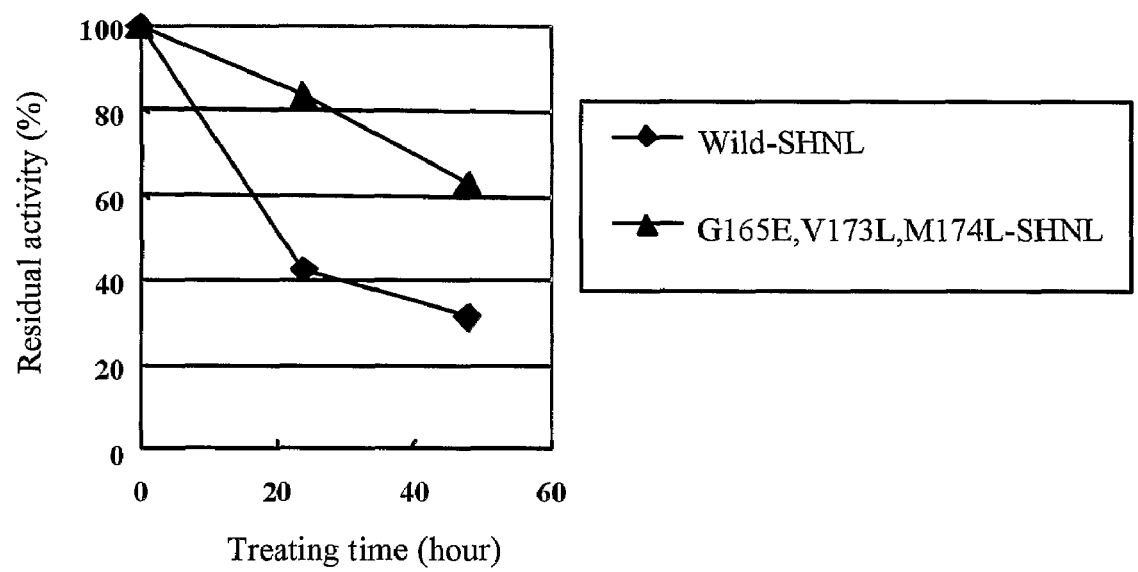
FIG. 20 is a graph showing ethyl acetate tolerance of G165E, V173L, M174L-SHNL.

With the use of ethyl acetate, G165E, V173L, M174L-SHNL retained its activity as much as 80% after 24 hours of treatment (FIG. 20). As with the case of ethanol tolerance, organic solvent tolerance was significantly improved via aggregation of modification sites of individual strains.

EXAMPLE 19

Synthesis of Optically Active Cyanohydrin using G165E, V173-SHNL Enzyme Having Multiple Modification Sites Optically active cyanohydrin was repeatedly synthesized using the multiple modification site bearing G165E, V173-SHNL enzyme. Stability in the enzyme reaction system was examined. Modification may alter substrate specificity or may deteriorate the capacity for asymmetric synthesis. Optically active cyanohydrin can be produced by common SHNL. Accordingly, this phenomenon was examined in the case at hand.

1. Method of Experimentation

1) Preparation of Enzyme Solution

The *E. coli* strains, BL21(DE3)/pET21a/SHNL-Wild and BL21(DE3)/pET21a/SHNL-G165E, V173L, were cultured in the same manner as in Example 2 to prepare enzyme solutions. Further, a sodium citrate buffer (pH 5.5) was added to these enzyme solutions to adjust the activity levels to 500 U/ml. BSA was added to the G165E, V173-SHNL enzyme solution to bring the total protein concentration to the same level as that of Wild-SHNL. Silica gel (300 mg) was mixed with 0.3 ml of such enzyme solution to obtain immobilized enzymes.

2) Enzyme Reaction

Enzyme reaction was carried out under the reaction conditions described in Example 5. 2-Chlorobenzaldehyde (2CBA) was used as a reaction substrate at the final concentration of 1.0M instead of benzaldehyde. The samples were recovered every hour, and the 2CBA concentration of the reaction solution and the concentration of (R/S)-2-chloro-mandelonitrile were assayed. The time period at which the conversion rate of 2-chlorobenzaldehyde exceeded 95% was defined as the completion of reaction, and 4 ml of the reaction solution was recovered after the completion of the reaction. Subsequently, the same amount of HCN/t-butyl methyl ether solution, which had been subjected to the same processing, was added, and the same amount of benzaldehyde was added to perform the second enzyme reaction. At the second and later reaction cycles, 5 ml of the reaction solution was recovered after the completion of the reaction. This enzyme reaction was repeated 4 times.

2. Result of Experimentation

1) Optical Purity

G165E, V173L-SHNL produced (S)-2-chloromandelonitrile with optical purity of 95% ee on average through 4 repeated reactions. Similarly, Wild-SHNL exhibited optical purity of approximately 95% ee. Accordingly, G165E, V173L-SHNL was found to have the capacity of producing optically active cyanohydrin, which is substantially the same as that of Wild-SHNL in terms of optical purity.

2) Comparison of Reaction Rate and Degree of Activity Decrease

Figure 21:
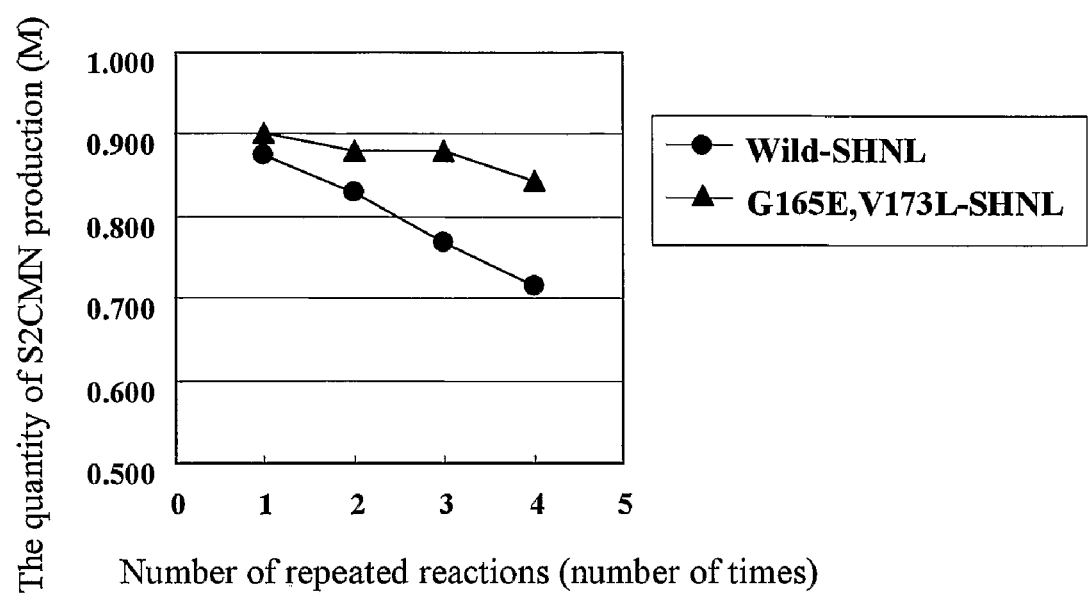
FIG. 21 is a graph showing the amount of 2CMN produced 1 hour after the initiation of repetitive reactions using G165E, V173L, M174L-SHNL.

G165E, V173L-SHNL produced (S)-2-chloromandelonitrile at the same reaction rate with wild-SHNL in the first reaction. Accordingly, G165E, V173L-SHNL was found to have the capacity of producing optically active cyanohydrin, which is substantially the same as that of Wild-SHNL in terms of productivity. As the number of repetition of reactions increased, enzyme activity and reaction rate of both strains were lowered. However, the degree of lowering for G165E, V173L-SHNL was apparently milder than that for Wild-SHNL (FIG. 21). Thus, G165E, V173L-SHNL was found to have improved stability in the enzyme reaction system as well as improved heat tolerance.

EXAMPLE 20

Construction of Modified Enzyme in which Amino Acid 163 (Thr) had Been Modified

The position 163 in the amino acid sequence of SHNL was substituted with various types of amino acids, and influences thereof on thermostability of SHNL were examined.

1) Mutagenesis

In the same manner as in Example 8, the QuikChange XL Site-Directed Mutagenesis Kit (Stratagene) was employed. Extension reaction was carried out using 10 ng of pET21a/SHNL-Wild as the template and primers as shown in SEQ ID NO: 37 and in SEQ ID NO: 38. Subsequently, the resulting reaction product was digested with the DpnI restriction enzyme attached to the kit.

2) Transformation

The resulting reaction product processed with restriction enzymes was applied to XL10-Gold competent cells attached to the kit for transformation and then cultured on an LB (Amp) plate. The resulting colonies formed on the plate were resuspended in LB (Amp) liquid medium to isolate the pET21a/SHNL-SDThr163NNN plasmid. This plasmid was applied to BL21(DE3) competent cells (Novagen) for transformation to prepare a plurality of BL21(DE3)/pET21a/SHNL-SDThr163NNN strains.

3) Selection of Modified SHNL

The prepared E. coli BL21(DE3)/pET21a/SHNL-SDThr163NNN strains were cultured in the same manner as in Example 2. The resulting culture broths were employed to select modified strains having improved heat tolerance in accordance with the method of Example 1. As a result, modified strains, i.e., BL21(DE3)/pET21a/SHNL-SD163-1b5, BL21(DE3)/pET21a/SHNL-SD163-1f5, and BL21(DE3)/pET21a/SHNL-SD163-1f7, were found to be still active after heating. Subsequently, colony PCR was carried out using the following primers and the selected strains as the template. Further, sequencing was carried out using the resulting PCR product as the template and the same primers.

```
Forward primer:
                                        (SEQ ID NO: 37)
5'-TGAAAACCTGTTCACCAAATGCNNNGATGGCGAATATGAACTGG
C-3'

Reverse primer:
                                        (SEQ ID NO: 38)
5'-GCCAGTTCATATTCGCCATCNNNGCATTTGGTGAACAGGTTTTC
A-3'
```

The analysis of the reaction product demonstrated that SD163-1b5-SHNL had a nucleotide sequence (SEQ ID NO: 39) derived from the nucleotide sequence as shown in SEQ ID NO: 1 by substitution of amino acids 487 to 489 to GAT. Accordingly, it was verified that SD163-1b5-SHNL was a modified SHNL having an amino acid sequence (SEQ ID NO: 40) derived from the amino acid sequence of Wild-SHNL (SEQ ID NO: 2) by substitution of amino acid 163 from threonine to aspartic acid. Similarly, SD163-1f5-SHNL had a nucleotide sequence (SEQ ID NO: 41) derived from the nucleotide sequence as shown in SEQ ID NO: 1 by modification of amino acids 487 to 489 to GAA. Accordingly, it was verified that SD163-1f5-SHNL was a modified SHNL having an amino acid sequence (SEQ ID NO: 42) derived from the amino acid sequence of Wild-SHNL (SEQ ID NO: 2) by substitution of amino acid 163 from threonine to glutamic acid. Further, SHNL-SD163-1f7 has a nucleotide sequence (SEQ ID NO: 43) derived from the nucleotide sequence as shown in SEQ ID NO: 1 by modification of amino acid 487 to 489 to TCT. Accordingly, it was verified that SD163-1f7 SHNL was a modified SHNL having an amino acid sequence (SEQ ID NO: 44) derived from the amino acid sequence of Wild-SHNL (SEQ ID NO: 2) by substitution of amino acid 163 from threonine to serine.

Hereafter, SD163-1b5-SHNL is referred to as "T165D-SHNL," SD163-1f5-SHNL is referred to as "T163E-SHNL," and SD163-1f7-SHNL is referred to as "T163S-SHNL."

EXAMPLE 21

Thermostability of Modified Enzymes, i.e., T163D-SHNL, T163E-SHNL, and T163S-SHNL 1. Method of Experimentation 1) Preparation of Enzyme Solution The E. coli strains, BL21(DE3)/pET21a/SHNL-T163D, BL21(DE3)/pET21a/SHNL-T163E, and BL21(DE3)/pET21a/SHNL-T163S, which had been constructed in Example 20, were cultured in the same manner as in Example 2 to prepare enzyme solutions. Further, the prepared enzyme solutions were diluted with bovine serum albumin and a 0.2M sodium citrate buffer, BL21(DE3)/pET21a/SHNL-T163D and BL21(DE3)/pET21a/SHNL-T163E were adjusted to have an activity level of 70 U/ml and a protein concentration of 7 mg/ml. BL21(DE3)/pET21a/SHNL-T163S was adjusted to have an activity level of 70 U/ml and a protein concentration of 14 mg/ml. As a control, BL21(DE3)/pET21a/SHNL-Wild that had adjusted to the same concentration was employed.

2) Heat Treatment of Enzyme Solution

The enzyme solutions were heated to 50° C. to 70° C. in the same manner as in Example 2. The enzyme solutions were centrifuged 30 minutes after initiating heating, and the supernatant was subjected to assay of residual activity in relation to the enzyme activity before heating.

2. Result of Experimentation

Figure 12:
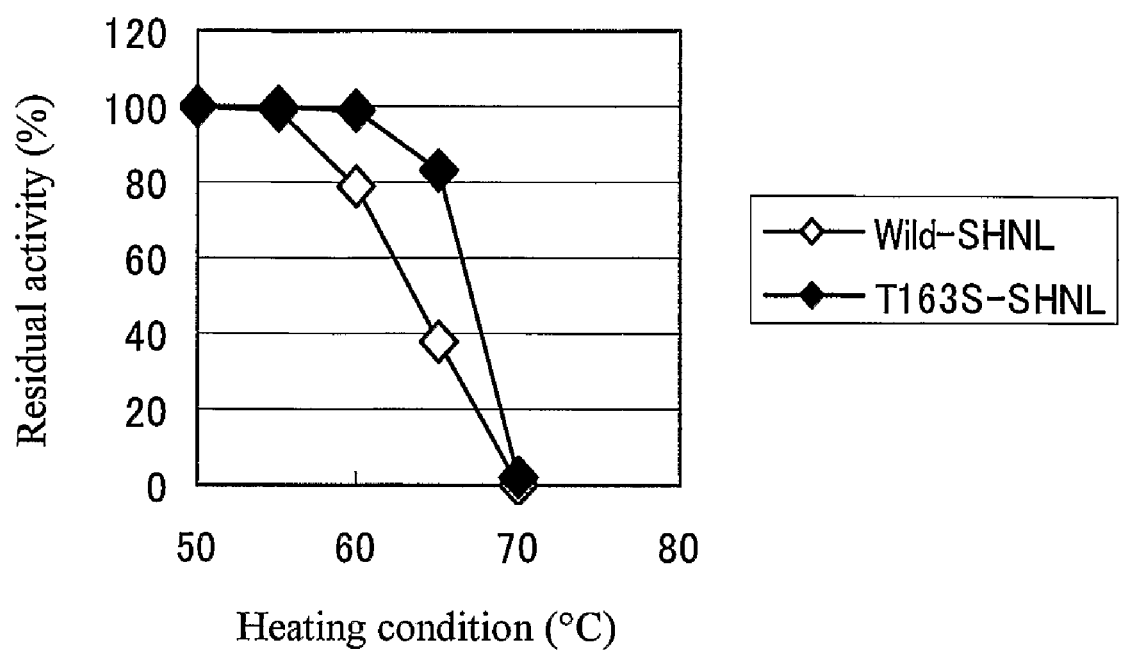
FIG. 12 is a graph showing thermostability of modified enzyme T163S-SHNL.

T163S-SHNL exhibited significantly improved thermostability compared to that of Wild-SHNL (FIG. 12). Also, thermostability of T163D-SHNL and that of T163E-SHNL at 60° C. were superior to those of Wild-SHNL. Thus, it was found that substitution of amino acid 163 that constitutes helix D3' from threonine to aspartic acid, glutamic acid, or serine could improve thermostability of SHNL.

All publications, patents, and patent applications cited herein are incorporated herein by reference in their entirety.

INDUSTRIAL APPLICABILITY

According to the present invention, the modified SHNL has superior heat tolerance and organic solvent tolerance to those of Wild-SHNL, and it can synthesize optically active cyanohydrin with the same production efficiency and optical purity as Wild-SHNL. Since the modified SHNL according to the present invention can be easily and cost-effectively purified, efficient production of a recombinant is feasible. Therefore, the modified SHNL according to the present invention is a very useful enzyme for producing optically active cyanohydrin at industrial levels.

Free Text of Sequence Listing

SEQ ID NO: 5: DNA encoding modified SHNL having a Gly-to-Asp substitution at position 165
SEQ ID NO: 6: modified SHNL having a Gly-to-Asp substitution at position 165
SEQ ID NO: 7: DNA encoding modified SHNL having a Gly-to-Glu substitution at position 165
SEQ ID NO: 8: modified SHNL having a Gly-to-Glu substitution at position 165
SEQ ID NO: 9: description of artificial sequence: primer
SEQ ID NO: 10: description of artificial sequence: primer
SEQ ID NO: 11: description of artificial sequence: primer
SEQ ID NO: 12: description of artificial sequence: primer
SEQ ID NO: 13: description of artificial sequence: primer
SEQ ID NO: 14: description of artificial sequence: primer
SEQ ID NO: 15: DNA encoding modified SHNL having a Val-to-Leu substitution at position 173
SEQ ID NO: 16: modified SHNL having a Val-to-Leu substitution at position 173
SEQ ID NO: 17: description of artificial sequence: primer
SEQ ID NO: 18: description of artificial sequence: primer
SEQ ID NO: 19: DNA encoding modified SHNL having a Met-to-Leu substitution at position 174
SEQ ID NO: 20: modified SHNL having a Met-to-Leu substitution at position 174
SEQ ID NO: 21: DNA encoding modified SHNL (Actmt022-G12-SHNL) having a Lys-to-Asn substitution at position 21
SEQ ID NO: 22: modified SHNL (Actmt022-G12-SHNL) having a Lys-to-Asn substitution at position 21
SEQ ID NO: 23: description of artificial sequence: primer
SEQ ID NO: 24: description of artificial sequence: primer
SEQ ID NO: 25: DNA encoding modified SHNL having a Lys-to-Glu substitution at position 21
SEQ ID NO: 26: modified SHNL having a Lys-to-Glu substitution at position 21
SEQ ID NO: 27: DNA encoding modified SHNL having a Lys-to-Asp substitution at position 21
SEQ ID NO: 28: modified SHNL having a Lys-to-Asp substitution at position 21
SEQ ID NO: 29: DNA encoding modified SHNL having a Lys-to-Asn substitution at position 21
SEQ ID NO: 30: modified SHNL having a Lys-to-Asn substitution at position 21
SEQ ID NO: 31: DNA encoding modified SHNL having a Gly-to-Glu substitution at position 165 and a Val-to-Leu substitution at position 173
SEQ ID NO: 32: modified SHNL having a Gly-to-Glu substitution at position 165 and a Val-to-Leu substitution at position 173
SEQ ID NO: 33: description of artificial sequence: primer
SEQ ID NO: 34: description of artificial sequence: primer
SEQ ID NO: 35: DNA encoding modified SHNL having a Gly-to-Glu substitution at position 165, a Val-to-Leu substitution at position 173, and a Met-Leu substitution at position 174
SEQ ID NO: 36: modified SHNL having a Gly-to-Glu substitution at position 165, a Val-to-Leu substitution at position 173, and a Met-Leu substitution at position 174
SEQ ID NO: 37: description of artificial sequence: primer
SEQ ID NO: 38: description of artificial sequence: primer
SEQ ID NO: 39: DNA encoding modified SHNL having a Thr-to-Asp substitution at position 163
SEQ ID NO: 40: modified SHNL having a Thr-to-Asp substitution at position 163
SEQ ID NO: 41: DNA encoding modified SHNL having a Thr-to-Glu substitution at position 163
SEQ ID NO: 42: modified SHNL having a Thr-to-Glu substitution at position 163
SEQ ID NO: 43: DNA encoding modified SHNL having a Thr-to-Ser substitution at position 163
SEQ ID NO: 44: modified SHNL having a Thr-to-Ser substitution at position 163

The invention claimed is:

1. A method for producing optically active cyanohydrin comprising
   (a) obtaining a modified S-hydroxynitrile lyase,
      wherein the modified S-hydroxynitrile lyase comprises an amino acid sequence having at least one amino acid substitution in the helix D3' region from position 163 to 174 of SEQ ID NO:2;
   (b) adding the modified S-hydroxynitrile lyase to a carbonyl compound and cyanide; and
   (c) producing optically active cyanohydrin.

2. The method of claim 1, wherein the modified S-hydroxynitrile lyase comprises an amino acid sequence having an amino acid substitution at position 165 and/or position 173 of SEQ ID NO: 2.

3. The method of claim 2, wherein the modified S-hydroxynitrile lyase comprises the amino acid sequence of SEQ ID NO: 8.

4. The method of claim 2, wherein the modified S-hydroxynitrile lyase comprises the amino acid sequence of SEQ ID NO: 16.

5. The method of claim 2, wherein the modified S-hydroxynitrile lyase comprises the amino acid sequence of SEQ ID NO: 32.

* * * * *